•

US011158810B2

(12) United States Patent
Hong et al.

(10) Patent No.: US 11,158,810 B2
(45) Date of Patent: Oct. 26, 2021

(54) POLYCYCLIC COMPOUND AND ORGANIC LIGHT EMITTING DEVICE COMPRISING SAME

(71) Applicant: LG Chem, Ltd., Seoul (KR)

(72) Inventors: Wanpyo Hong, Daejeon (KR); Hyoungcheul Kim, Daejeon (KR); Yun Hwan Kim, Daejeon (KR); Heungwoo Choi, Daejeon (KR); Jun Yun, Daejeon (KR)

(73) Assignee: LG Chem, Ltd.

( * ) Notice: Subject to any disclaimer, the term of this patent is extended or adjusted under 35 U.S.C. 154(b) by 559 days.

(21) Appl. No.: 15/770,556

(22) PCT Filed: Oct. 12, 2016

(86) PCT No.: PCT/KR2016/011424
§ 371 (c)(1),
(2) Date: Apr. 24, 2018

(87) PCT Pub. No.: WO2017/073934
PCT Pub. Date: May 4, 2017

(65) Prior Publication Data
US 2020/0127207 A1    Apr. 23, 2020

(30) Foreign Application Priority Data

Oct. 26, 2015 (KR) .................. 10-2015-0148916

(51) Int. Cl.
*H01L 51/54* (2006.01)
*H01L 51/00* (2006.01)
*C07C 25/13* (2006.01)
*C07C 255/51* (2006.01)
*H01L 51/50* (2006.01)

(52) U.S. Cl.
CPC .......... *H01L 51/0055* (2013.01); *C07C 25/13* (2013.01); *C07C 255/51* (2013.01); *C07C 2603/52* (2017.05); *H01L 51/5012* (2013.01); *H01L 51/5056* (2013.01); *H01L 51/5088* (2013.01); *H01L 51/5096* (2013.01)

(58) Field of Classification Search
None
See application file for complete search history.

(56) References Cited

U.S. PATENT DOCUMENTS

| 7,973,203 | B2 | 7/2011 | Buesing | |
| 2003/0170491 | A1* | 9/2003 | Liao | .............................. 428/690 |
| 2004/0251816 | A1 | 12/2004 | Leo et al. | |
| 2011/0156016 | A1* | 6/2011 | Kawamura | ..................... 257/40 |
| 2013/0096336 | A1* | 4/2013 | Haley | .......................... 556/429 |
| 2014/0001461 | A1* | 1/2014 | Morishita | ........... H01L 51/0055 257/40 |
| 2015/0108458 | A1* | 4/2015 | Shibata | |
| 2015/0155513 | A1* | 6/2015 | Pieh | ...................... H01L 51/504 |

FOREIGN PATENT DOCUMENTS

| JP | 3098330 B2 | 10/2000 |
| KR | 20000051826 A | 8/2000 |
| KR | 101312117 B1 | 9/2013 |
| KR | 20150010016 A | 1/2015 |
| WO | 2003012890 A2 | 2/2003 |
| WO | 2011159763 A1 | 12/2011 |
| WO | 2015009076 A1 | 1/2015 |

OTHER PUBLICATIONS

Hadizad et al., "A general synthetic route to indenofluorene derivatives as new organic semiconductors", Org. Letts. 2005, vol. 7, p. 795-797 (Year: 2005).*
Chase, D. T. et al., "6,12-Diarylindeno[1,2-b]fluorenes: syntheses, photophysics, and ambipolar OFETs", Journal of the American Chemical Society, vol. 134, pp. 10349-10352, 2012.
Shimizu, A. et al., "Indeno [2,1-b]fluorine: A20-?-Electron Hydorocarbon with Very Low-Energy Light Absorption", Angewandte Chemie, vol. 125, pp. 6192-6195, 2013.
Nishida, J. et al., "Synthesis, Crystal Structures, and Properties of 6,12-Diaryl-Substituted Indeno[1,2-b]fluorenes", Chemistry—A European Journal, vol. 18, pp. 8964-8970, 2012.
Friedrich Ebel and Werner Deuschel: 10.11-diaza-transfluoreneacendion, From the main laboratory of Badischen Anilin- and Soda-5 Fabrik AG., Ludwigshafen a. Rhein, p. 2799, Sep. 1956.
Petrovskaia et al., Investigations of the Reaction Mechanisms of 1,2-Indanediones with Amino Acids, J. Org. Chem. 66, paqges 7666-7675, 2001 Philadelphia, Pennsylvania.
Chase et al., Electron-Accepting 6,12-Diethynylindeno[1,2-b]fluorenes: Synthesis, Crystal Structures, and Photophysical Properties, Angew. Chem. Int. Ed., 50, pp. 11103-11106, 2011.
Fix et al., Indeno[2,1-c]fluorene: A new Electron-Acceptaing Scaffold for Organiac Electronics, vol. 15, No. 6, pp. 1362-1365, vol. 15, No. 6, 2013.
International Search Report for PCT/KR2016/011424 dated Jan. 24, 2017.
Chinese Search Report for Application No. CN201680062432.2 dated May 20, 2020, 4 pages.
Shimizu et al., Indeno[2,1-a] fluorene: An Air-Stable ortho-Quinodimethane Derivative**, Angew.Che.Int.Ed., 2011, vol. 50, pp. 6906-6910.

* cited by examiner

*Primary Examiner* — Jennifer A Boyd
*Assistant Examiner* — Seokmin Jeon
(74) *Attorney, Agent, or Firm* — Lerner, David, Littenberg, Krumholz & Mentlik, LLP

(57) ABSTRACT

The present specification provides a multicyclic compound of Chemical Formula 1, and an organic light emitting device including the same.

18 Claims, 4 Drawing Sheets

[FIG. 1]
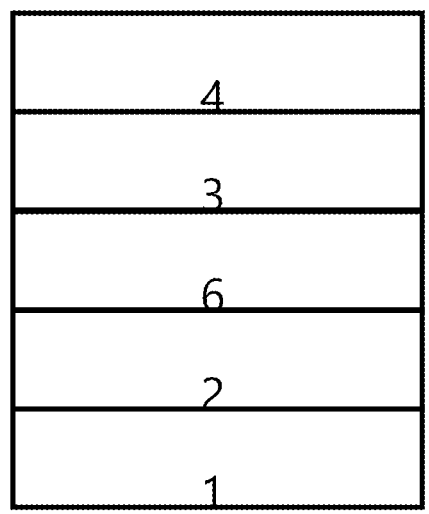

[FIG. 2]
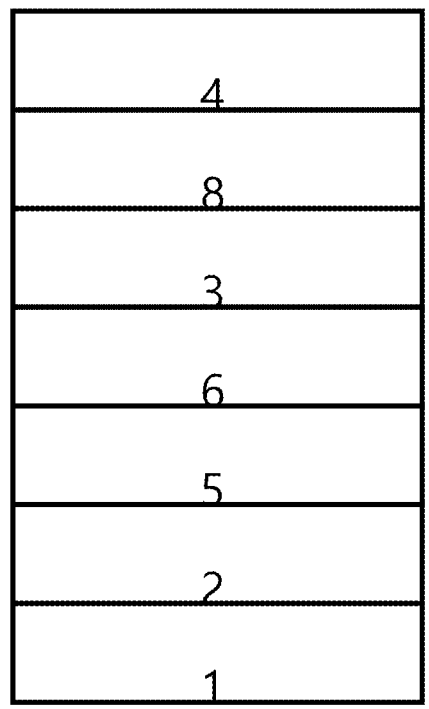

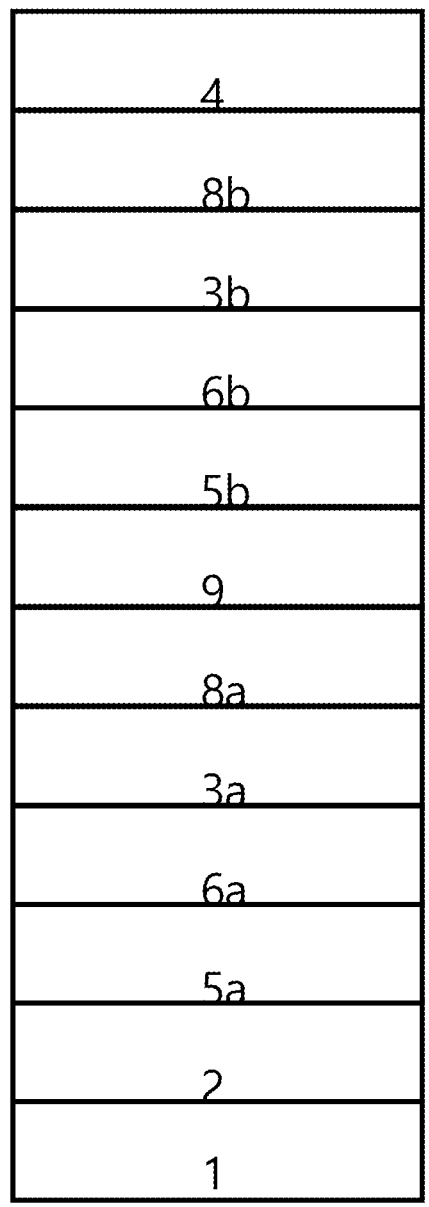
[FIG. 3]

[FIG. 4]
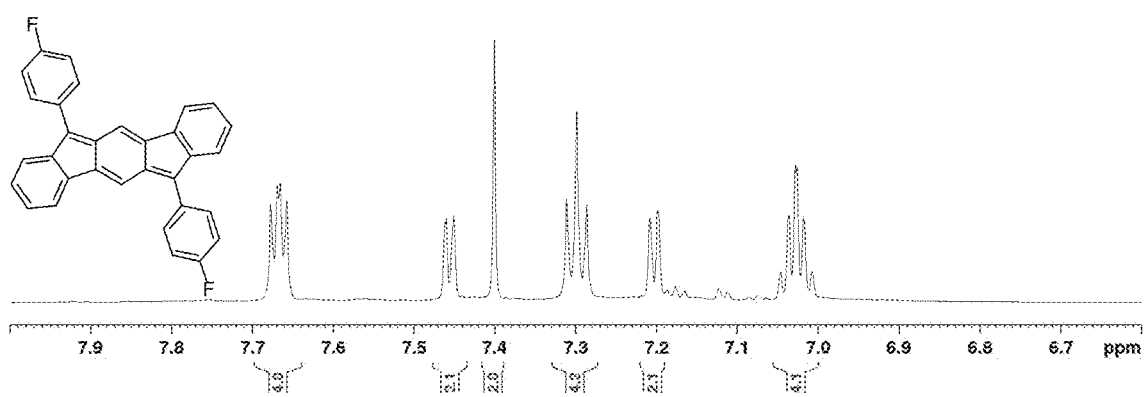

POLYCYCLIC COMPOUND AND ORGANIC LIGHT EMITTING DEVICE COMPRISING SAME

CROSS-REFERENCE TO RELATED APPLICATIONS

The present application is a national phase entry under U.S.C. § 371 of International Application No. PCT/KR2016/011424 filed on Oct. 12, 2016, which claims priority from Korean Patent Application No. 10-2015-0148916, filed Oct. 26, 2015, the entire contents of which are incorporated herein by reference.

TECHNICAL FIELD

The present specification relates to a multicyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a multicyclic compound and an organic light emitting device including the same.

Technical Solution

One embodiment of the present specification provides a compound represented by the following Chemical Formula 1:

[Chemical Formula 1]

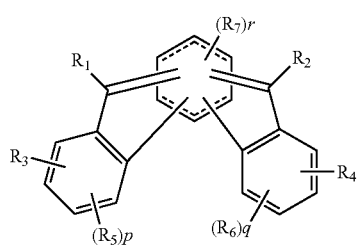

In Chemical Formula 1, $R_1$ and $R_2$ are the same as or different from each other, and each independently a substituted or unsubstituted phenyl group, or a substituted or unsubstituted N-containing monocyclic heterocyclic group, $R_3$ and $R_4$ are the same as or different from each other, and each independently hydrogen; deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted alkylsilyl group; a substituted or unsubstituted arylsilyl group; a substituted or unsubstituted cyanoaryl group; a substituted or unsubstituted alkylaryl group; a substituted or unsubstituted haloalkylaryl group; a substituted or unsubstituted aryl group; a substituted or unsubstituted haloaryl group; or a substituted or unsubstituted heterocyclic group, $R_5$ to $R_7$ are the same as or different from each other, and each independently hydrogen; deuterium; a halogen group; a substituted or unsubstituted alkyl group; a substituted or unsubstituted haloalkyl group; a substituted or unsubstituted cycloalkyl group; a substituted or unsubstituted alkoxy group; a substituted or unsubstituted haloalkoxy group; a substituted or unsubstituted aryloxy group; a substituted or unsubstituted alkenyl group; a substituted or unsubstituted aralkyl group; a substituted or unsubstituted aralkenyl group; a substituted or unsubstituted alkylaryl group; a substituted or unsubstituted haloalkylaryl group; a substituted or unsubstituted aryl group; a substituted or unsubstituted haloaryl group; or a substituted or unsubstituted heterocyclic group, p and q are each an integer of 0 to 3, r is an integer of 0 to 2, when p is 2 or greater, $R_5$s are the same as or different from each other, when q is 2 or greater, $R_6$s are the same as or different from each other, and when r is 2, $R_7$s are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

Compounds described in the present specification can be used as a material of an organic material layer of an organic light emitting device. Compounds according to at least one embodiment are capable of enhancing efficiency, low driving voltage and/or enhancing lifespan properties in an organic light emitting device. Particularly, compounds described in the present specification can be used as a material of hole injection, hole transfer, hole injection and hole transfer, light emission, electron transfer or electron injection. In addition, compounds described in the present specification can be preferably used as a material of a light emitting layer, electron transfer or electron injection. More preferably, when using compounds described in the present specification as a material of hole injection, hole transfer, electron blocking layer or charge generation layer, properties of low voltage, high efficiency and/or long lifespan are exhibited.

DESCRIPTION OF DRAWINGS

FIG. 1 illustrates an organic light emitting device formed with a substrate (1), an anode (2), a hole transfer layer (6), a light emitting layer (3) and a cathode (4).

FIG. 2 illustrates an organic light emitting device formed with a substrate (1), an anode (2), a hole injection layer (5), a hole transfer layer (6), a light emitting layer (3), an electron transfer layer (8) and a cathode (4).

FIG. 3 illustrates an organic light emitting device including a substrate (1), an anode (2) and a cathode (4), including two units that include a hole injection layer (5a, 5b), a hole transfer layer (6a, 6b), a light emitting layer (3a, 3b) and an electron transfer layer (8a, 8b) between the anode and the cathode, and provided with a charge generation layer (9) between the units.

FIG. 4 is a result measuring the compound represented by Chemical Formula 1 with Bruker 700 MHz $^1$H NMR using tetrahydrofuran-d8 at room temperature.

1: Substrate
2: Anode
3, 3a, 3b: Light Emitting Layer
4: Cathode
5, 5a, 5b: Hole Injection Layer
6, 6a, 6b: Hole Transfer Layer
8, 8a, 8b: Electron Transfer Layer

MODE FOR DISCLOSURE

Hereinafter, the present specification will be described in more detail.

One embodiment of the present specification provides a compound represented by Chemical Formula 1.

The dotted line part of Chemical Formula 1 means a conjugate bond.

The indenofluorene structure of Chemical Formula 1 is a structure having two pentagonal rings in the center core, and has 20-π-electrons, and therefore, has antiaromatic properties. Accordingly, a tendency to regain aromaticity by accepting electrons is quite high, and suitable deposition temperatures may be maintained as well as exhibiting excellent heat resistance since 5 or more aromatic rings are linked, and therefore, an organic light emitting device may be manufactured through deposition. In addition, high purification is possible since sublimation purification is capable of being carried out due to having a sublimation temperature of approximately 200° C. or higher, and a film-forming apparatus or an organic light emitting device is not contaminated since scattering into the film-forming apparatus for deposition does not occur when manufacturing the device. Moreover, electron acceptability may be further enhanced or crystallinity may be further reduced by introducing specific substituents to the ring at the end. Accordingly, the inventors of the present disclosure have found out that low voltage of driving voltage or long lifespan is capable of being obtained when using the compound of Chemical Formula 1 having such properties as a material for an organic light emitting device, particularly, in a hole injection layer, a hole transfer layer, an electron blocking layer or a charge generation layer. When using the compounds described in the present specification in an organic light emitting device, the device lifespan may be enhanced and power consumption may be reduced by accomplishing a lower driving voltage compared to using existing aromatic diamine derivatives such as NPD or using electron accepting dopants. In addition, depositions are readily carried out compared to materials having low molecular weight and high sublimation properties such as F4TCNQ, and stable interfaces may be formed with electrodes or adjacent organic material layers compared to HAT-CN.

Examples of the substituents are described below, however, the substituents are not limited thereto.

In the present specification, the term "substituted or unsubstituted" means being substituted with one or more substituents selected from the group consisting of hydrogen; deuterium; a halogen group; a nitrile group; an alkoxy group; a haloalkoxy group; an aryloxy group; an alkyl group; a haloalkyl group; a cycloalkyl group; an alkenyl group; a haloaryl group; an aralkyl group; an aralkenyl group; an alkylaryl group; a haloalkylaryl group; an aryl group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, examples of the halogen group may include fluorine, chlorine, bromine or iodine.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to still another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group is not particularly limited, but preferably has 1 to 40 carbon atoms. According to one embodiment, the number of carbon atoms of the alkoxy group is from 1 to 10. According to another embodiment, the number of carbon atoms of the alkoxy group is from 1 to 6. Specific examples of the alkoxy group may include a methoxy group, an ethoxy group, a propoxy group, an isobutyloxy group, a sec-butyloxy group, a pentyloxy group, an iso-amyloxy group, a hexyloxy group and the like, but are not limited thereto.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. Examples of the monocyclic aryl group may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group, a triphenylene group and the like, but are not limited thereto.

In the present specification, the fluorenyl group may be substituted, and two of the substituents may bond to each other to form a spiro structure.

When the fluorenyl group is substituted,

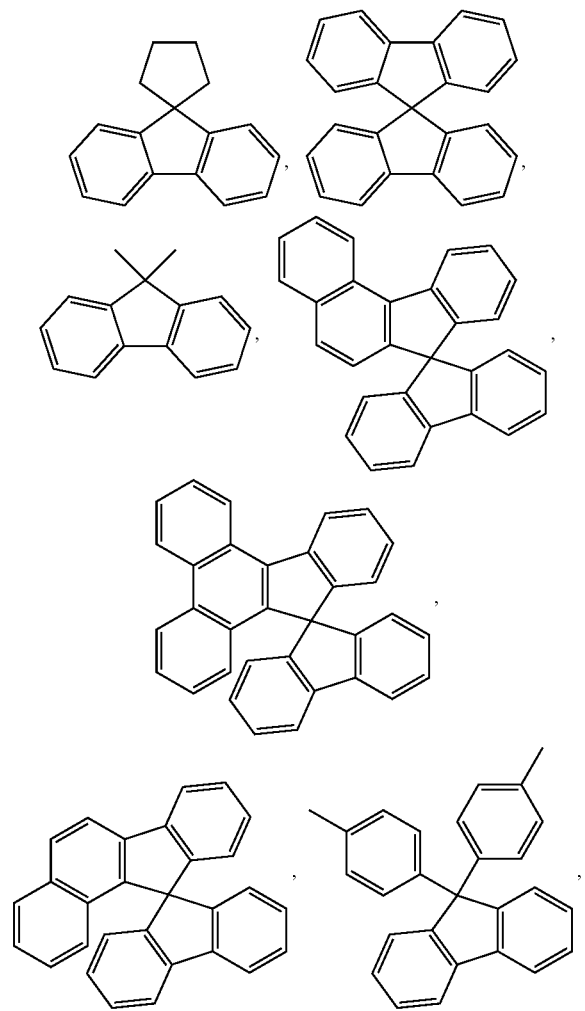

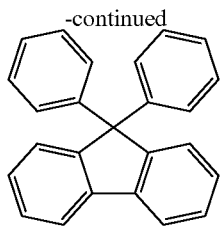

and the like may be included. However, the structure is not limited thereto.

In the present specification, the heterocyclic group is a heterocyclic group including one or more of N, O, S, Si and Se as a heteroatom, and although not particularly limited thereto, the number of carbon atoms is preferably from 2 to 60. Examples of the heterocyclic group may include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a carboline group, an acenaphthoquinoxaline group, an indenoquinazoline group, and indenoisoquinoline group, an indenoquinoline group, a pyridoindole group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofurane group, a dibenzofuran group, a phenanthroline group, a thiazolyl group, an isoxazolyl group, an oxadiazolyl group, a thiadiazolyl group, a benzothiazolyl group, a phenoxazinyl group, a phenothiazinyl group, a dibenzofuranyl group and the like, but are not limited thereto. The heterocyclic group includes an aliphatic heterocyclic group and an aromatic heterocyclic group.

In the present specification, the descriptions on the aryl group provided above may be used on the aryl group in the aralkyl group, the aralkenyl group, the alkylaryl group, the haloaryl group, the haloalkylaryl group, the arylsilyl group and the cyanoaryl group.

In the present specification, the descriptions on the alkyl group provided above may be used on the alkyl group in the aralkyl group, the alkylaryl group, the haloalkyl group, the haloalkylaryl group and the alkylsilyl group.

In the present specification, the descriptions on the alkenyl group provided above may be used on the alkenyl group in the aralkenyl group.

In the present specification, the descriptions on the alkoxy group provided above may be used on the alkoxy group in the haloalkoxy group.

In the present specification, the haloalkyl group, the haloalkoxy group, the haloalkylaryl group and the haloaryl group respectively mean an alkyl group, an alkoxy group, an alkylaryl group and an aryl group substituted with halogen.

In the present specification, the cyanoaryl group means an aryl group substituted with one or more nitrile groups.

In the present specification, the alkylsilyl group means a silyl group substituted with an alkyl group, and the arylsilyl group means a silyl group substituted with an aryl group, which may be represented by —SiRR'R", and herein R, R' and R" are an alkyl group or an aryl group. Herein, the descriptions on the alkyl group and the aryl group provided above may be used on the alkyl group and the aryl group, respectively.

In the present specification, a germanium group may be represented by the chemical formula of —GeR$_a$RbR$_c$, and R$_a$, R$_b$ and R$_c$ may each be hydrogen; a substituted or unsubstituted alkyl group; or a substituted or unsubstituted aryl group. Specifically, the germanium group may be a trimethylgermanium group, a triethylgermanium group, a t-butyldimethylgermanium group and the like, but is not limited thereto.

According to one embodiment of the present specification, Chemical Formula 1 may be represented by one of the following Chemical Formulae 2, 3 and 5 to 7.

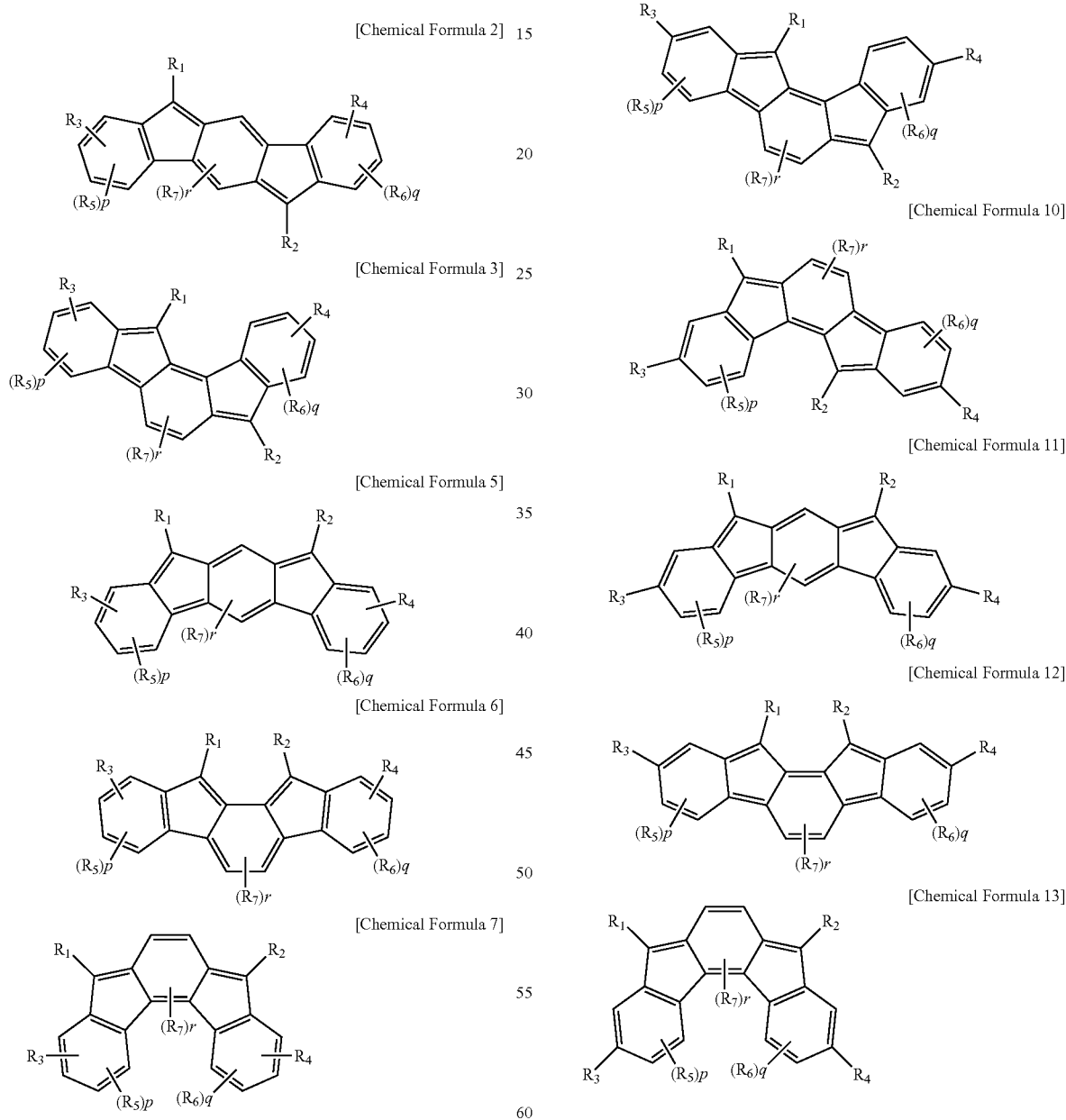

In Chemical Formulae 2, 3 and 5 to 7, definitions of substituents are the same as in Chemical Formula 1.

According to one embodiment of the present specification, Chemical Formula 1 may be represented by one of the following Chemical Formulae 8 to 13.

In Chemical Formulae 8 to 13, definitions of substituents are the same as in Chemical Formula 1.

According to one embodiment of the present specification, $R_1$ and $R_2$ are the same as or different from each other, and may be each independently represented by the following Chemical Formula 14.

[Chemical Formula 14]

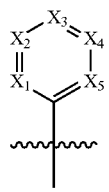

In Chemical Formula 14, $X_1$ to $X_5$ are the same as or different from each other, and each independently CH, CR or N, and R is deuterium; a halogen group; a nitrile group; an alkyl group; a haloalkyl group; an alkoxy group; or a haloalkoxy group.

According to one embodiment, R of Chemical Formula 14 is a fluoro group, a nitrile group, $CH_3$, $CF_3$, $OCH_3$ or $OCF_3$.

According to one embodiment of the present specification, Chemical Formula 14 may be selected from among the following structural formulae.

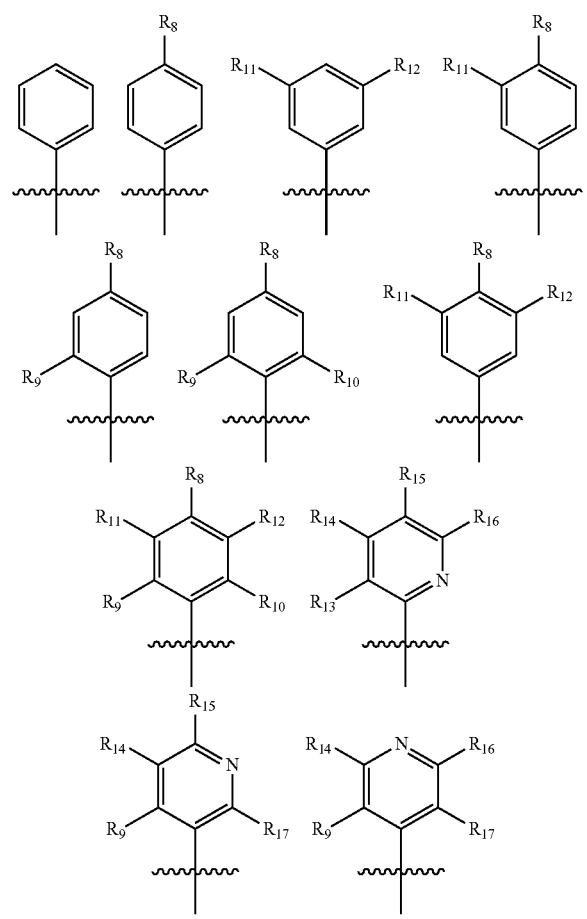

In the structural formulae, $R_8$ to $R_{12}$ are the same as or different from each other, and each independently deuterium; a halogen group; a nitrile group; an alkyl group; a haloalkyl group; an alkoxy group; or a haloalkoxy group, and $R_{13}$ to $R_{17}$ are the same as or different from each other, and each independently hydrogen; deuterium; a halogen group; a nitrile group; an alkyl group; a haloalkyl group; an alkoxy group; or a haloalkoxy group.

According to one embodiment of the present specification, Chemical Formula 14 may be selected from among the following structural formulae.

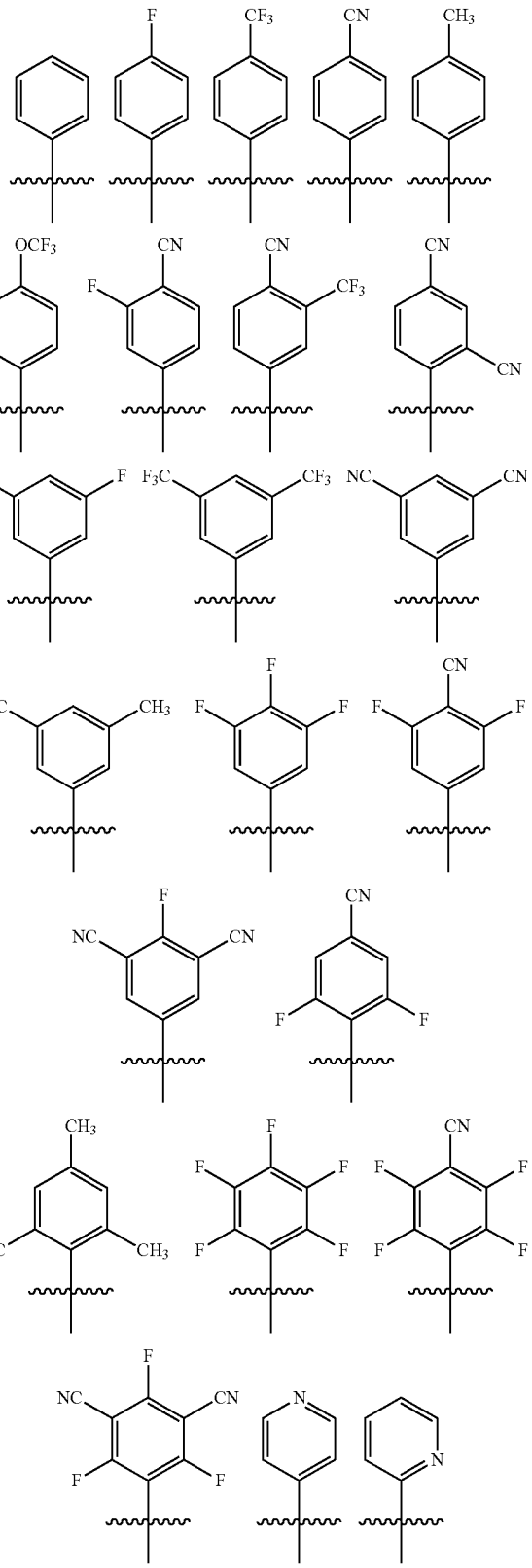

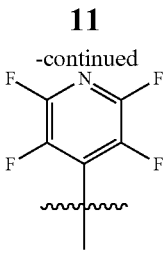

According to one embodiment of the present specification, $R_3$ and $R_4$ are the same as or different from each other, and each independently hydrogen; deuterium; a halogen group; a nitrile group; a substituted or unsubstituted haloalkyl group; a substituted or unsubstituted haloalkoxy group; a substituted or unsubstituted haloalkylaryl group; a substituted or unsubstituted aryl group; a substituted or unsubstituted haloaryl group; or a substituted or unsubstituted heterocyclic group.

According to one embodiment of the present specification, $R_3$ and $R_4$ are the same as or different from each other, and each independently hydrogen; deuterium; a halogen group; a nitrile group; a haloalkyl group; a haloalkoxy group; a haloalkylaryl group; an aryl group; a haloaryl group; or a heterocyclic group containing N, O or S.

According to one embodiment of the present specification, $R_3$ and $R_4$ are the same as or different from each other, and each independently hydrogen; deuterium; a fluoro group; a nitrile group; a fluoroalkyl group; a fluoroalkoxy group; a fluoroalkylaryl group; an aryl group; a fluoroaryl group; or a heterocyclic group containing N, O or S.

According to one embodiment of the present specification, $R_3$ and $R_4$ are the same as or different from each other, and each independently hydrogen; deuterium; a fluoro group; a nitrile group; a fluoroalkyl group; a fluoroalkoxy group; a fluoroalkylaryl group; an aryl group; a fluoroaryl group; a thiophene group, a pyridine group or a quinoline group.

According to one embodiment of the present specification, $R_5$ and $R_6$ are the same as or different from each other, and each independently hydrogen; deuterium; a halogen group; a substituted or unsubstituted alkyl group; a substituted or unsubstituted haloalkyl group; a substituted or unsubstituted alkoxy group; a substituted or unsubstituted haloalkoxy group; a substituted or unsubstituted alkylaryl group; a substituted or unsubstituted haloalkylaryl group; a substituted or unsubstituted aryl group; a substituted or unsubstituted haloaryl group; or a substituted or unsubstituted heterocyclic group.

According to one embodiment of the present specification, $R_5$ and $R_6$ are the same as or different from each other, and each independently hydrogen; deuterium; a halogen group; a substituted or unsubstituted haloalkyl group; a substituted or unsubstituted haloalkoxy group; a substituted or unsubstituted haloalkylaryl group; or a substituted or unsubstituted haloaryl group.

According to one embodiment of the present specification, $R_5$ and $R_6$ are the same as or different from each other, and each independently hydrogen; deuterium; a halogen group; a haloalkyl group; a haloalkoxy group; a haloalkylaryl group; or a haloaryl group.

According to one embodiment of the present disclosure, the compound of Chemical Formula 1 may be any one selected from among the following compounds.

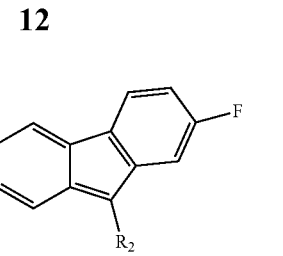

-continued
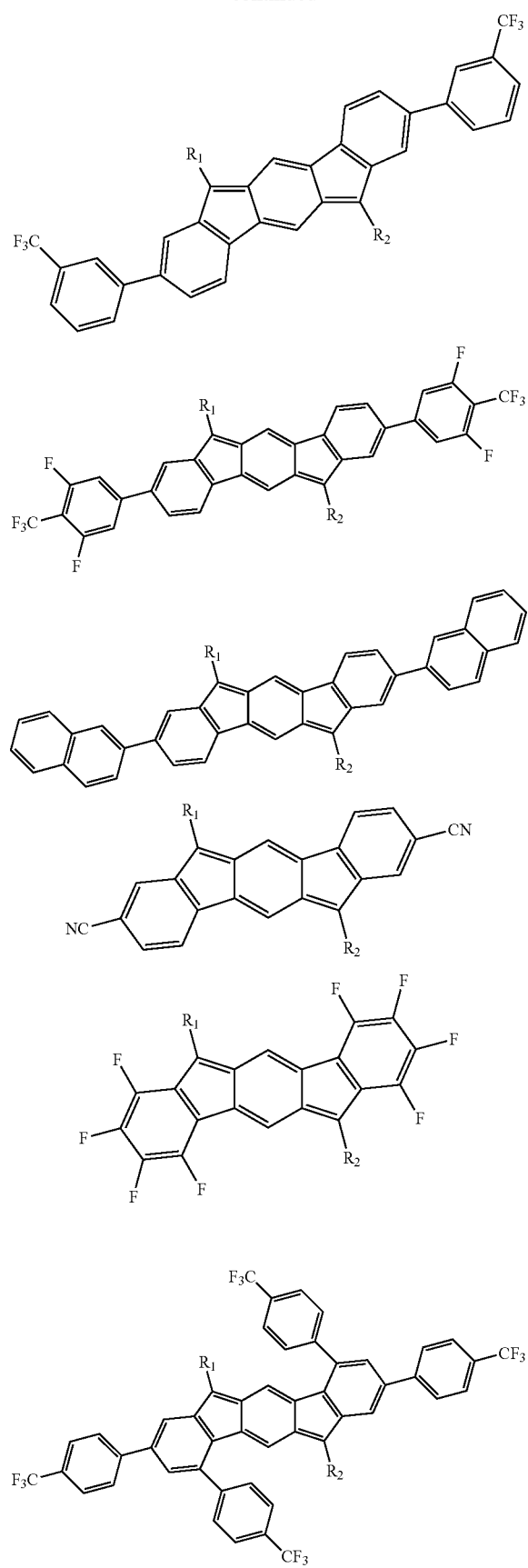
-continued
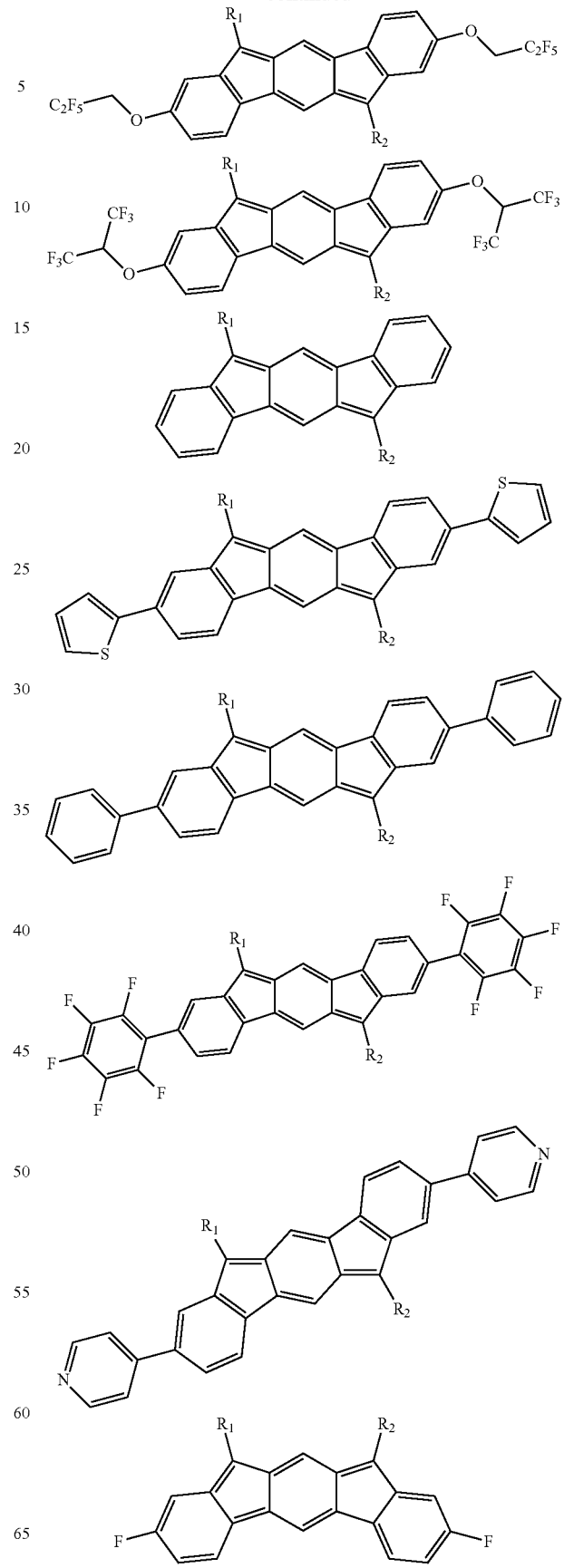

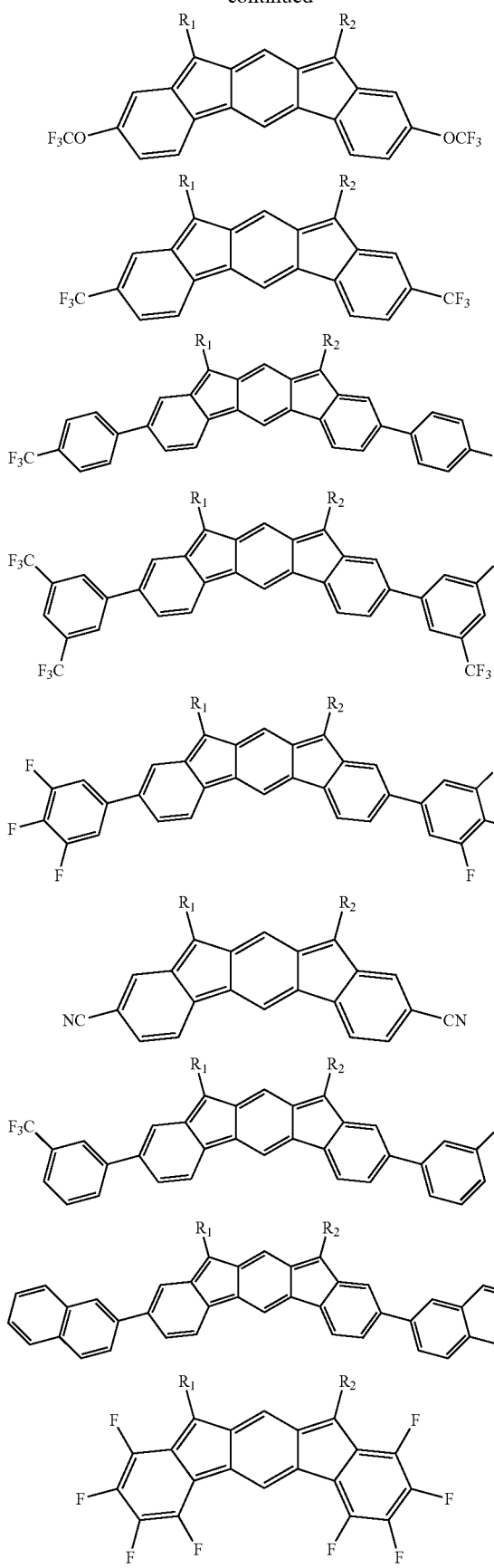
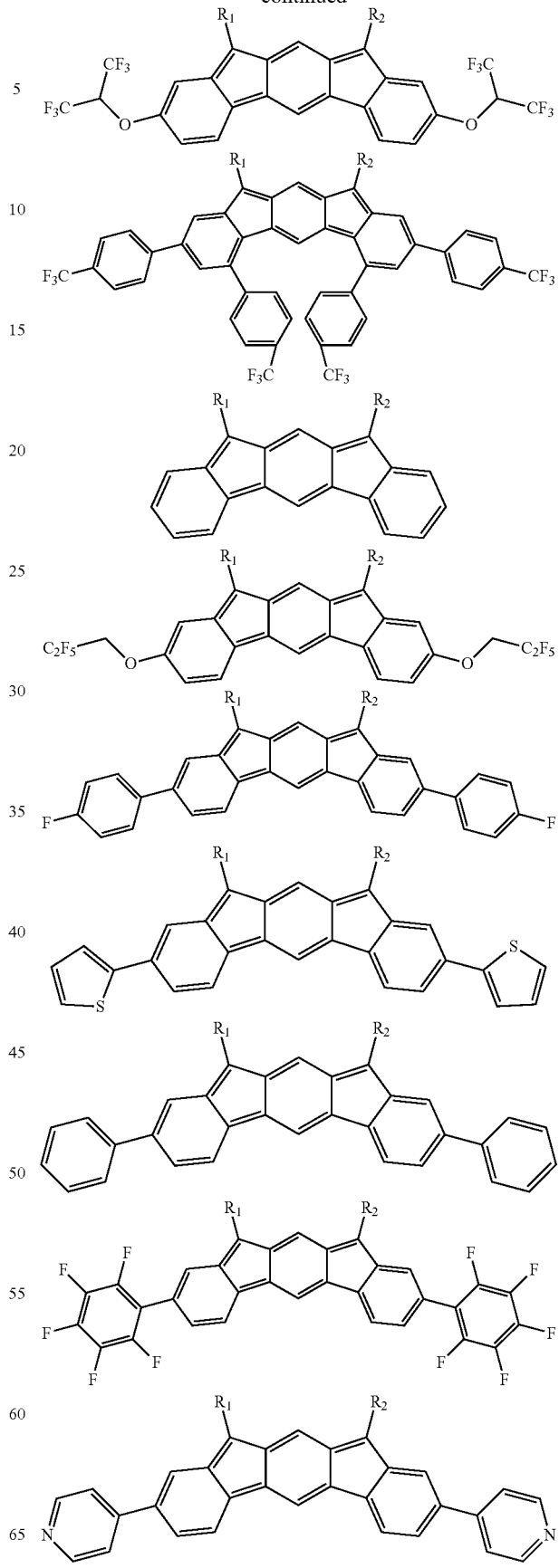

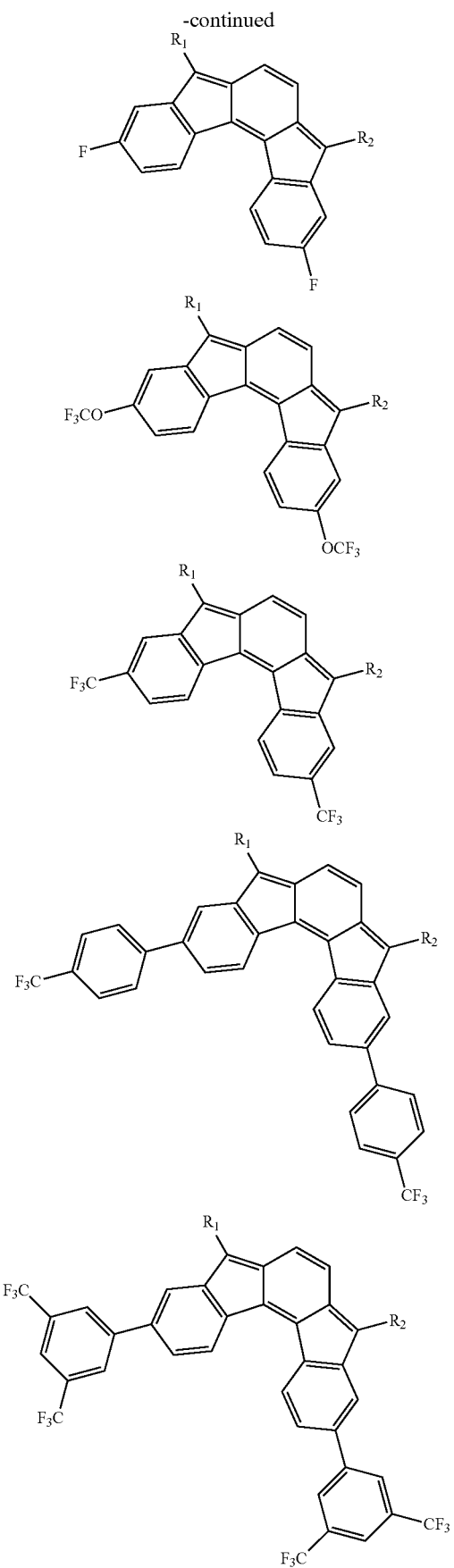
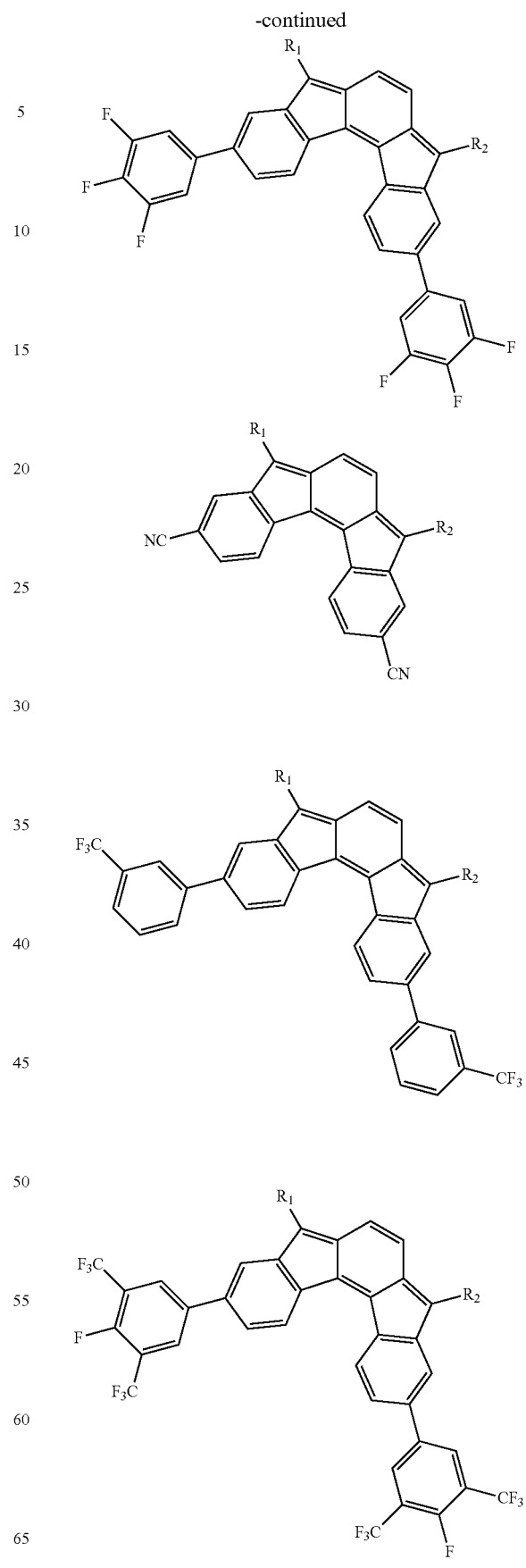

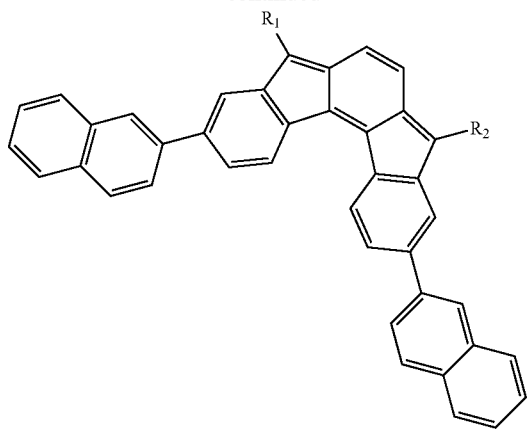
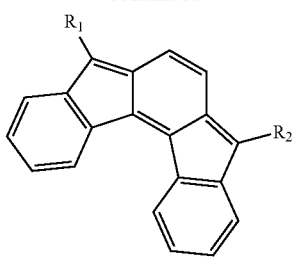
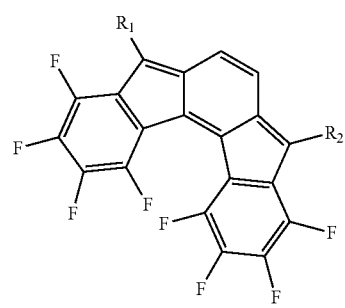
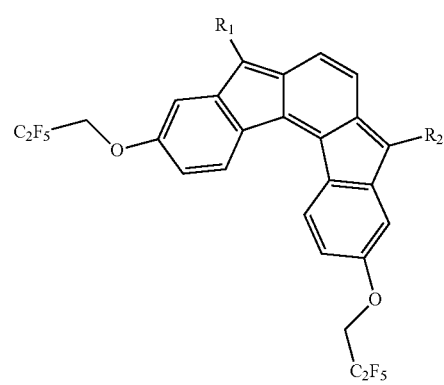
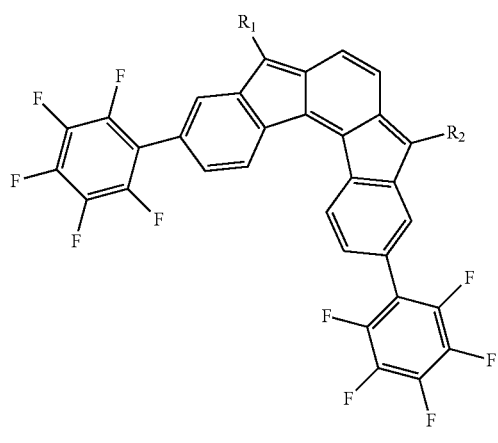
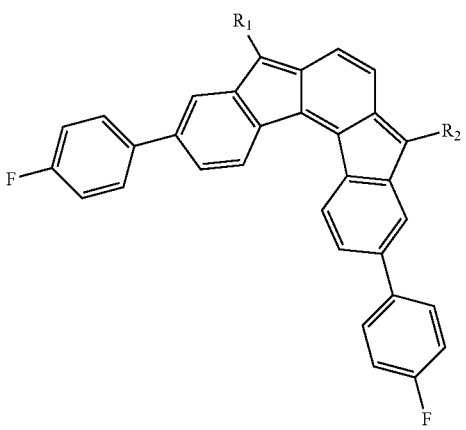
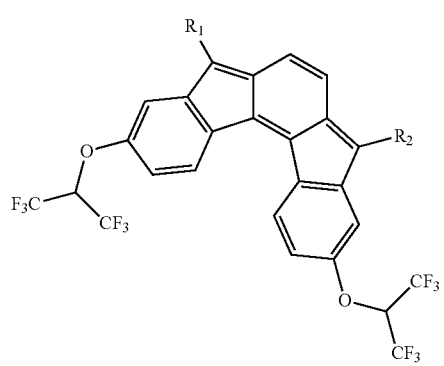
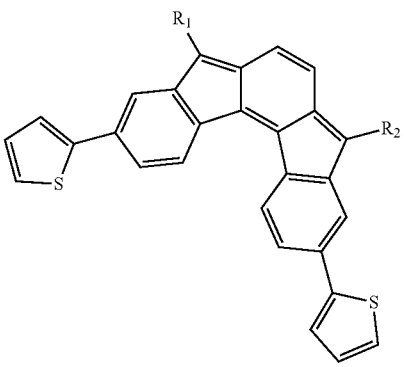

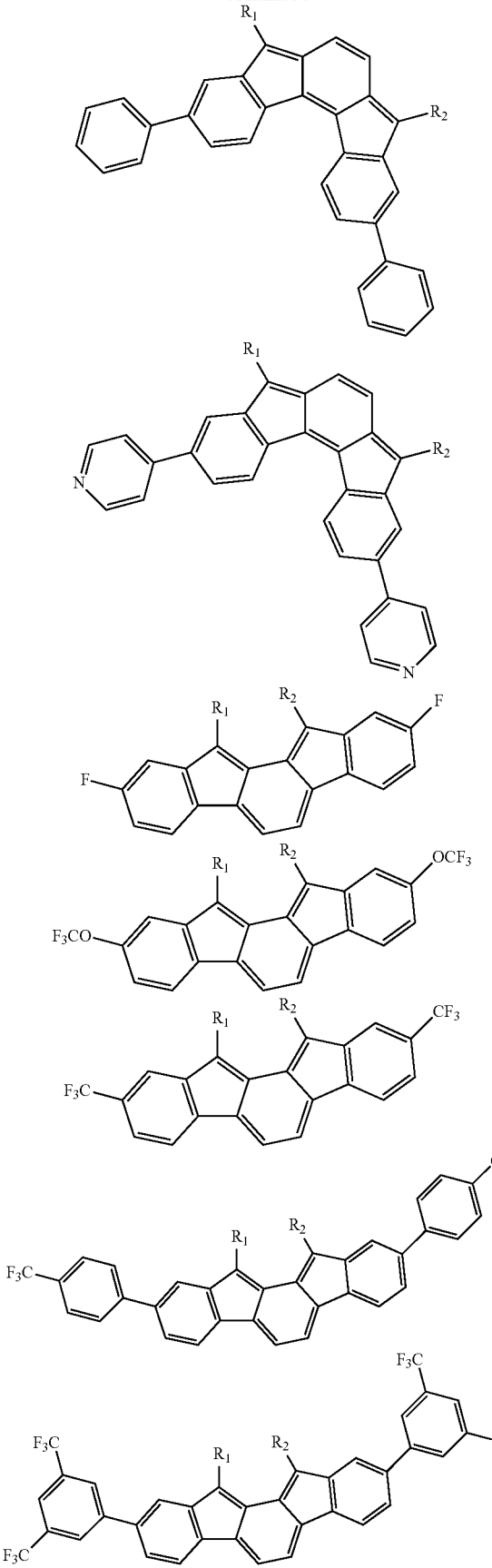
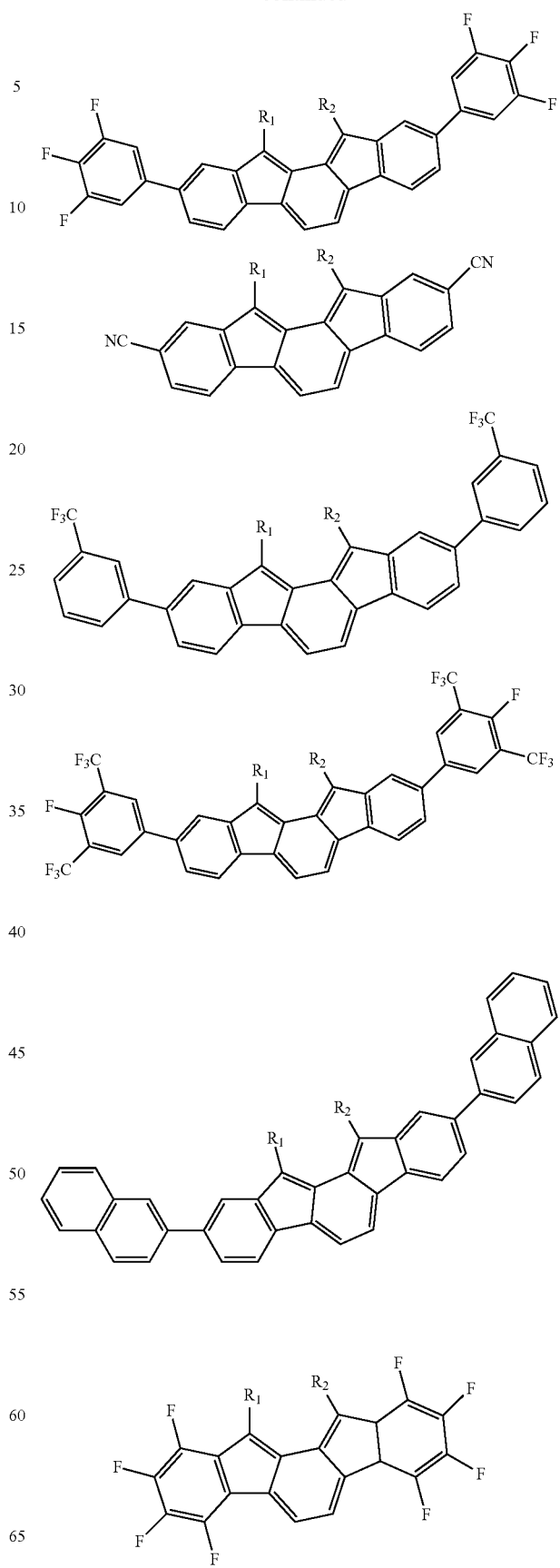

23
-continued
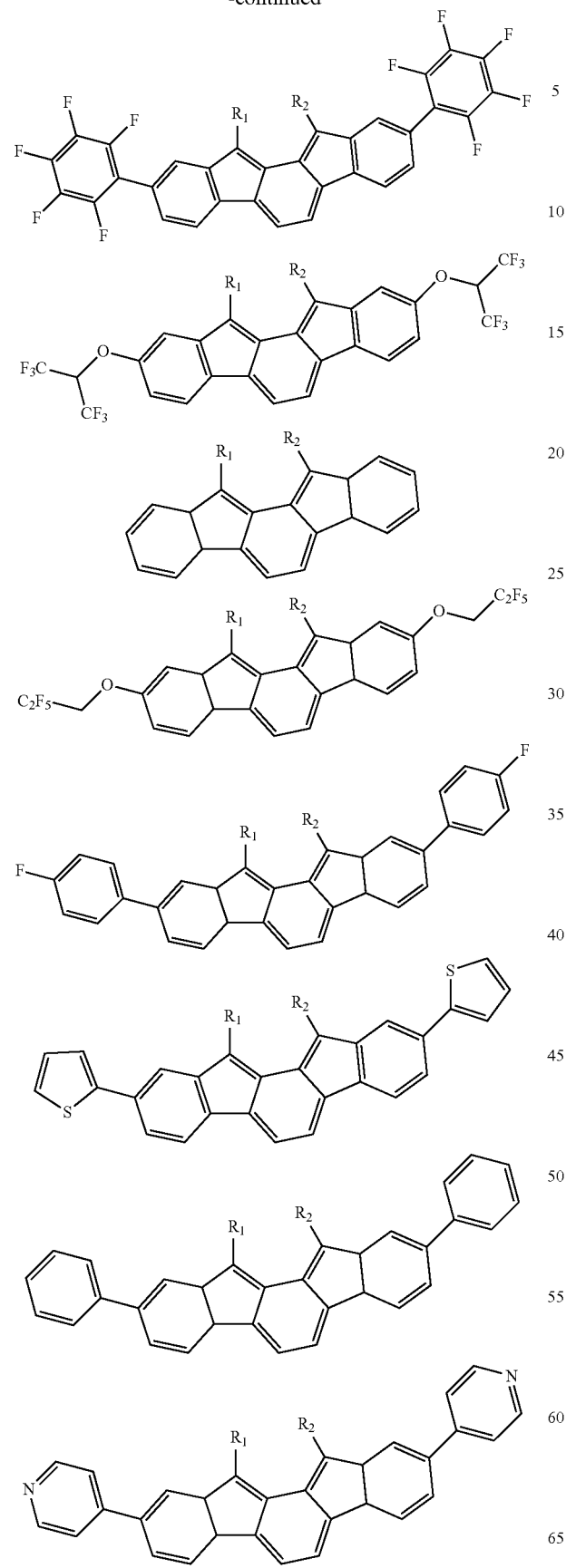
24
-continued
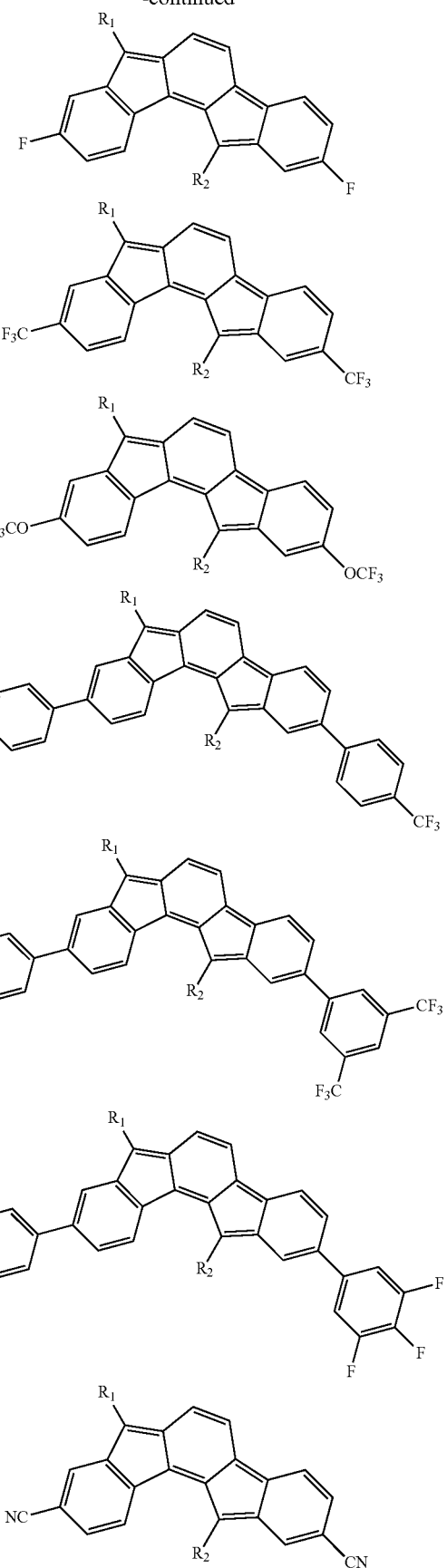

-continued
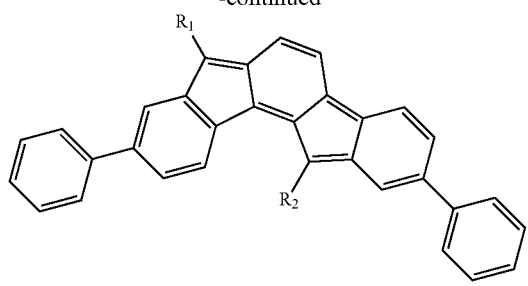
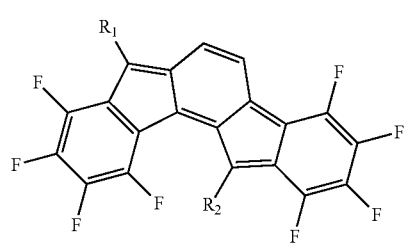
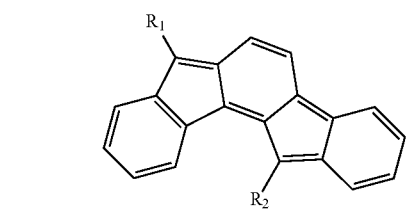
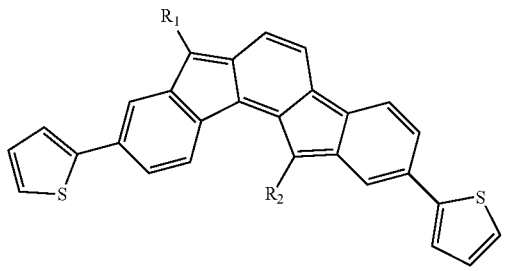
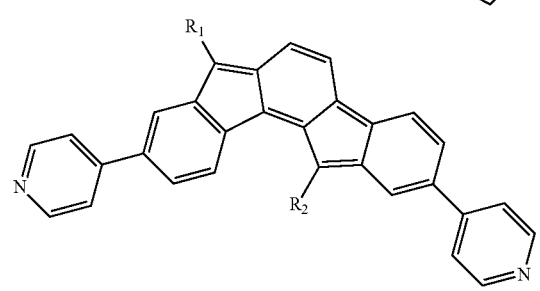
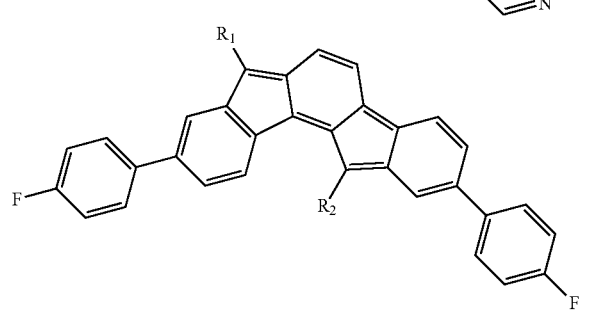
-continued
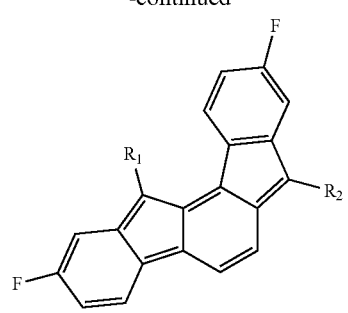
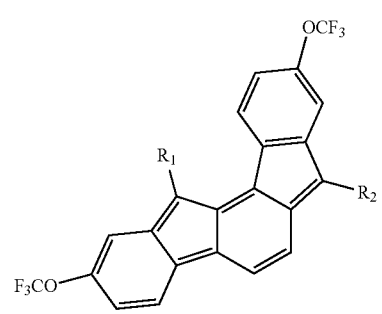
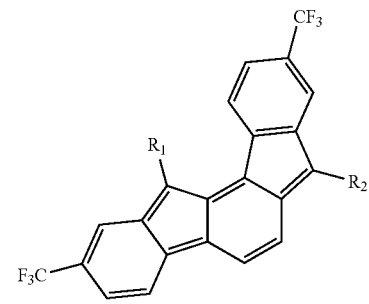
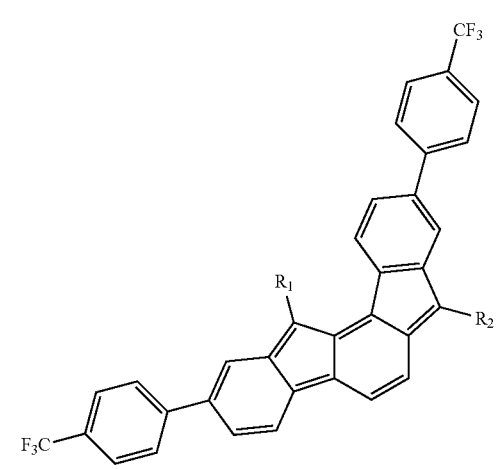

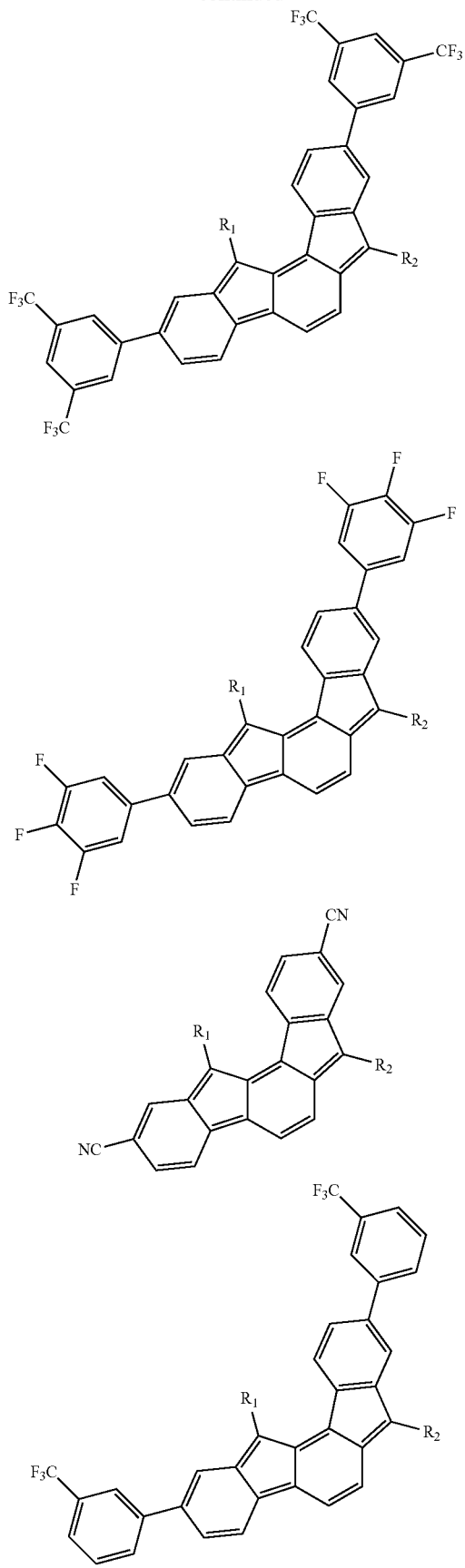
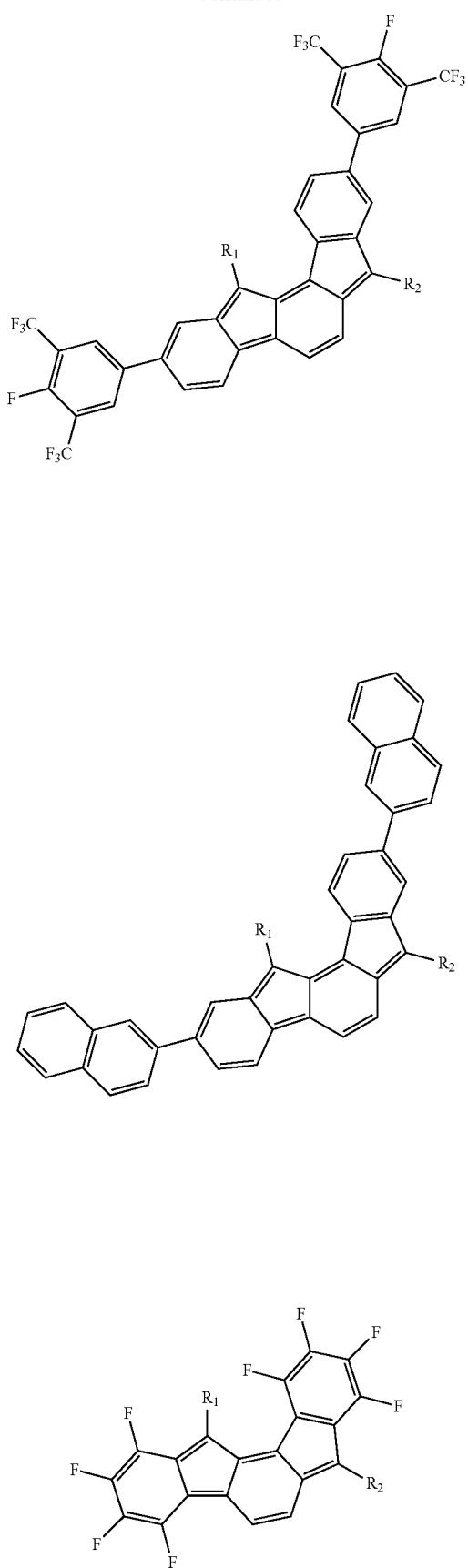

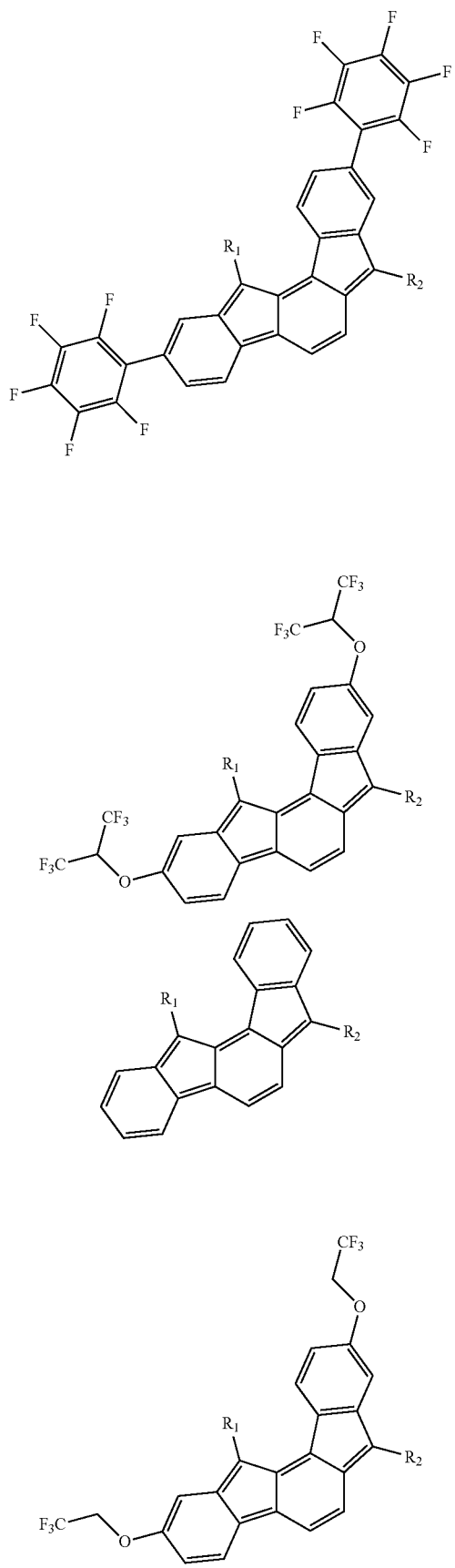
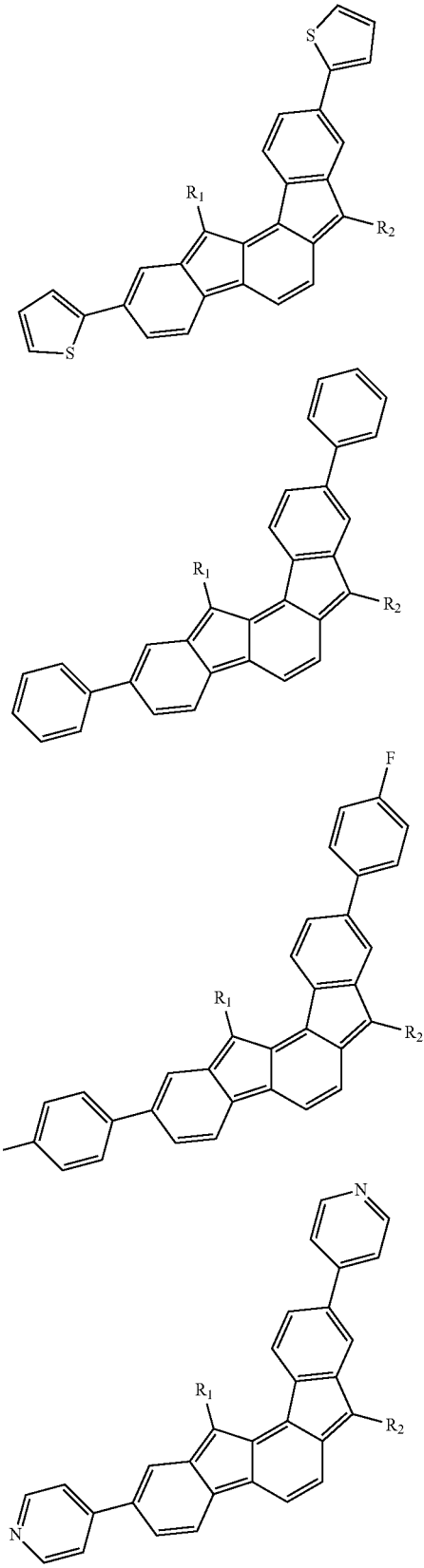
In the structural formulae, definitions of $R_1$ and $R_2$ are the same as in Chemical Formula 1.

The compound of Chemical Formula 1 described above may be prepared using materials and reactions conditions known in the art. For example, indenofluorenedione is prepared according to the following Reaction Formula 1 with reference to synthesis methods described in the literature [Chemische Berichte (1956) volume 89 page 2799] or [Journal of Organic Chemistry (2001) volume 66 page 7666], or Japanese Patent No. 3098330.

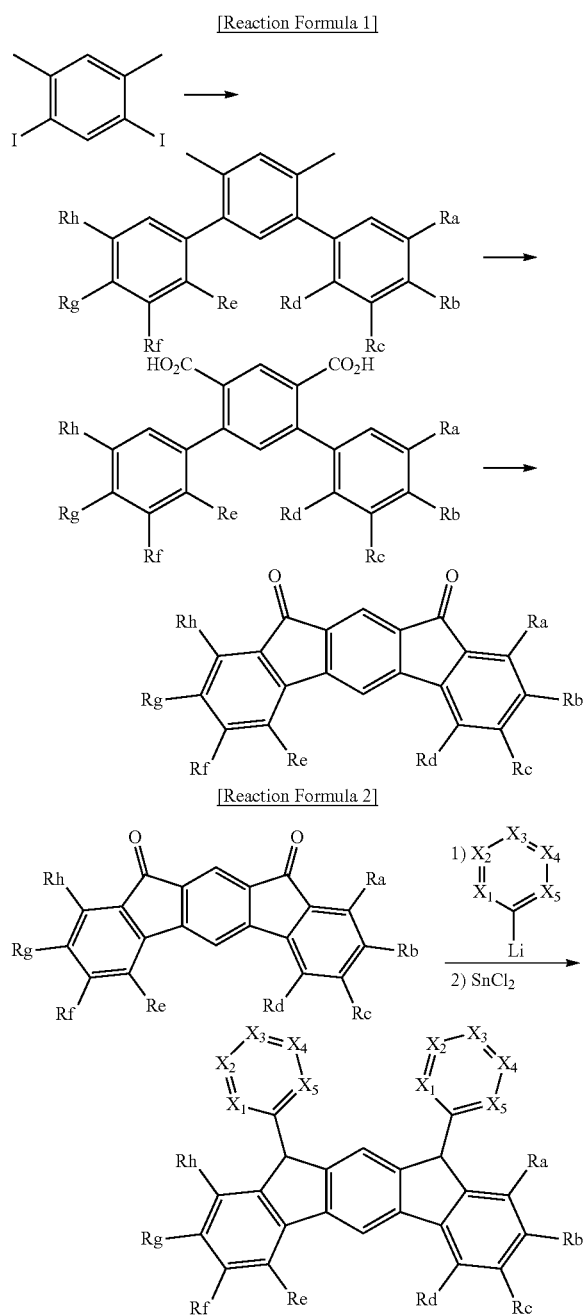

In Reaction Formulae 1 and 2, one of Ra to Rd and one of Re to Rh have the same definitions as $R_3$ and $R_4$, respectively, and the rest have the same definitions as $R_5$ or $R_6$, and definitions of $X_1$ to $X_5$ are the same as in Chemical Formula 14.

Reaction Formulae 1 and 2 illustrate a process preparing the compound of Chemical Formula 5, however, based on these reaction formulae, the remaining compounds may also be prepared using reaction conditions or materials known in the art. In addition, the types and the numbers of the substituents of the compounds may be modified as necessary.

In addition, the present specification provides an organic light emitting device including the compound represented by Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present specification may be formed in a single layer structure, but may be formed in a multilayer structure in which two or more organic material layers are laminated. For example, the organic light emitting device of the present specification may have a structure further including, as the organic material layer in addition to a light emitting layer, at least one layer of a hole injection layer, a hole buffer layer, a hole transfer layer, an electron blocking layer, a hole blocking layer, an electron transfer layer and an electron injection layer. However, the structure of the organic light emitting device is not limited thereto, and may include less numbers of organic material layers.

In one embodiment of the present specification, the organic material layer includes a light emitting layer, and the light emitting layer includes a compound represented by the following Chemical Formula A-1.

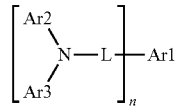

[Chemical Formula A-1]

In Chemical Formula A-1,

Ar1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, L is a direct bond; a substituted or unsubstituted arylene group; or a substituted or unsubstituted heteroarylene group, Ar2 and Ar3 are the same as or different from each other, and each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or may bond to each other to form a substituted or unsubstituted ring, n is an integer of 1 or greater, and when n is 2 or greater, substituents in the parentheses are the same as or different from each other.

According to one embodiment of the present specification, the organic material layer includes a light emitting layer, and the light emitting layer includes the compound represented by Chemical Formula A-1 as a dopant of the light emitting layer.

In one embodiment of the present specification, L is a direct bond.

According to one embodiment of the present specification, n is 2.

In one embodiment of the present specification, Ar1 is a substituted or unsubstituted divalent pyrene group.

In another embodiment, Ar1 is a divalent pyrene group unsubstituted or substituted with a methyl group, an ethyl group, a t-butyl group or an isopropyl group.

In another embodiment, An is a divalent pyrene group.

In one embodiment of the present specification, Ar2 and Ar3 are the same as or different from each other, and each independently a substituted or unsubstituted aryl group having 6 to 30 carbon atoms; a substituted or unsubstituted alkyl group having 1 to 30 carbon atoms; or a substituted or unsubstituted heteroaryl group having 2 to 30 carbon atoms.

According to one embodiment of the present specification, Ar2 and Ar3 are the same as or different from each other, and each independently a substituted or unsubstituted aryl group having 6 to 30 carbon atoms, or a substituted or unsubstituted heteroaryl group having 2 to 30 carbon atoms.

In one embodiment of the present specification, Ar2 and Ar3 are the same as or different from each other, and each independently an aryl group having 6 to 30 carbon atoms unsubstituted or substituted with a germanium group; or a heteroaryl group having 2 to 30 carbon atoms unsubstituted or substituted with a germanium group.

In one embodiment of the present specification, Ar2 and Ar3 are the same as or different from each other, and each independently a phenyl group unsubstituted or substituted with a germanium group.

In one embodiment of the present specification, Ar2 and Ar3 are the same as or different from each other, and each independently a phenyl group unsubstituted or substituted with a trimethylgermanium group.

In one embodiment of the present disclosure, Chemical Formula A-1 may be the following compound.

In one embodiment, the organic material layer includes a light emitting layer, and the light emitting layer includes a compound represented by the following Chemical Formula A-2.

[Chemical Formula A-2]

In Chemical Formula A-2,

Ar4 and Ar5 are the same as or different from each other, and each independently a substituted or unsubstituted monocyclic aryl group; or a substituted or unsubstituted multicyclic aryl group, G1 to G8 are the same as or different from each other, and each independently hydrogen; a silyl group; a halogen group; a cyano group; a substituted or unsubstituted monocyclic aryl group; a substituted or unsubstituted multicyclic aryl group; a substituted or unsubstituted alkyl group; a substituted or unsubstituted cycloalkyl group; or a substituted or unsubstituted alkoxy group.

In one embodiment, the organic material layer includes a light emitting layer, and the light emitting layer includes the compound represented by Chemical Formula A-2 as a host of the light emitting layer.

In one embodiment of the present disclosure, Ar4 and Ar5 are the same as or different from each other, and each independently a substituted or unsubstituted multicyclic aryl group.

In one embodiment, Ar4 and Ar5 are the same as or different from each other, and each independently a substituted or unsubstituted naphthyl group.

In one embodiment of the present disclosure, Ar4 and Ar5 are the same as or different from each other, and each independently a substituted or unsubstituted 2-naphthyl group; or a substituted or unsubstituted 1-naphthyl group.

According to one embodiment, Ar4 and Ar5 are a 2-naphthyl group.

In one embodiment, G1 to G8 are the same as or different from each other, and each independently hydrogen; or a substituted or unsubstituted alkyl group.

According to one embodiment, G1 to G8 are the same as or different from each other, and each independently hydrogen; or a substituted or unsubstituted alkyl group having 1 to 10 carbon atoms.

In one embodiment of the present disclosure, G1 to G8 are the same as or different from each other, and each independently hydrogen; a methyl group, an ethyl group, a propyl group, an isopropyl group or a butyl group.

In one embodiment, G1 to G8 are the same as or different from each other, and each independently hydrogen; or a methyl group.

In one embodiment of the present disclosure, Chemical Formula A-2 may be the following compound.

In one embodiment, the organic material layer includes a light emitting layer, and the light emitting layer may include the compound represented by Chemical Formula A-1 as a dopant of the light emitting layer, and may include the compound represented by Chemical Formula A-2 as a host of the light emitting layer.

According to one embodiment, the organic light emitting device may be an organic light emitting device having a structure of consecutively laminating an anode, one or more organic material layers and a cathode on a substrate (normal type). According to another embodiment, the organic light emitting device may be an organic light emitting device having a reverse structure of consecutively laminating a cathode, one or more organic material layers and an anode on a substrate (inverted type).

The organic light emitting device of the present specification may be manufactured using materials and methods known in the art, except that one or more layers of the organic material layers include the compound of Chemical Formula 1, that is, the compound represented by Chemical Formula 1.

For example, the organic light emitting device according to the present specification may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, the compound of Chemical Formula 1 may be formed into the organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may be manufactured by consecutively depositing a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

The organic light emitting device may have, for example, a laminated structure as below, however, the structure is not limited thereto.

(1) Anode/hole transfer layer/light emitting layer/cathode
(2) Anode/hole injection layer/hole transfer layer/light emitting layer/cathode
(3) Anode/hole injection layer/hole buffer layer/hole transfer layer/light emitting layer/cathode
(4) Anode/hole transfer layer/light emitting layer/electron transfer layer/cathode
(5) Anode/hole transfer layer/light emitting layer/electron transfer layer/electron injection layer/cathode
(6) Anode/hole injection layer/hole transfer layer/light emitting layer/electron transfer layer/cathode
(7) Anode/hole injection layer/hole transfer layer/light emitting layer/electron transfer layer/electron injection layer/cathode
(8) Anode/hole injection layer/hole buffer layer/hole transfer layer/light emitting layer/electron transfer layer/cathode
(9) Anode/hole injection layer/hole buffer layer/hole transfer layer/light emitting layer/electron transfer layer/electron injection layer/cathode
(10) Anode/hole transfer layer/electron blocking layer/light emitting layer/electron transfer layer/cathode
(11) Anode/hole transfer layer/electron blocking layer/light emitting layer/electron transfer layer/electron injection layer/cathode
(12) Anode/hole injection layer/hole transfer layer/electron blocking layer/light emitting layer/electron transfer layer/cathode
(13) Anode/hole injection layer/hole transfer layer/electron blocking layer/light emitting layer/electron transfer layer/electron injection layer/cathode
(14) Anode/hole transfer layer/light emitting layer/hole blocking layer/electron transfer layer/cathode
(15) Anode/hole transfer layer/light emitting layer/hole blocking layer/electron transfer layer/electron injection layer/cathode
(16) Anode/hole injection layer/hole transfer layer/light emitting layer/hole blocking layer/electron transfer layer/cathode
(17) Anode/hole injection layer/hole transfer layer/light emitting layer/hole blocking layer/electron transfer layer/electron injection layer/cathode For example, structures of an organic light emitting device according to one embodiment of the present specification are illustrated in FIG. 1 and FIG. 2.

FIG. 1 illustrates an organic light emitting device formed with a substrate (1), an anode (2), a hole transfer layer (6), a light emitting layer (3) and a cathode (4). In such a structure, the compound may be included in the hole transfer layer.

FIG. 2 illustrates an organic light emitting device formed with a substrate (1), an anode (2), a hole injection layer (5), a hole transfer layer (6), a light emitting layer (3), an electron transfer layer (8) and a cathode (4). In such a structure, the compound may be included in the hole injection layer or the hole transfer layer.

The anode (2) is an electrode injecting holes, and may be any one of indium tin oxide (ITO), indium zinc oxide (IZO) or zinc oxide (ZnO) having large work function. In addition, when the anode (2) is a reflective electrode, the anode (2) may further include a reflective layer formed with any one of aluminum (Al), silver (Ag) or nickel (Ni) below the layer formed with any one of ITO, IZO or ZnO.

The hole injection layer (5) may perform a role of smoothly injecting holes from the anode (2) to the light emitting layer (3). The hole injection layer (5) may include the compound of Chemical Formula 1. In this case, the hole injection layer (5) may be formed only with the compound of Chemical Formula 1, however, the compound of Chemical Formula 1 may be present as being mixed or doped to other hole injection layer materials known in the art. The compound of Chemical Formula 1 may occupy 100% of the hole injection layer, but may also be doped in 0.1% by weight to 50% by weight. The compound of Chemical Formula 1 is a derivative having an indenofluorene structure, and has excellent electron accepting ability, and therefore, is capable of improving power consumption and lowering driving voltage. The hole injection layer (5) may have a thickness of 1 nm to 150 nm. Herein, the hole injection layer (5) having a thickness of 1 nm or greater has an advantage of preventing the decline of hole injection properties, and when the thickness is 150 nm or less, the thickness of the hole injection layer (5) is too high, which has an advantage of preventing an increase in the driving voltage for enhancing hole migration. As other hole injection layer materials, hole injection materials known in the art may be used. For example, any one or more selected from the group consisting of cupper phthalocyanine (CuPc), poly(3,4)-ethylenedioxythiophene (PEDOT), polyaniline (PANI) and N,N-dinaphthyl-N,N'-diphenyl benzidine (NPD) may be used as the hole injection layer material, however, the material is not limited thereto.

The hole transfer layer (6) may perform a role of smoothly transferring holes. The hole transfer layer (6) may include the compound of Chemical Formula 1. In this case, the hole transfer layer (6) may be formed only with the compound of Chemical Formula 1, however, the compound of Chemical Formula 1 may be present as being mixed or doped to other hole transfer layer materials known in the art. The compound of Chemical Formula 1 may occupy 100% of the hole transfer layer, but may also be doped in 0.1% by weight to 50% by weight. As other hole transfer layer materials, hole transfer materials known in the art may be used. For example, the hole transfer layer (6) may be formed with any one or more selected from the group consisting of N,N-dinaphthyl-N,N'-diphenylbenzidine (NPD), N,N'-bis-(3-methylphenyl)-N,N'-bis-(phenyl)-benzidine (TPD), s-TAD and 4,4',4"-tris(N-3-methylphenyl-N-phenyl-amino)-triphenylamine (MTDATA), however, the material is not limited thereto. Examples of the hole transfer layer material may include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane-based, aniline-based copolymers, conductive polymer oligomers (particularly thiophene oligomers), and the like.

A hole buffer layer may be additionally provided between the hole injection layer and the hole transfer layer. The hole buffer layer may include the compound of Chemical Formula 1, and may include other hole injection or transfer materials known in the art. When the hole buffer layer includes the compound of Chemical Formula 1, the hole buffer layer may be formed only with the compound of Chemical Formula 1 as well, but may also be formed with the compound of Chemical Formula 1 being mixed or doped to other host materials.

An electron blocking layer may be provided between the hole transfer layer and the light emitting layer, and the compound of Chemical Formula 1 or materials known in the art may be used.

The light emitting layer (3) may emit red, green and/or blue light, and may be formed with phosphorescent materials or fluorescent materials. As the light emitting layer material, materials known in the art may be used. As the light emitting host material, carbazole biphenyl (CBP) or 1,3-bis(carbazol-9-yl) (mCP) may be used, however, the material is not limited thereto.

When the light emitting layer (3) emits red light, phosphorescent materials such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr) and octaethylporphyrin platinum (PtOEP), or fluorescent materials such as tris(8-hydroxyquinolino)aluminum ($Alq_3$) may be used as the light emitting dopant, however, the material is not limited thereto. When the light emitting layer (3) emits green light, phosphorescent materials such as fac tris(2-phenylpyridine)iridium ($Ir(ppy)_3$), or fluorescent materials such as tris(8-hydroxyquinolino)aluminum ($Alq_3$) may be used as the light emitting dopant, however, the material is not limited thereto. When the light emitting layer (3) emits blue light, phosphorescent materials such as $(4,6-F_2ppy)_2Irpic$, or fluorescent materials such as spiro-DPVBi, spiro-6P, distyrylbenzene (DSB), distyrylarylene (DSA), PFO-based polymers and PPV-based polymers may be used as the light emitting dopant, however, the material is not limited thereto.

A hole blocking layer may be provided between the electron transfer layer and the light emitting layer, and materials known in the art may be used.

The electron transfer layer (8) may perform a role of smoothly transferring electrons. Materials known in the art such as tris(8-hydroxyquinolino)aluminum ($Alq_3$), PBD, TAZ, spiro-PBD, BAlq and SAlq may be used. The electron transfer layer (8) may have a thickness of 1 nm to 50 nm. Herein, the electron transfer layer (8) having a thickness of 1 nm or greater has an advantage of preventing the decline of electron transfer properties, and when the thickness is 50 nm or less, the thickness of the electron transfer layer (8) is too high, which has an advantage of preventing an increase in the driving voltage for enhancing electron migration.

The electron injection layer may perform a role of smoothly injecting electrons. The electron injection layer may be formed with organic substances, complexes or metal compounds known in the art such as tris(8-hydroxyquinolino)aluminum ($Alq_3$), PBD, TAZ, spiro-PBD, BAlq or SAlq. As the metal compound, metal halides may be used, and examples thereof may include LiQ, LiF, NaF, KF, RbF, CsF, FrF, $BeF_2$, $MgF_2$, $CaF_2$, $SrF_2$, $BaF_2$, $RaF_2$ and the like. The electron injection layer may have a thickness of 1 nm to 50 nm. Herein, the electron injection layer having a thickness of 1 nm or greater has an advantage of preventing the decline of electron injection properties, and when the thickness is 50 nm or less, the thickness of the electron injection layer is too high, which has an advantage of preventing an increase in the driving voltage for enhancing electron migration.

The cathode (4) is an electrode injecting electrons, and may be formed with magnesium (Mg), calcium (Ca), aluminum (Al), silver (Ag) having small work function, or alloys thereof. Herein, the cathode (4) may be formed to a thickness small enough to transmit light when an organic electroluminescent device has a top-emission or dual-emission structure, and when an organic electroluminescent device has a bottom-emission structure, the cathode may be formed to a thickness large enough to reflect light.

According to another embodiment, the organic material layer includes two or more light emitting layers, and may include a charge generation layer including the compound of Chemical Formula 1 provided between the two layers of the light emitting layers. Herein, an organic light emitting device emitting white light may be manufactured by having one of the light emitting layer emit blue light, and the other emit yellow light. One or more organic material layers such as the hole injection layer, the hole buffer layer, the hole transfer layer, the electron blocking layer, the hole blocking layer, the electron transfer layer and the electron injection layer described above may be further included between the light emitting layer and the anode or the cathode, or between the light emitting layer and the charge generation layer. FIG. 3 illustrates an an organic light emitting device including a substrate (1), an anode (2) and a cathode (4), and including two units including a hole injection layer (5a, 5b), a hole transfer layer (6a, 6b), a light emitting layer (3a, 3b) and an electron transfer layer (8a, 8b) between the anode and the cathode, and provided with a charge generation layer (9) between the units.

The organic light emitting device according to the present specification may be a top-emission type, a bottom-emission type or a dual-emission type depending on the materials used.

In one embodiment of the present specification, the compound of Chemical Formula 1 may be included in an organic solar cell or an organic transistor in addition to an organic light emitting device.

Preparation of the compound represented by Chemical Formula 1, and manufacture of the organic light emitting device including the same will be specifically described with reference to the following examples. However, the following examples are for illustrative purposes only, and the scope of the present specification is not limited thereto.

Synthesis of Intermediate A

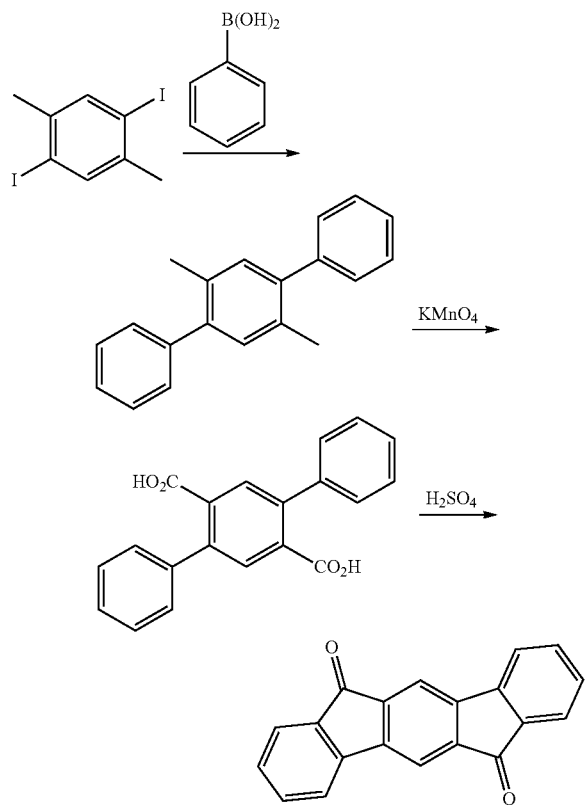

10.0 g of 1,4-diiodo-2,5-dimethylbenzene was mixed with 7.8 g of phenylboronic acid, 1.4 g of tetrakis(triphenylphosphine)palladium(0), 80 ml of 2 M sodium carbonate, 40 ml of ethanol and 80 ml of toluene, and the result was stirred under reflux for 8 hours under nitrogen atmosphere. After cooling the result, the reaction solution was filtered, washed with water and ethanol, and then separated additionally using a silica gel column (developing solvent: methylene chloride) to obtain 6.8 g of white solid. When measuring a mass spectrum of the obtained white solid, a peak at M/Z=258 was identified.

Next, 6.8 g of this white solid was mixed with 20.0 g of potassium permanganate, 24 ml of pyridine and 40 ml of water, and the result was stirred for 8 hours at 100° C. After that, a mixture of 20.0 g of potassium permanganate, 24 ml of pyridine and 40 ml of water was additionally introduced thereto, and the result was stirred for 4 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 4.0 g of white solid.

Next, this white solid was added to 40 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 3.8 g. When measuring a mass spectrum of the obtained solid, a peak at M/Z=282 was identified.

Synthesis of Compound A-1

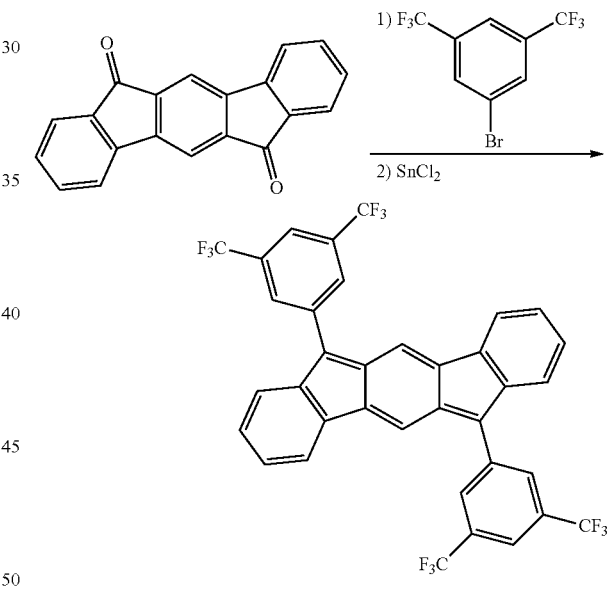

After dissolving 5.6 g of 1-bromo-3,5-bis(trifluoromethyl)benzene in 40 ml of tetrahydrofuran, the result was cooled to −78° C. under nitrogen atmosphere. 7.1 ml of n-BuLi (2.5 M hexane solution) was dropped thereto, and the result was stirred for 20 minutes at −78° C. Meanwhile, in another flask prepared, 1 g of Intermediate A was dissolved in 120 ml of tetrahydrofuran, and the result was cooled to −78° C. The produced lithium anions of the 1-bromo-3,5-bis(trifluoromethyl)benzene were introduced to the Intermediate A solution through cannulation, the temperature was raised to room temperature, and the result was stirred for 2 hours. After that, the result was separated with dilute hydrochloric acid and ethyl acetate, dried with anhydrous sodium sulfate, and filtered. After vacuum distilling the ethyl acetate, the result was dissolved again in 100 ml of toluene, 2 g of tin chloride and trifluoroacetic acid (0.4 ml) were introduced thereto, and the result was stirred for 12 hours at 50° C. After that, the result was filtered to remove the solid, vacuum distilled and then recrystallized with methanol to obtain 0.88 g of solid A-1. When measuring a mass spectrum of the obtained solid, a peak at M/Z=676 was identified.

Synthesis of Compound A-2

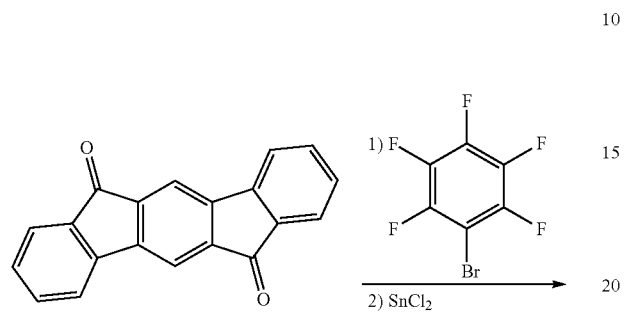

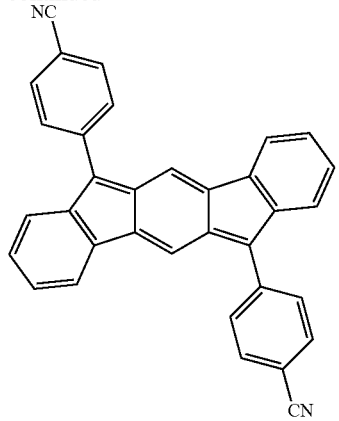

Reaction and purification were carried out in the same manner as in the synthesis of Compound A-1 except that 5.6 g of 1-bromo-3,5-bis(trifluoromethyl)benzene was changed to 3.5 g of 1-bromo-4-cyanobenzene to obtain 1.0 g of solid. When measuring a mass spectrum of the obtained solid, a peak at M/Z=454 was identified.

Synthesis of Intermediate B

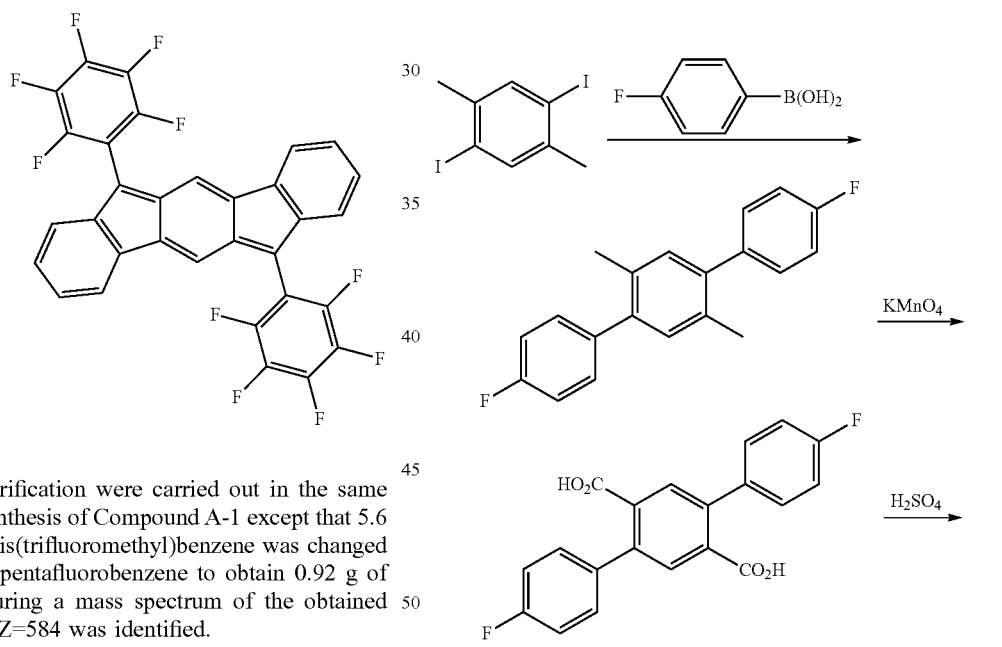

Reaction and purification were carried out in the same manner as in the synthesis of Compound A-1 except that 5.6 g of 1-bromo-3,5-bis(trifluoromethyl)benzene was changed to 4.7 g of bromo-pentafluorobenzene to obtain 0.92 g of solid. When measuring a mass spectrum of the obtained solid, a peak at M/Z=584 was identified.

Synthesis of Compound A-3

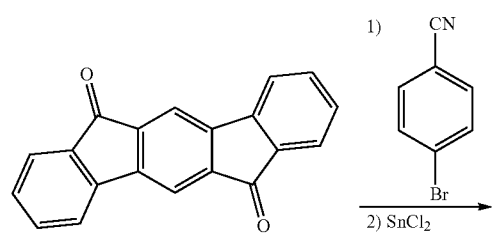

Synthesis and purification were carried out in the same manner as in the synthesis of Intermediate A except that 8.9 g of 4-fluorophenylboronic acid was used instead of 7.8 g of phenylboronic acid to obtain 7.2 g of white solid. When measuring a mass spectrum of the obtained white solid, a peak at M/Z=294 was identified.

Next, 7.2 g of this white solid was mixed with 20.0 g of potassium permanganate, 24 ml of pyridine and 40 ml of water, and the result was stirred for 8 hours at 100° C. After that, a mixture of 20.0 g of potassium permanganate, 24 ml of pyridine and 40 ml of water was additionally introduced thereto, and the result was stirred for 4 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 4.8 g of white solid.

Next, this white solid was added to 40 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 4.2 g. When measuring a mass spectrum of the obtained solid, a peak at M/Z=318 was identified.

Synthesis of Compound A-4

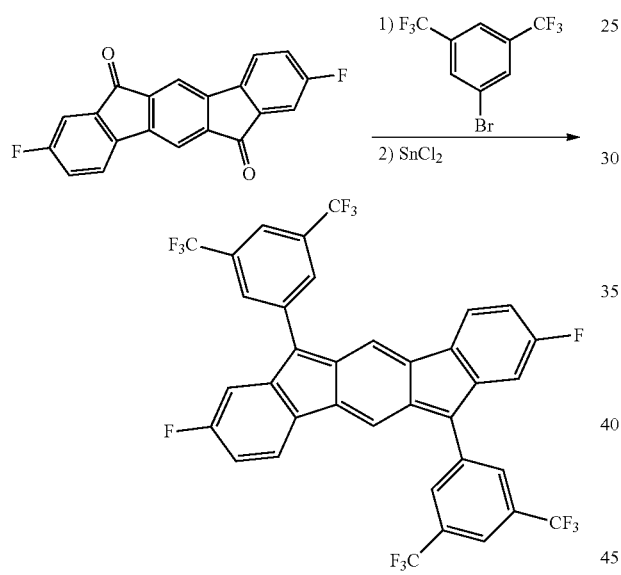

Reaction and purification were carried out in the same manner as in the synthesis of Compound A-1 except that 1 g of Intermediate A was changed to 1.1 g of Intermediate B to obtain 1.0 g of solid. When measuring a mass spectrum of the obtained solid, a peak at M/Z=712 was identified.

Synthesis of Compound A-5

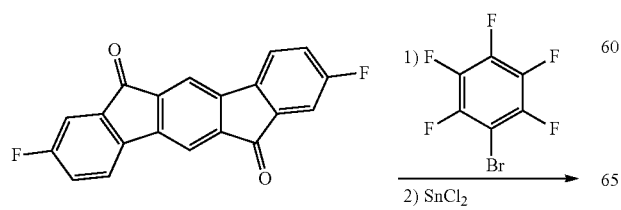

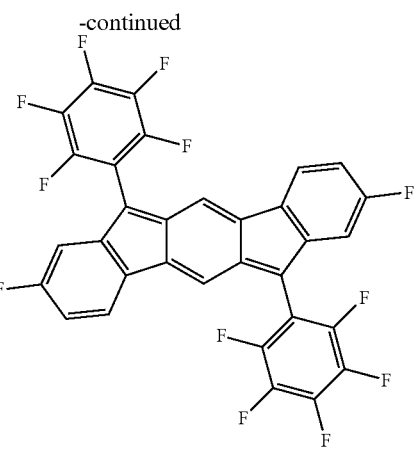

Reaction and purification were carried out in the same manner as in the synthesis of Compound A-2 except that 1 g of Intermediate A was changed to 1.1 g of Intermediate B to obtain 1.2 g of solid. When measuring a mass spectrum of the obtained solid, a peak at M/Z=620 was identified.

Synthesis of Compound A-6

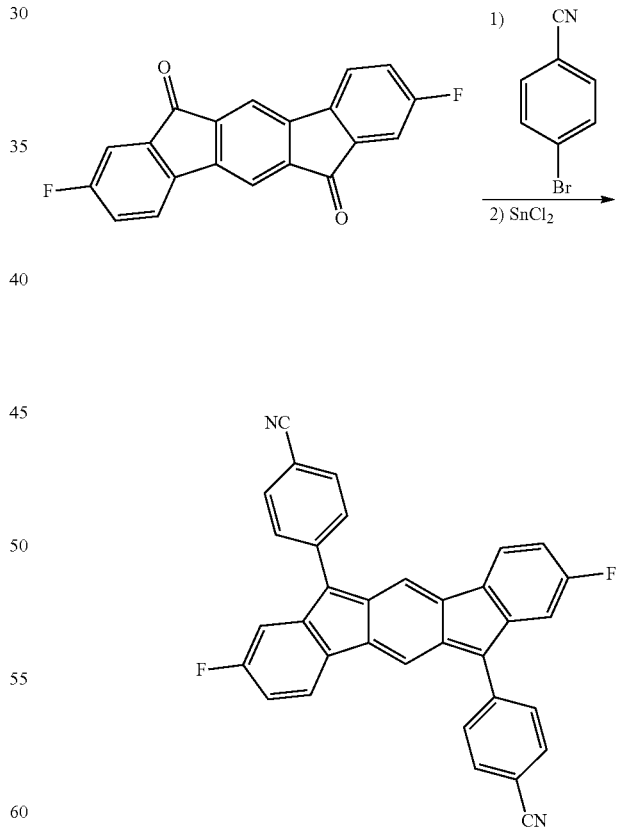

Reaction and purification were carried out in the same manner as in the synthesis of Compound A-3 except that 1 g of Intermediate A was changed to 1.1 g of Intermediate B to obtain 0.8 g of solid. When measuring a mass spectrum of the obtained solid, a peak at M/Z=490 was identified.

Synthesis of Intermediate C

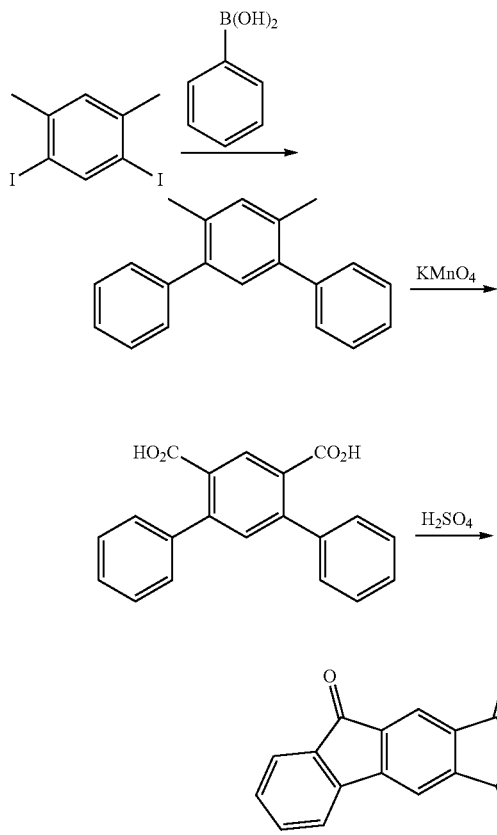

10.0 g of 1,5-diiodo-2,4-dimethylbenzene was mixed with 7.8 g of phenylboronic acid, 1.4 g of tetrakis(triphenylphosphine)palladium(0), 80 ml of 2 M sodium carbonate, 40 ml of ethanol and 80 ml of toluene, and the result was stirred under reflux for 10 hours under nitrogen atmosphere. 7.4 g of white solid was obtained by separating and purifying the result in the same manner as in the synthesis of Intermediate A. When measuring a mass spectrum of the obtained white solid, a peak at M/Z=258 was identified.

Next, 7.4 g of this white solid was mixed with 20.0 g of potassium permanganate, 24 ml of pyridine and 40 ml of water, and the result was stirred for 8 hours at 100° C. After that, a mixture of 20.0 g of potassium permanganate, 24 ml of pyridine and 40 ml of water was additionally introduced thereto, and the result was stirred for 4 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 5.0 g of white solid.

Next, this white solid was added to 40 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 4.0 g. When measuring a mass spectrum of the obtained solid, a peak at M/Z=282 was identified.

Synthesis of Compound A-7

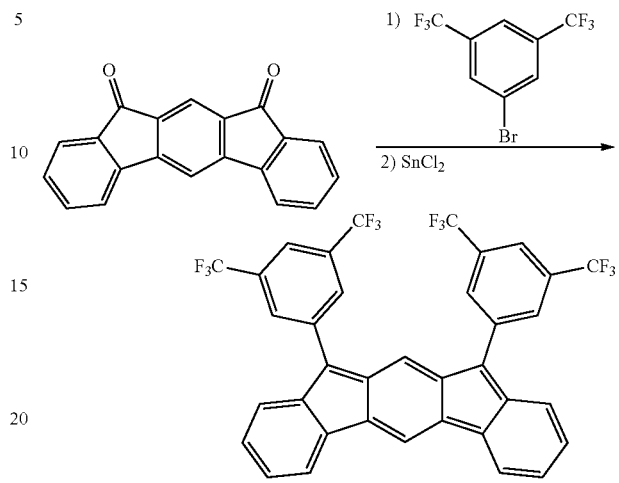

Reaction and purification were carried out in the same manner as in the synthesis of Compound A-1 except that 1 g of Intermediate A was changed to 1.0 g of Intermediate C to obtain 0.6 g of solid. When measuring a mass spectrum of the obtained solid, a peak at M/Z=676 was identified.

Synthesis of Compound A-8

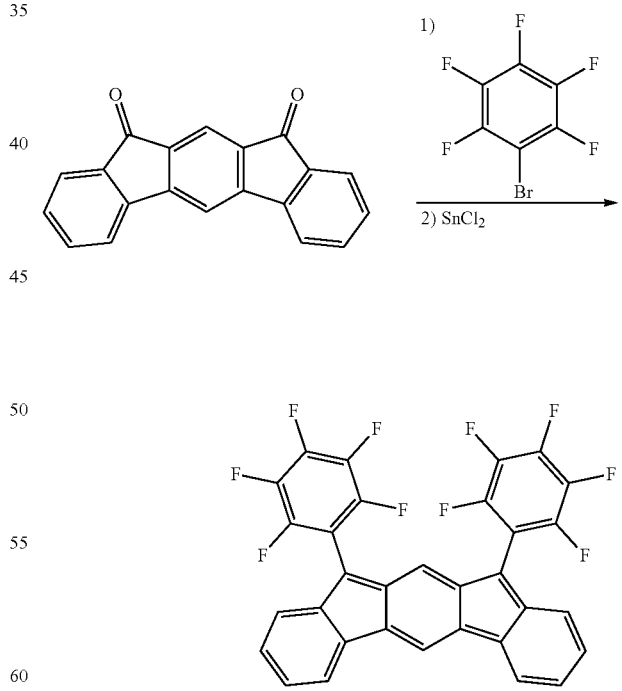

Reaction and purification were carried out in the same manner as in the synthesis of Compound A-2 except that 1 g of Intermediate A was changed to 1.0 g of Intermediate C to obtain 0.5 g of solid. When measuring a mass spectrum of the obtained solid, a peak at M/Z=584 was identified.

Synthesis of Compound A-9

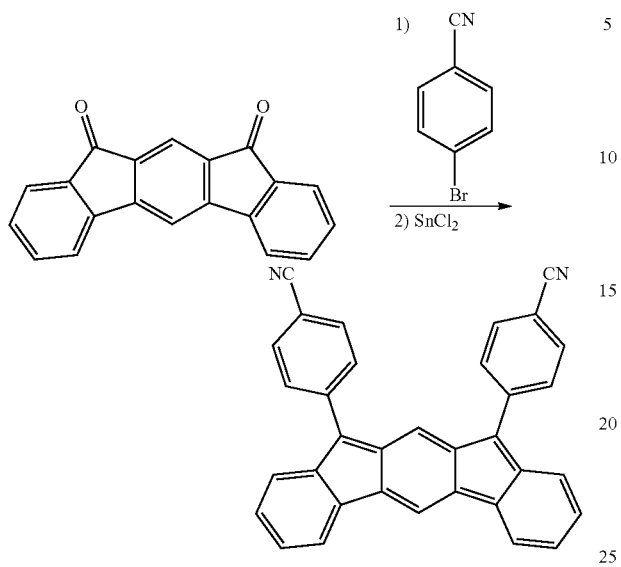

Reaction and purification were carried out in the same manner as in the synthesis of Compound A-3 except that 1 g of Intermediate A was changed to 1.0 g of Intermediate C to obtain 0.4 g of solid. When measuring a mass spectrum of the obtained solid, a peak at M/Z=454 was identified.

Synthesis of Intermediate D

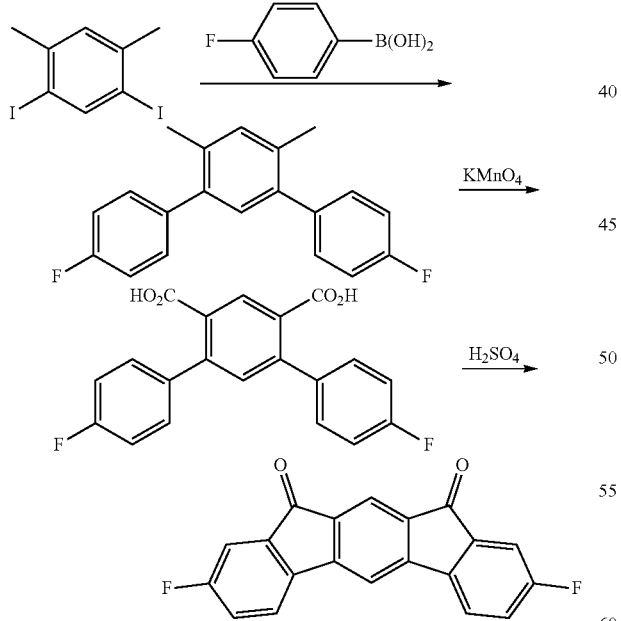

Synthesis and purification were carried out in the same manner as in the synthesis of Intermediate C except that 8.9 g of 4-fluorophenylboronic acid was used instead of 7.8 g of phenylboronic acid to obtain 7.6 g of white solid. When measuring a mass spectrum of the obtained white solid, a peak at M/Z=294 was identified.

Next, 7.6 g of this white solid was mixed with 20.0 g of potassium permanganate, 24 ml of pyridine and 40 ml of water, and the result was stirred for 8 hours at 100° C. After that, a mixture of 20.0 g of potassium permanganate, 24 ml of pyridine and 40 ml of water was additionally introduced thereto, and the result was stirred for 4 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 4.8 g of white solid.

Next, this white solid was added to 40 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 4.4 g. When measuring a mass spectrum of the obtained solid, a peak at M/Z=318 was identified.

Synthesis of Compound A-10

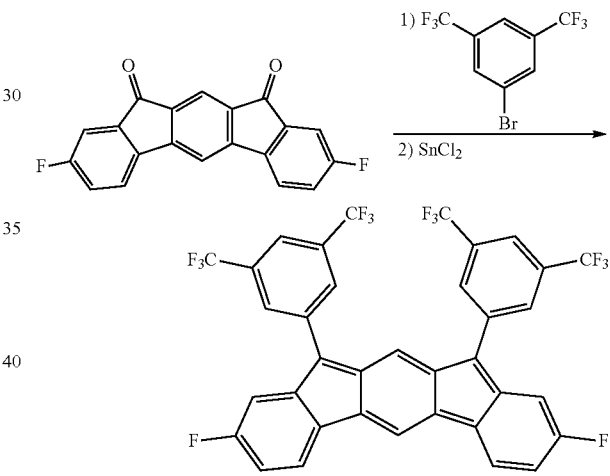

Reaction and purification were carried out in the same manner as in the synthesis of Compound A-7 except that 1 g of Intermediate C was changed to 1.1 g of Intermediate D to obtain 0.5 g of solid. When measuring a mass spectrum of the obtained solid, a peak at M/Z=712 was identified.

Synthesis of Compound A-11

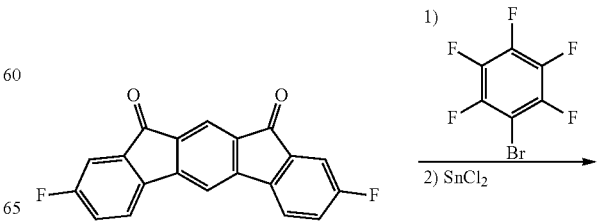

-continued

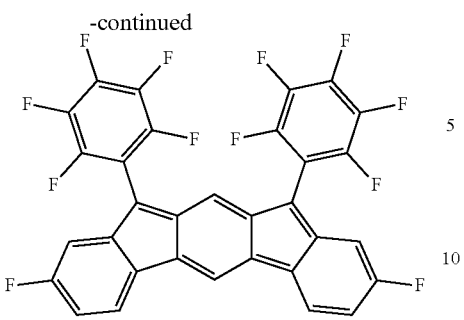

Reaction and purification were carried out in the same manner as in the synthesis of Compound A-2 except that 1 g of Intermediate A was changed to 1.1 g of Intermediate D to obtain 0.6 g of solid. When measuring a mass spectrum of the obtained solid, a peak at M/Z=620 was identified.

Synthesis of Compound A-12

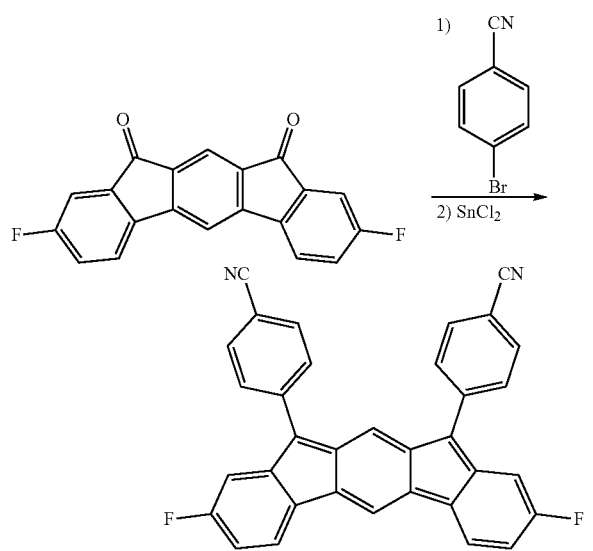

Reaction and purification were carried out in the same manner as in the synthesis of Compound A-3 except that 1 g of Intermediate A was changed to 1.1 g of Intermediate D to obtain 0.3 g of solid. When measuring a mass spectrum of the obtained solid, a peak at M/Z=491 was identified.

Synthesis of Intermediate E

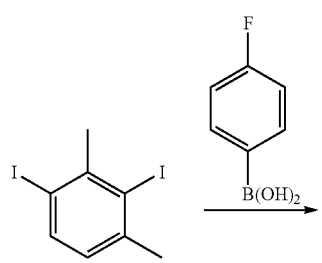

-continued

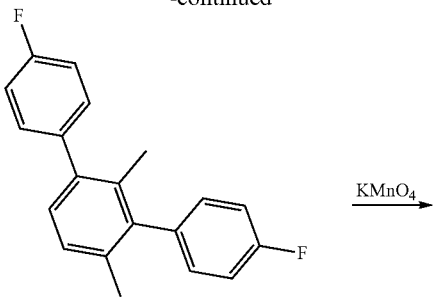

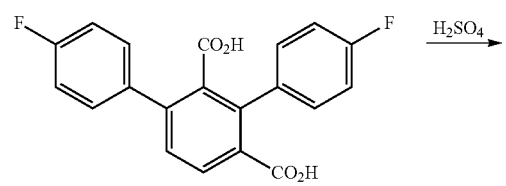

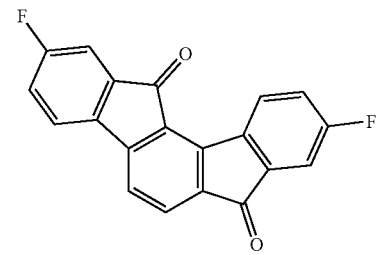

10.0 g of 1,3-diiodo-2,4-dimethylbenzene was mixed with 8.9 g of 4-fluorophenylboronic acid, 1.4 g of tetrakis(triphenylphosphine)palladium(0), 80 ml of 2 M sodium carbonate, 40 ml of ethanol and 80 ml of toluene, and the result was stirred under reflux for 12 hours under nitrogen atmosphere. 8.6 g of white solid was obtained by separating and purifying the result in the same manner as in the synthesis of Intermediate A. When measuring a mass spectrum of the obtained white solid, a peak at M/Z=294 was identified.

Next, 8.6 g of of this white solid was mixed with 23.0 g of potassium permanganate, 28 ml of pyridine and 50 ml of water, and the result was stirred for 8 hours at 100° C. After that, a mixture of 23.0 g of potassium permanganate, 28 ml of pyridine and 50 ml of water was additionally introduced thereto, and the result was stirred for 4 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 2.8 g of white solid.

Next, this white solid was added to 40 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 1.4 g. When measuring a mass spectrum of the obtained solid, a peak at M/Z=318 was identified.

Synthesis of Compound A-13

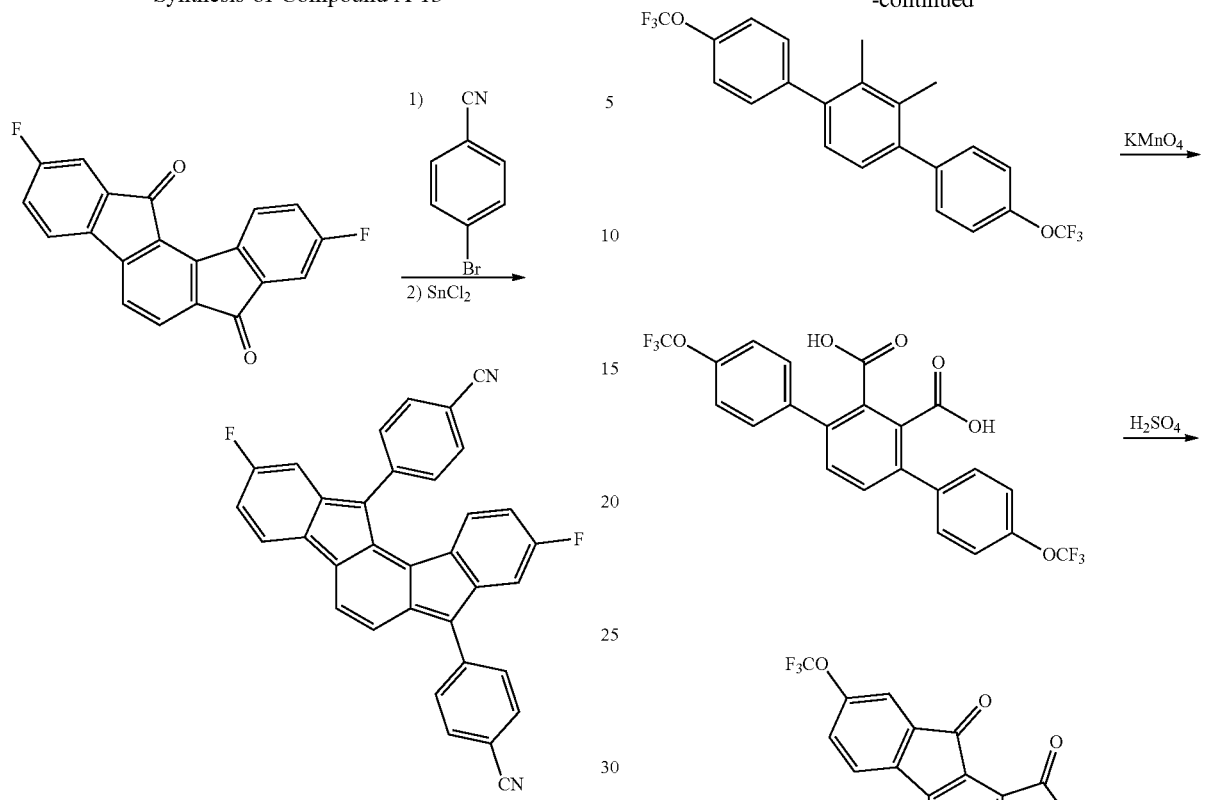

After dissolving 10.4 g of 4-bromobenzonitrile in 120 ml of tetrahydrofuran, the result was cooled to −78° C. under nitrogen atmosphere. 21.3 ml of n-BuLi (2.5 M hexane solution) was dropped thereto, and the result was stirred for 30 minutes at −78° C. Meanwhile, in another flask prepared, 3 g of Intermediate E was dissolved in 360 ml of tetrahydrofuran, and the result was cooled to −78° C. The produced lithium anions of the 4-bromobenzonitrile were introduced to the Intermediate A solution through cannulation, the temperature was raised to room temperature, and the result was stirred for 2 hours. After that, the result was separated with dilute hydrochloric acid and ethyl acetate, dried with anhydrous sodium sulfate, and filtered. After vacuum distilling the ethyl acetate, the result was dissolved again in 300 ml of toluene, 6 g of tin chloride and trifluoroacetic acid (1.2 ml) were introduced thereto, and the result was stirred for 12 hours at 50° C. After that, the result was filtered to remove the solid, vacuum distilled and then recrystallized with methanol to obtain 0.68 g of solid A-13. When measuring a mass spectrum of the obtained solid, a peak at M/Z=491 was identified.

Synthesis of Intermediate F

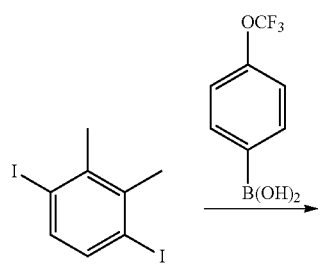

10.0 g of 1,4-diiodo-2,3-dimethylbenzene was mixed with 12.8 g of 4-trifluoromethoxyphenylboronic acid, 1.4 g of tetrakis(triphenylphosphine)palladium(0), 80 ml of 2 M sodium carbonate, 40 ml of ethanol and 80 ml of toluene, and the result was stirred under reflux for 12 hours under nitrogen atmosphere. 9.8 g of white solid was obtained by separating and purifying the result in the same manner as in the synthesis of Intermediate A. When measuring a mass spectrum of the obtained white solid, a peak at M/Z=426 was identified.

Next, 9.8 g of this white solid was mixed with 24.0 g of potassium permanganate, 30 ml of pyridine and 60 ml of water, and the result was stirred for 8 hours at 100° C. After that, a mixture of 24.0 g of potassium permanganate, 30 ml of pyridine and 60 ml of water was additionally introduced thereto, and the result was stirred for 4 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 3.8 g of white solid.

Next, this white solid was added to 48 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 1.6 g. When measuring a mass spectrum of the obtained solid, a peak at M/Z=450 was identified.

Synthesis of Compound A-14

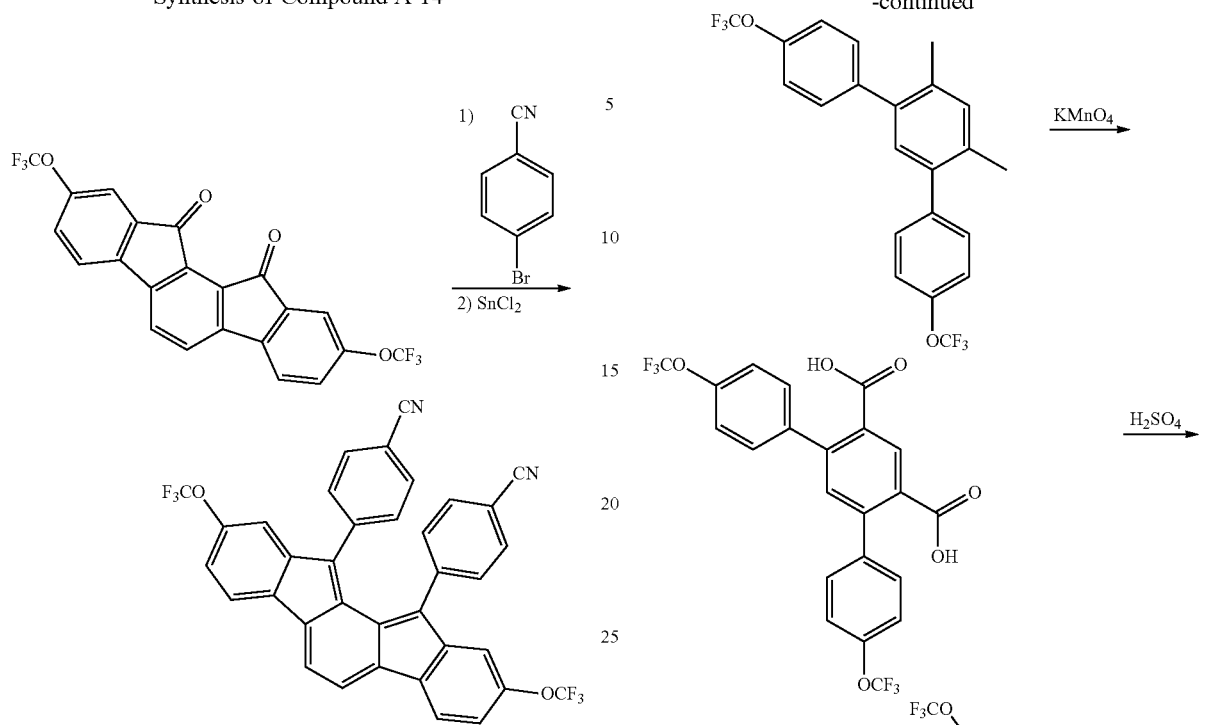

After dissolving 10.4 g of 4-bromobenzonitrile in 120 ml of tetrahydrofuran, the result was cooled to −78° C. under nitrogen atmosphere. 21.3 ml of n-BuLi (2.5 M hexane solution) was dropped thereto, and the result was stirred for 30 minutes at −78° C. Meanwhile, in another flask prepared, 3 g of Intermediate F was dissolved in 360 ml of tetrahydrofuran, and the result was cooled to −78° C. The produced lithium anions of the 4-bromobenzonitrile were introduced to the Intermediate A solution through cannulation, the temperature was raised to room temperature, and the result was stirred for 2 hours. After that, the result was separated with dilute hydrochloric acid and ethyl acetate, dried with anhydrous sodium sulfate, and filtered. After vacuum distilling the ethyl acetate, the result was dissolved again in 300 ml of toluene, 6 g of tin chloride and trifluoroacetic acid (1.2 ml) were introduced thereto, and the result was stirred for 12 hours at 50° C. After that, the result was filtered to remove the solid, vacuum distilled and then recrystallized with methanol to obtain 0.58 g of solid A-14. When measuring a mass spectrum of the obtained solid, a peak at M/Z=622 was identified.

Synthesis of Intermediate G

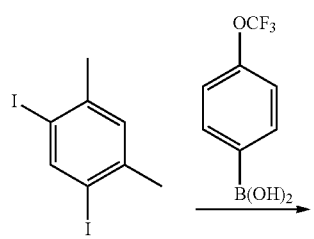

10.0 g of 1,5-diiodo-2,4-dimethylbenzene was mixed with 12.8 g of 4-trifluoromethoxyphenylboronic acid, 1.4 g of tetrakis(triphenylphosphine)palladium(0), 80 ml of 2 M sodium carbonate, 40 ml of ethanol and 80 ml of toluene, and the result was stirred under reflux for 12 hours under nitrogen atmosphere. 6.6 g of white solid was obtained by separating and purifying the result in the same manner as in the synthesis of Intermediate A. When measuring a mass spectrum of the obtained white solid, a peak at M/Z=426 was identified.

Next, 6.6 g of this white solid was mixed with 20.0 g of potassium permanganate, 25 ml of pyridine and 50 ml of water, and the result was stirred for 8 hours at 100° C. After that, a mixture of 20.0 g of potassium permanganate, 25 ml of pyridine and 50 ml of water was additionally introduced thereto, and the result was stirred for 8 hours. After that, the result was filtered to remove the solid, and the filtrate was neutralized by dropping 1 N hydrochloric acid thereto. Precipitated white solid was filtered, washed with dilute hydrochloric acid and ion exchange water, and then dried to obtain 4.2 g of white solid.

Next, this white solid was added to 48 ml of concentrated sulfuric acid, and the result was heated and stirred for 12 hours at 50° C. After that, the result was cooled to room temperature, and the reactant was introduced to ice water. Orange solid was filtered, washed with ion exchange water, and then dried to obtain 1.4 g. When measuring a mass spectrum of the obtained solid, a peak at M/Z=450 was identified.

Synthesis of Compound A-15

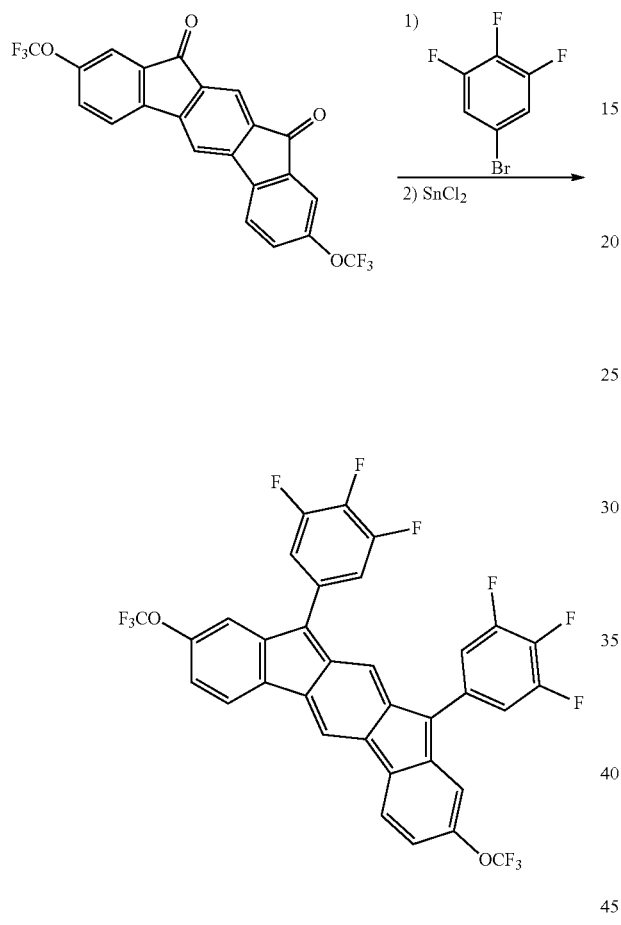

After dissolving 12.9 g of 5-bromo-1,2,3-trifluorobenzene in 140 ml of tetrahydrofuran, the result was cooled to −78° C. under nitrogen atmosphere. 21.3 ml of n-BuLi (2.5 M hexane solution) was dropped thereto, and the result was stirred for 30 minutes at −78° C. Meanwhile, in another flask prepared, 3 g of Intermediate G was dissolved in 360 ml of tetrahydrofuran, and the result was cooled to −78° C. The produced lithium anions of the 5-bromo-1,2,3-trifluorobenzene were introduced to the Intermediate G solution through cannulation, the temperature was raised to room temperature, and the result was stirred for 2 hours. After that, the result was separated with dilute hydrochloric acid and ethyl acetate, dried with anhydrous sodium sulfate, and filtered. After vacuum distilling the ethyl acetate, the result was dissolved again in 300 ml of toluene, 6 g of tin chloride and trifluoroacetic acid (1.2 ml) were introduced thereto, and the result was stirred for 12 hours at 50° C. After that, the result was filtered to remove the solid, vacuum distilled and then recrystallized with methanol to obtain 0.48 g of solid A-15. When measuring a mass spectrum of the obtained solid, a peak at M/Z=680 was identified.

Example of Application in Device 1—Use in Hole Injection Layer

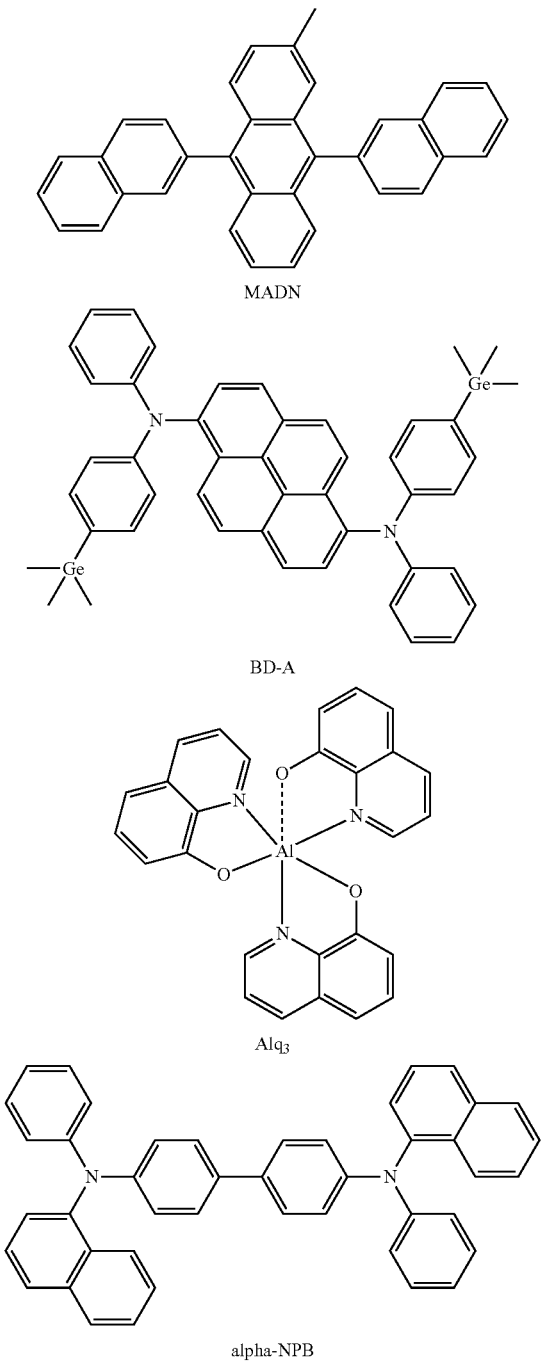

Example 1

An ITO glass was patterned so that a light emitting area became a 3 mm×3 mm size, and then cleaned. After installing the substrate in a vacuum chamber, the base pressure was set at $1×10^{-6}$ torr, and on the ITO, an anode, α-NPB was formed to a thickness of 100 Å as a hole injection layer with Compound A-1 doped in a doping concentration of 25% by weight. Subsequently, α-NPB was formed to a thickness of 600 Å as a hole transfer layer, and BD-A, a dopant, was deposited on MADN, a host, in a weight ratio of 40:2 as a light emitting layer, Alq$_3$ was formed to a thickness of 300 Å as an electron transfer layer, LiF was formed to a thickness of 10 Å as an electron injection layer, and Al was formed to a thickness of 800 Å as a cathode in this order to manufacture an organic electroluminescent device.

Example 2

An organic electroluminescent device was manufactured under the same process condition as in Example 1 described above, except that Compound A-2 was doped to the hole injection layer instead of Compound A-1.

Example 3

An organic electroluminescent device was manufactured under the same process condition as in Example 1 described above, except that Compound A-3 was doped to the hole injection layer instead of Compound A-1.

Example 4

An organic electroluminescent device was manufactured under the same process condition as in Example 1 described above, except that Compound A-4 was doped to the hole injection layer instead of Compound A-1.

Example 5

An organic electroluminescent device was manufactured under the same process condition as in Example 1 described above, except that Compound A-5 was doped to the hole injection layer instead of Compound A-1.

Example 6

An organic electroluminescent device was manufactured under the same process condition as in Example 1 described above, except that Compound A-6 was doped to the hole injection layer instead of Compound A-1.

Example 7

An organic electroluminescent device was manufactured under the same process condition as in Example 1 described above, except that Compound A-7 was doped to the hole injection layer instead of Compound A-1.

Example 8

An organic electroluminescent device was manufactured under the same process condition as in Example 1 described above, except that Compound A-8 was doped to the hole injection layer instead of Compound A-1.

Example 9

An organic electroluminescent device was manufactured under the same process condition as in Example 1 described above, except that Compound A-9 was doped to the hole injection layer instead of Compound A-1.

Comparative Example 1

An organic electroluminescent device was manufactured under the same process condition as in Example 1 described above, except that HAT-CN was doped to the hole injection layer instead of Compound A-1.

Comparative Example 2

An organic electroluminescent device was manufactured under the same process condition as in Example 1 described above, except that the hole injection layer was famed without any doping.

Comparative Example 3

An organic electroluminescent device was manufactured under the same process condition as in Example 1 described above, except that the following compound was doped to the hole injection layer instead of Compound A-1. The following compound was synthesized using a method specified in Angewante Chemistry International Edition 2011, page 11103.

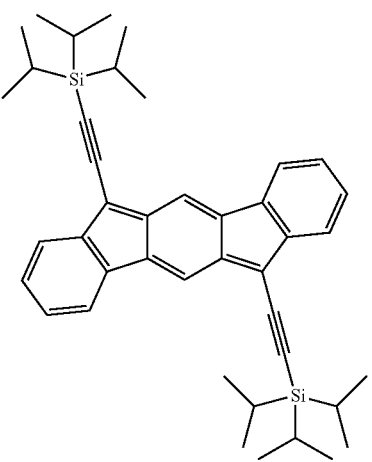 [SMILES: CC(C)[Si](C#CC1=c2cc3c(cc2-c2ccccc21)=C(C#C[Si](C(C)C)(C(C)C)C(C)C)c1ccccc1-3)(C(C)C)C(C)C]

Comparative Example 4

An organic electroluminescent device was manufactured under the same process condition as in Example 1 described above, except that the following compound was doped to the hole injection layer instead of Compound A-1. The following compound was synthesized using a method specified in Angewante Chemistry International Edition 2011, page 11103.

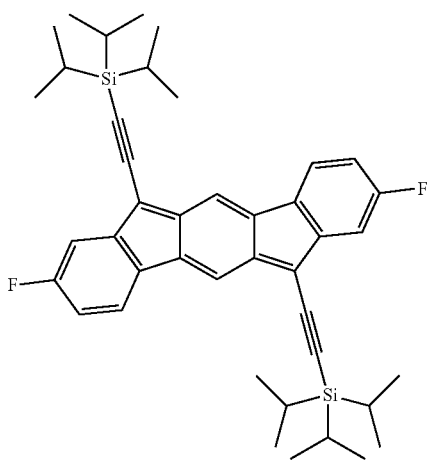 [SMILES: CC(C)[Si](C#CC1=c2cc3c(cc2-c2ccc(F)cc21)=C(C#C[Si](C(C)C)(C(C)C)C(C)C)c1cc(F)ccc1-3)(C(C)C)C(C)C]

Driving voltage, current efficiency, power efficiency and luminance of the organic light emitting devices manufactured in Examples 1 to 9 and Comparative Examples 1 to 4 are listed in the following Table 1.

Example of Application in Device 2—Use in Hole Injection Layer

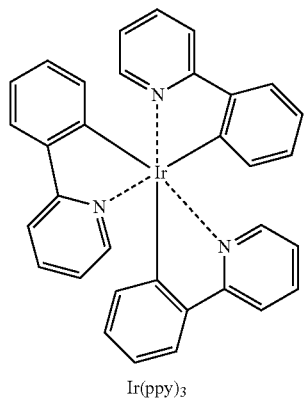

Ir(ppy)$_3$

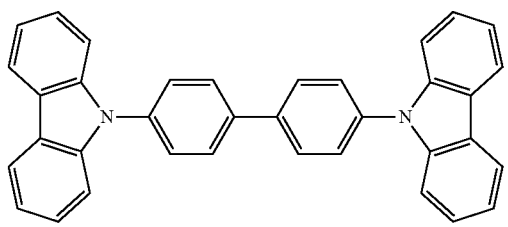

CBP

TABLE 1

| | Hole Injection Layer Doping Material | Driving Voltage (V) | Current Density (mA/cm$^2$) | Current Efficiency (cd/A) | Power Efficiency (lm/W) | Luminance (cd/m$^2$) |
|---|---|---|---|---|---|---|
| Example 1 | Compound A-1 | 4.5 | 10 | 5.6 | 3.910 | 560 |
| Example 2 | Compound A-2 | 4.3 | 10 | 5.48 | 4.004 | 548 |
| Example 3 | Compound A-3 | 4.8 | 10 | 5.38 | 3.521 | 538 |
| Example 4 | Compound A-4 | 4.4 | 10 | 5.6 | 3.998 | 560 |
| Example 5 | Compound A-5 | 4 | 10 | 5.62 | 4.414 | 562 |
| Example 6 | Compound A-6 | 4.7 | 10 | 5.4 | 3.609 | 540 |
| Example 7 | Compound A-7 | 4.3 | 10 | 5.62 | 4.106 | 562 |
| Example 8 | Compound A-8 | 4.1 | 10 | 5.8 | 4.444 | 580 |
| Example 9 | Compound A-9 | 4.8 | 10 | 5.2 | 3.403 | 520 |
| Comparative Example 1 | HAT-CN | 5.8 | 10 | 4.58 | 2.481 | 458 |
| Comparative Example 2 | — | 6.8 | 10 | 4.6 | 2.125 | 460 |
| Comparative Example 3 | Silyl-based Compound | 8 | 10 | 4.22 | 1.657 | 422 |
| Comparative Example 4 | Silyl-based Compound | 8 | 10 | 4.2 | 1.649 | 420 |

-continued

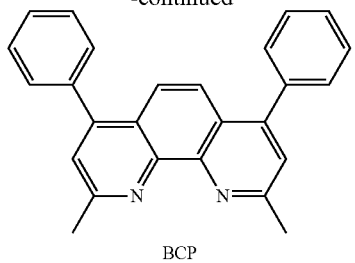
BCP

Example 10

An ITO glass was patterned so that a light emitting area became a 3 mm×3 mm size, and then cleaned. After installing the substrate in a vacuum chamber, the base pressure was set at 1×10$^{-6}$ torr, and as organic materials on the ITO, an anode, Compound A-1 was formed to a thickness of 40 Å as a hole injection layer, α-NPB was formed to a thickness of 800 Å as a hole transfer layer, a yellow light emitting layer was formed to a thickness of 300 Å by doping Ir(ppy)$_3$, a dopant, on CBP, a host, in a doping concentration of 10% by weight, BCP was formed to a thickness of 50 Å as a hole suppression layer, Alq$_3$ was formed to a thickness of 150 Å as an electron transfer layer, LiF was formed to a thickness of 5 Å as an electron injection layer, and Al was formed to a thickness of 1000 Å as a cathode in this order to manufacture an organic electroluminescent device.

Example 11

An organic electroluminescent device was manufactured under the same process condition as in Example 10 described above, except that Compound A-2 was used in the hole injection layer instead of Compound A-1.

Example 12

An organic electroluminescent device was manufactured under the same process condition as in Example 10 described above, except that Compound A-3 was used in the hole injection layer instead of Compound A-1.

Example 13

An organic electroluminescent device was manufactured under the same process condition as in Example 10 described above, except that Compound A-10 was used in the hole injection layer instead of Compound A-1.

Example 14

An organic electroluminescent device was manufactured under the same process condition as in Example 10 described above, except that Compound A-11 was used in the hole injection layer instead of Compound A-1.

Example 15

An organic electroluminescent device was manufactured under the same process condition as in Example 10 described above, except that Compound A-12 was used in the hole injection layer instead of Compound A-1.

Comparative Example 5

An organic electroluminescent device was manufactured under the same process condition as in Example 10 described above, except that HAT-CN was used in the hole injection layer instead of Compound A-1.

Comparative Example 6

An organic electroluminescent device was manufactured under the same process condition as in Example 10 described above, except that the hole injection layer was not formed.

Comparative Example 7

An organic electroluminescent device was manufactured under the same process condition as in Example 10 described above, except that the following compound was used in the hole injection layer instead of Compound A-1. The following compound was synthesized using a method specified in Angewante Chemistry International Edition 2011, page 11103.

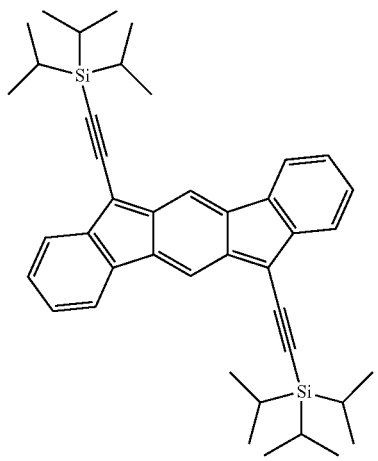 [SMILES: CC(C)[Si](C#CC1=c2cc3c(cc2-c2ccccc21)=C(C#C[Si](C(C)C)(C(C)C)C(C)C)c1ccccc1-3)(C(C)C)C(C)C]

Comparative Example 8

An organic electroluminescent device was manufactured under the same process condition as in Example 10 described above, except that the following compound was used in the hole injection layer instead of Compound A-1. The following compound was synthesized using a method specified in Angewante Chemistry International Edition 2011, page 11103.

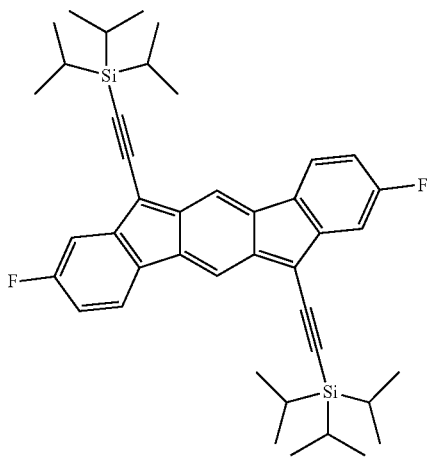 [SMILES: CC(C)[Si](C#CC1=c2cc3c(cc2-c2ccc(F)cc21)=C(C#C[Si](C(C)C)(C(C)C)C(C)C)c1cc(F)ccc1-3)(C(C)C)C(C)C]

Driving voltage, current efficiency, power efficiency and luminance of the organic light emitting devices manufactured in Examples 10 to 15 and Comparative Examples 5 to 8 are listed in the following Table 2.

TABLE 2

|  | Hole Injection Layer Material | Driving Voltage (V) | Current Density (mA/cm$^2$) | Current Efficiency (cd/A) | Power Efficiency (lm/W) | Luminance (cd/m$^2$) |
|---|---|---|---|---|---|---|
| Example 10 | Compound A-1 | 4.5 | 10 | 60.04 | 41.916 | 6004 |
| Example 11 | Compound A-2 | 4.3 | 10 | 61 | 44.567 | 6100 |
| Example 12 | Compound A-3 | 4.8 | 10 | 59 | 38.615 | 5900 |
| Example 13 | Compound A-10 | 4.4 | 10 | 60.18 | 42.968 | 6018 |
| Example 14 | Compound A-11 | 4 | 10 | 62.2 | 48.852 | 6220 |
| Example 15 | Compound A-12 | 4.7 | 10 | 58.84 | 39.330 | 5884 |
| Comparative Example 5 | HAT-CN | 6 | 10 | 50.32 | 26.347 | 5032 |
| Comparative Example 6 | — | 8.6 | 10 | 43.49 | 15.887 | 4349 |
| Comparative Example 7 | Silyl-based Compound | 8 | 10 | 44.88 | 17.624 | 4488 |
| Comparative Example 8 | Silyl-based Compound | 8 | 10 | 44.68 | 17.546 | 4468 |

Hereinbefore, preferred embodiments of the present disclosure have been described, however, the present disclosure is not limited thereto, and various modifications may be made within the scope of the claims and the detailed descriptions, and the modifications are also included in the scope of the present disclosure.

The invention claimed is:

1. An organic light emitting device comprising:

a first electrode:

a second electrode provided opposite to the first electrode: and one or more organic material layers provided between the first electrode and the second electrode, wherein the one or more organic material layers comprise one of a hole injection layer, a hole buffer layer, a hole transfer layer, and an electron suppression layer, and wherein the hole injection layer, the hole buffer layer, the hole transfer layer, or the electron suppression layer comprise a compound of the following Chemical Formula 1:

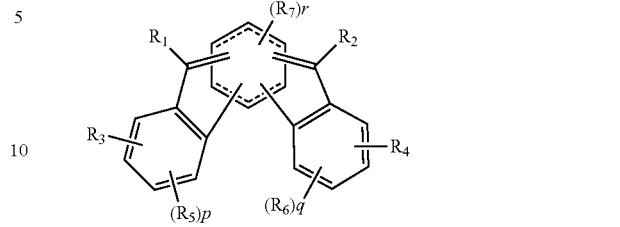

[Chemical Formula 1]

wherein, in Chemical Formula 1, $R_1$ and $R_2$ are the same as or different from each other, and are each independently a substituted or unsubstituted phenyl group; or a substituted or unsubstituted N-containing monocyclic heterocyclic group;

$R_3$ and $R_4$ are the same as or different from each other, and are each independently a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted alkylsilyl group; a substituted or unsubstituted arylsilyl group; a substituted or unsubstituted cyanoaryl group; a substituted or unsubstituted alkylaryl group; a substituted or unsubstituted haloalkylaryl group; a substituted or unsubstituted aryl group; a substituted or unsubstituted haloaryl group; or a substituted or unsubstituted heterocyclic group; and $R_5$ to $R_7$ are the same as or different from each other, and are each independently hydrogen; deuterium; a halogen group; a substituted or unsubstituted alkyl group; a substituted or unsubstituted haloalkyl group; a substituted or unsubstituted cycloalkyl group; a substituted or unsubstituted alkoxy group; a substituted or unsubstituted haloalkoxy group; a substituted or unsubstituted aryloxy group; a substituted or unsubstituted alkenyl group; a substituted or unsubstituted aralkyl group; a substituted or unsubstituted aralkenyl group; a substituted or unsubstituted alkylaryl group; a substituted or unsubstituted haloalkylaryl group; a substituted or unsubstituted aryl group; a substituted or unsubstituted haloaryl group; or a substituted or unsubstituted heterocyclic group, p and q are each an integer of 0 to 3, r is an integer of 0 to 2, when p is 2 or greater, $R_5$s are the same as or different from each other, when q is 2 or greater, $R_6$s are the same as or different from each other, and when r is 2, $R_7$s are the same as or different from each other.

2. The organic light emitting device of claim 1, wherein Chemical Formula 1 is represented by one of the following Chemical Formulae 2, 3 and 5 to 7:

[Chemical Formula 2]

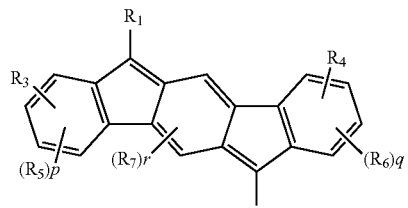

[Chemical Formula 3]

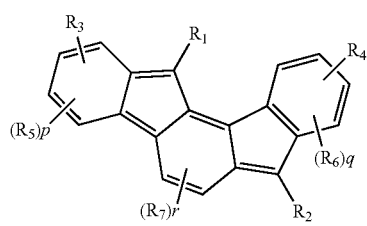

[Chemical Formula 5]

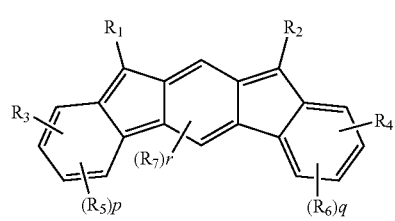

[Chemical Formula 6]

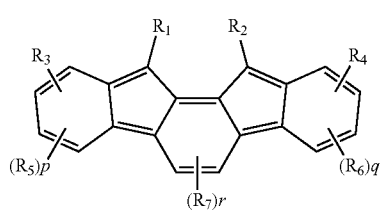

[Chemical Formula 7]

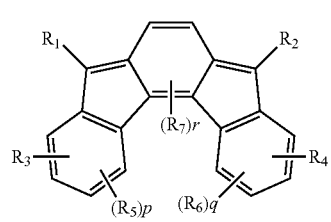

wherein, in Chemical Formulae 2, 3 and 5 to 7, definitions of substituents are the same as in Chemical Formula 1.

3. The organic light emitting device of claim 1, wherein $R_1$ and $R_2$ are the same as or different from each other, and are each independently represented by the following Chemical Formula 14:

[Chemical Formula 14]

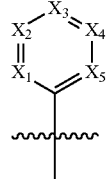

wherein, in Chemical Formula 14, $X_1$ to $X_5$ are the same as or different from each other, and are each independently CH, CR, or N; and R is deuterium; a halogen group; a nitrile group; an alkyl group; a haloalkyl group; an alkoxy group; or a haloalkoxy group.

4. The organic light emitting device of claim 3, wherein R is a fluoro group, a nitrile group, $CF_3$, $CF_3$, $OCH_3$, or $OCF_3$.

5. The organic light emitting device of claim 1, wherein $R_1$ and $R_2$ are the same as or different from each other, and are each independently selected from among the following structural formulae:

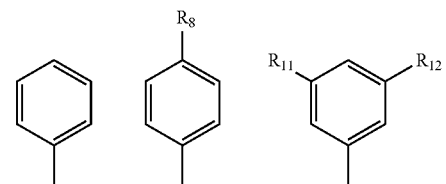

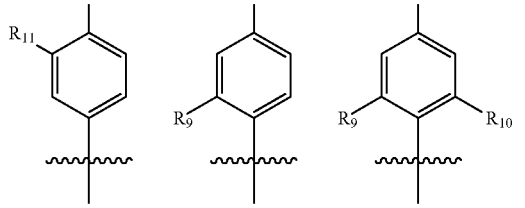

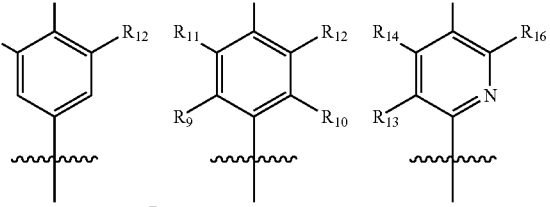

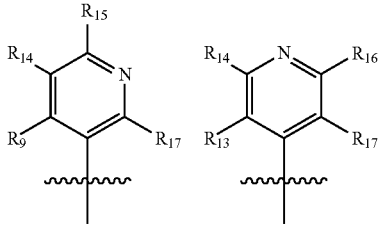

wherein, in the structural formulae, $R_8$ to $R_{12}$ are the same as or different from each other, and are each independently deuterium; a halogen group; a nitrile group; an alkyl group; a haloalkyl group; an alkoxy group; or a haloalkoxy group, $R_{13}$ to $R_{17}$ are the same as or different from each other, and are each independently hydrogen; deuterium; a halogen group; a nitrile group; an alkyl group; a haloalkyl group; an alkoxy group; or a haloalkoxy group.

6. The organic light emitting device of claim 1, wherein $R_1$ and $R_2$ are the same as or different from each other, and are each independently selected from among the following structural formulae:

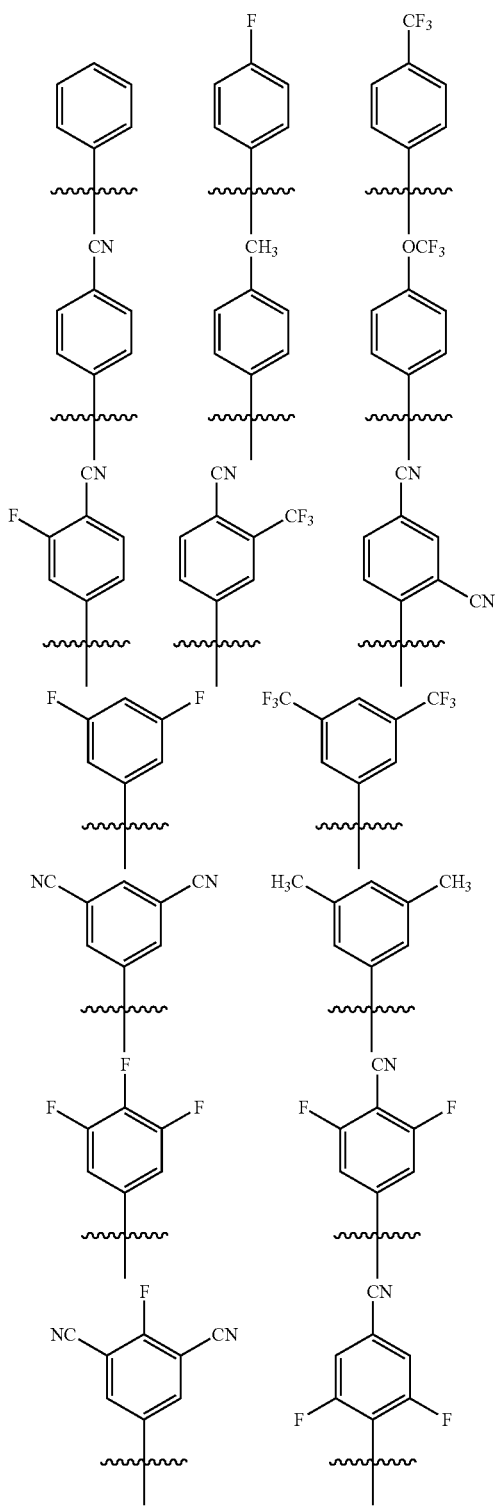

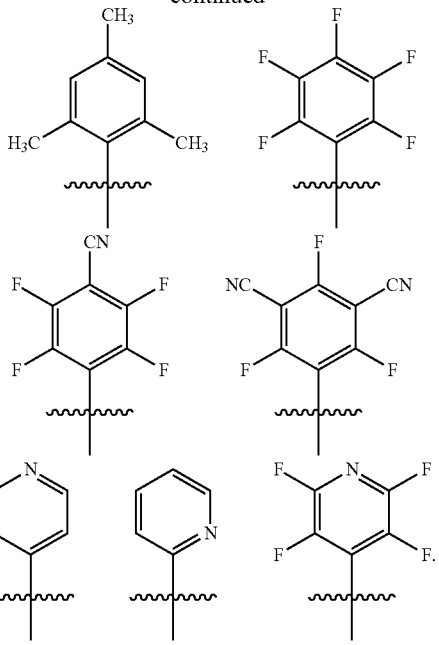

7. The organic light emitting device of claim 1, wherein $R_3$ and $R_4$ are the same as or different from each other, and are each independently a halogen group; a nitrile group; a substituted or unsubstituted haloalkyl group; a substituted or unsubstituted haloalkoxy group; a substituted or unsubstituted haloalkylaryl group; a substituted or unsubstituted aryl group; a substituted or unsubstituted haloaryl group; or a substituted or unsubstituted heterocyclic group.

8. The organic light emitting device of claim 1, wherein $R_3$ and $R_4$ are the same as or different from each other, and are each independently a fluoro group; a nitrile group; a fluoroalkyl group; a fluoroalkoxy group; a fluoroalkylaryl group; an aryl group; a fluoroaryl group; or a heterocyclic group containing N, O, or S.

9. The organic light emitting device of claim 1, wherein the compound of Chemical Formula 1 selected from among the following compounds:

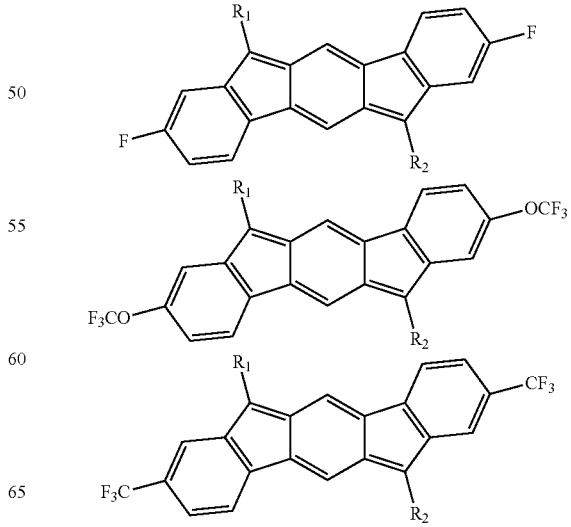

-continued
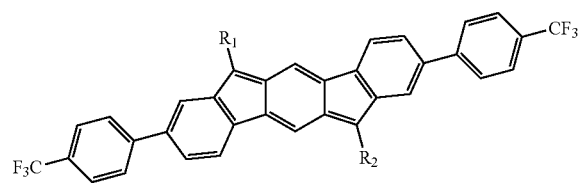
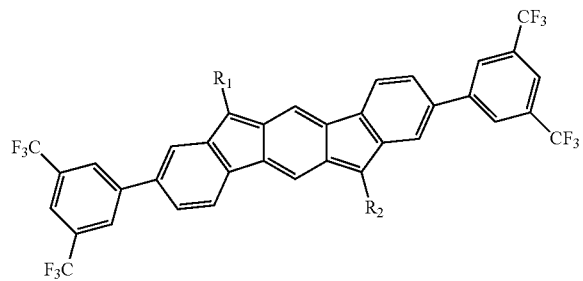
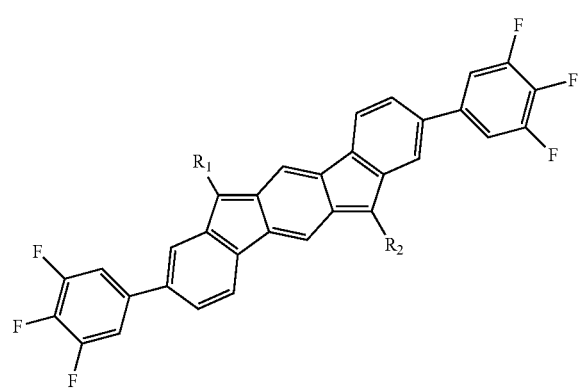
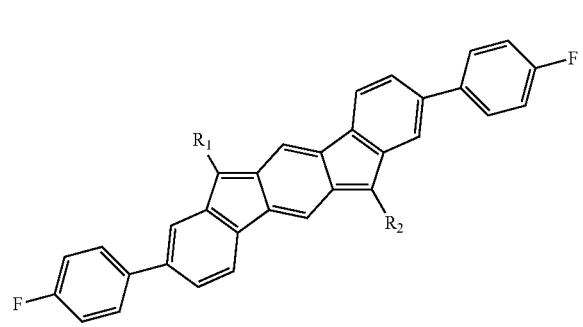
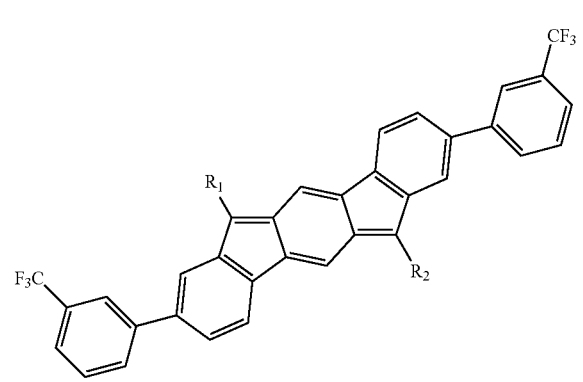
-continued
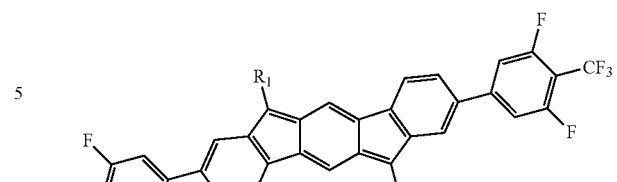
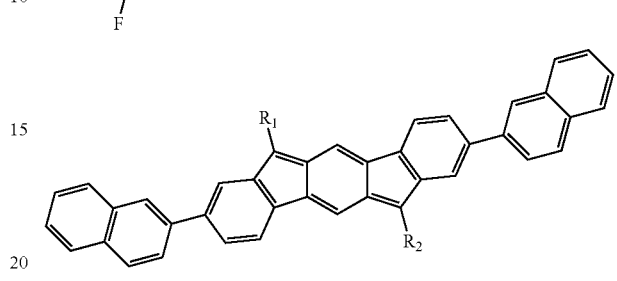
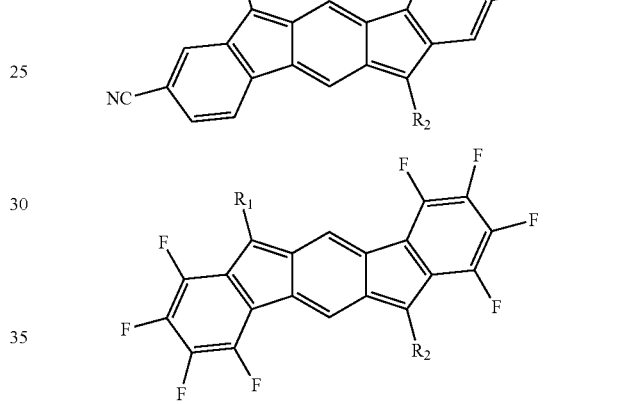
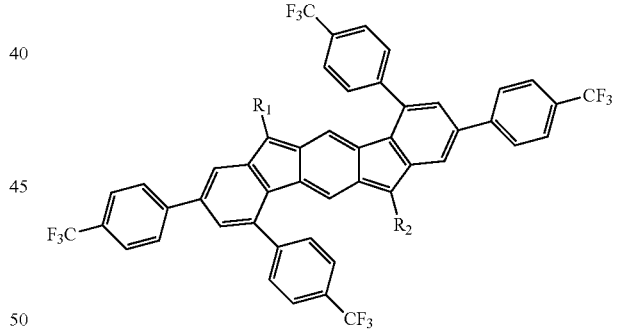
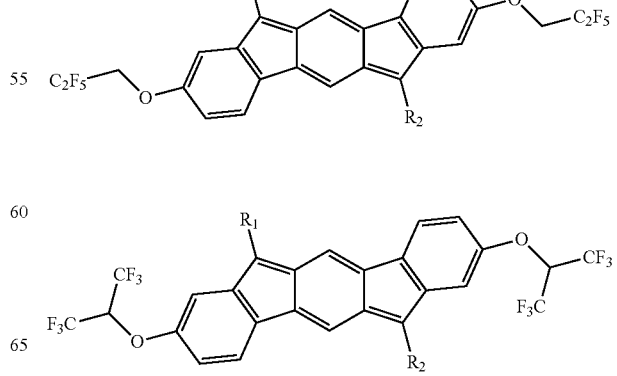

71
-continued
72
-continued
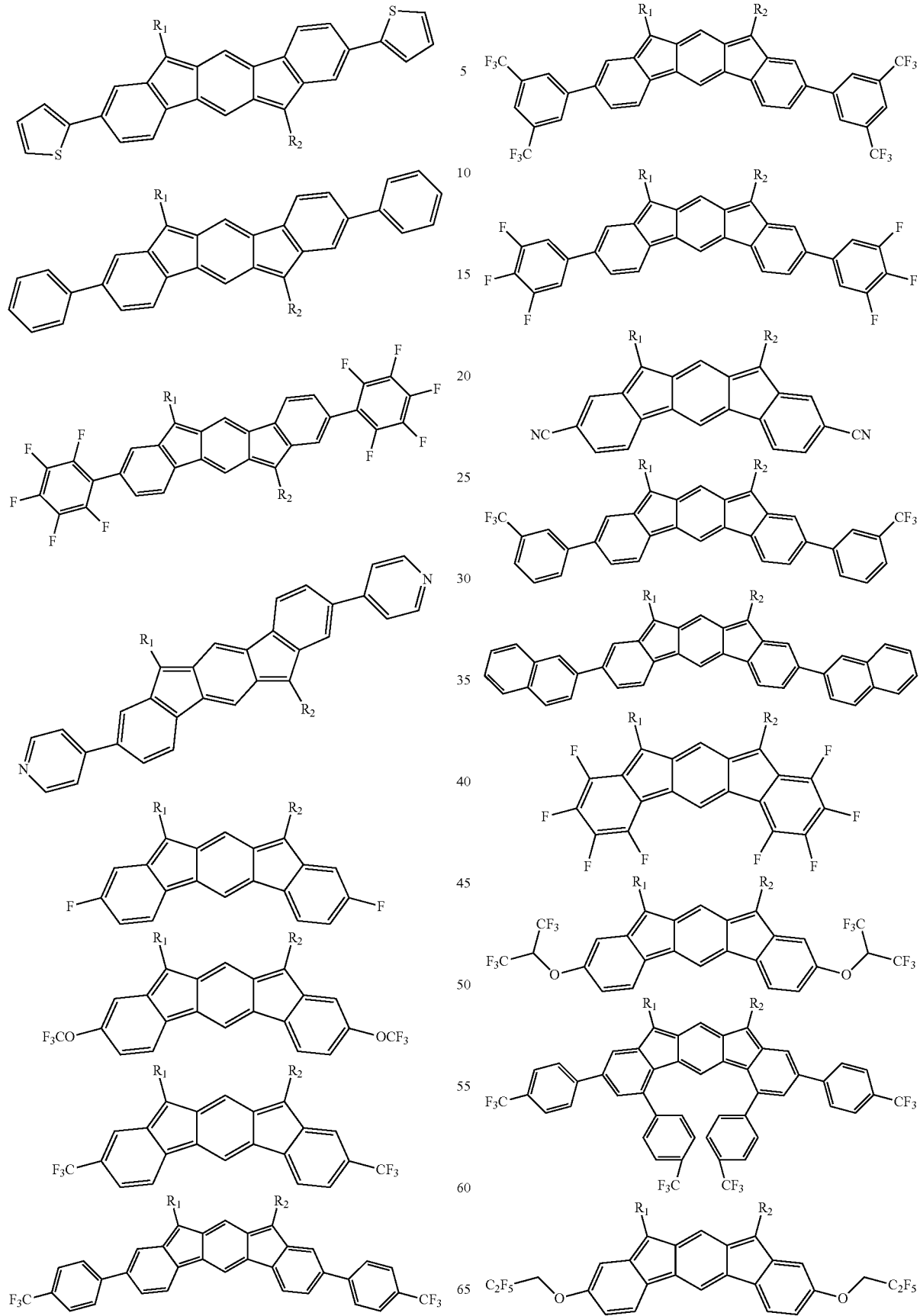

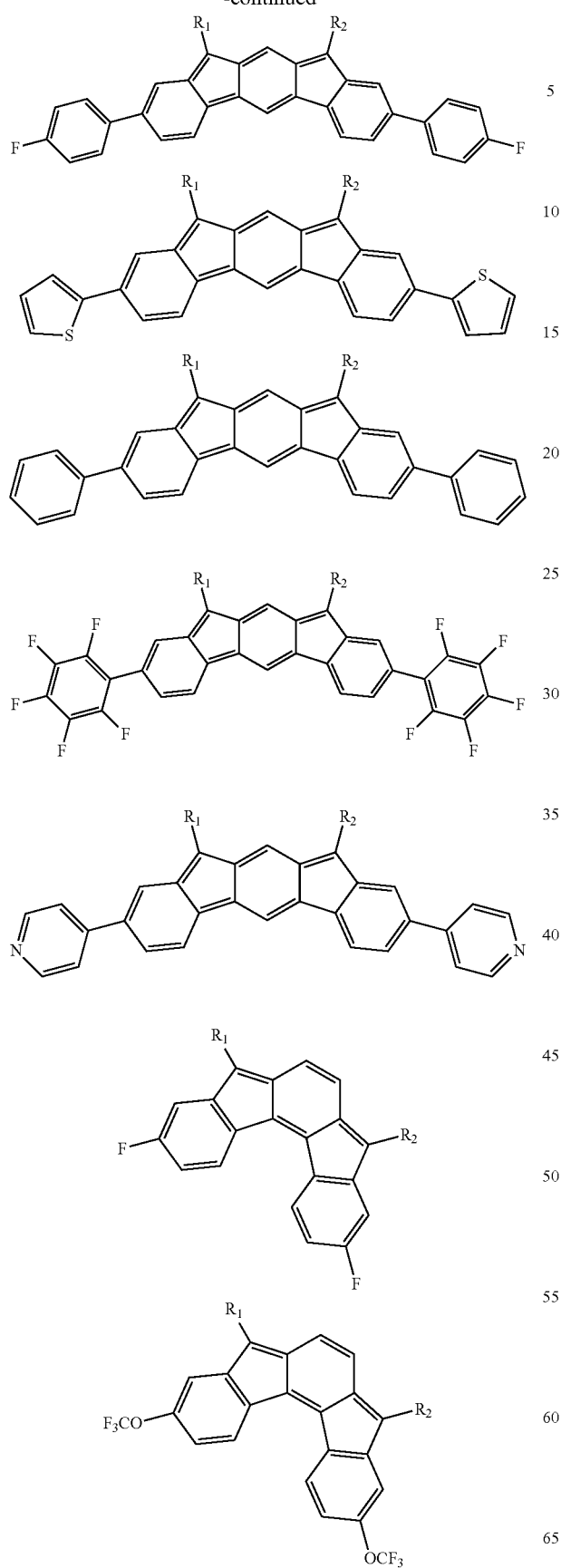
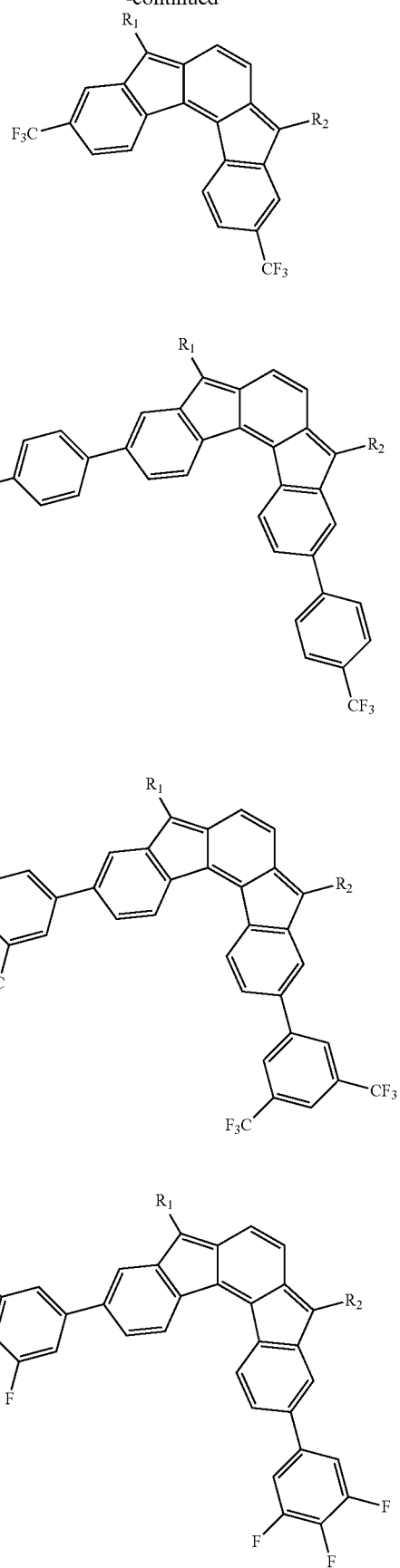

75
-continued
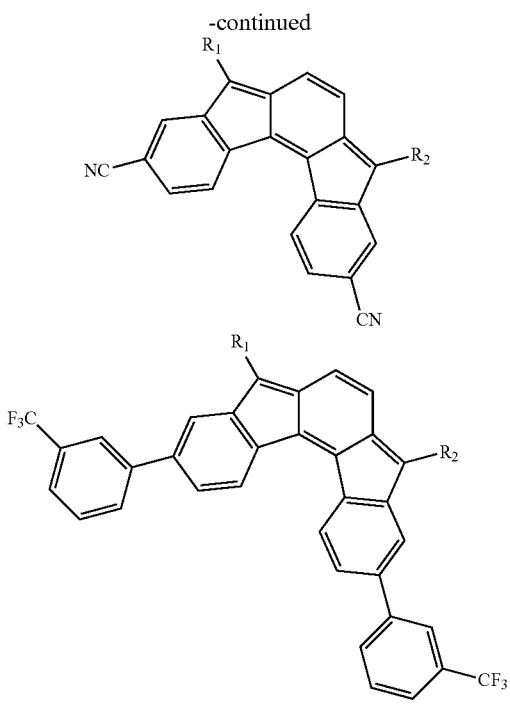
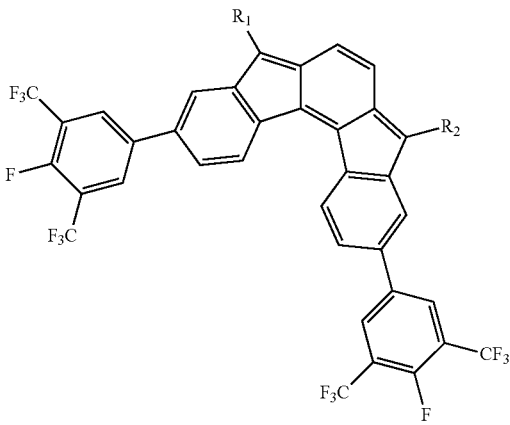
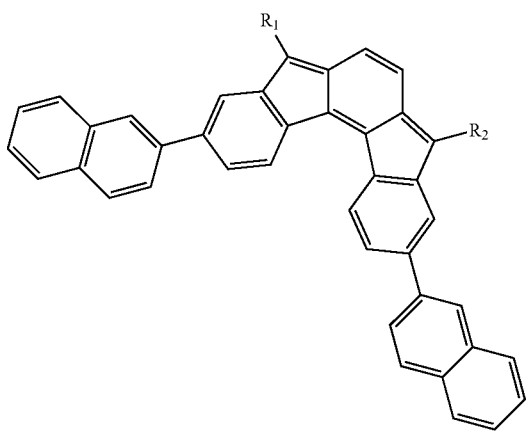
76
-continued
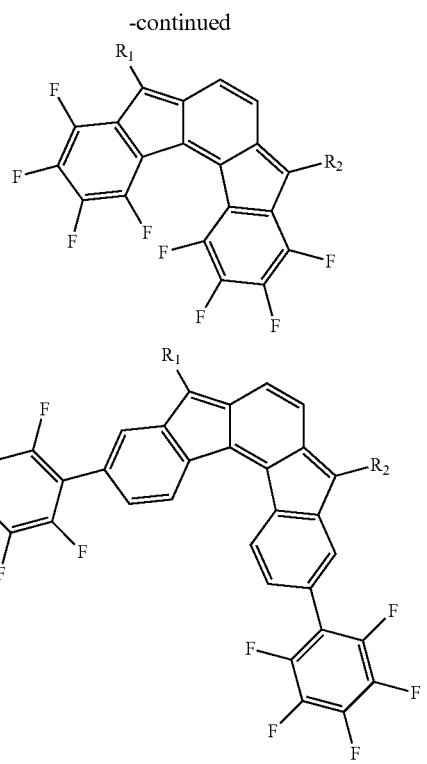
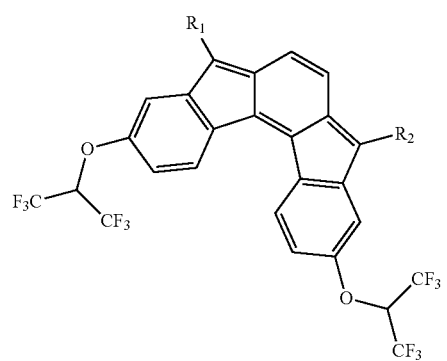
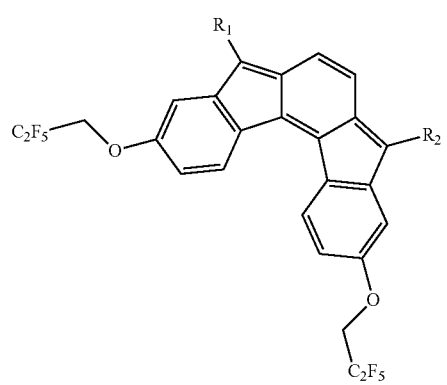

77
-continued
78
-continued
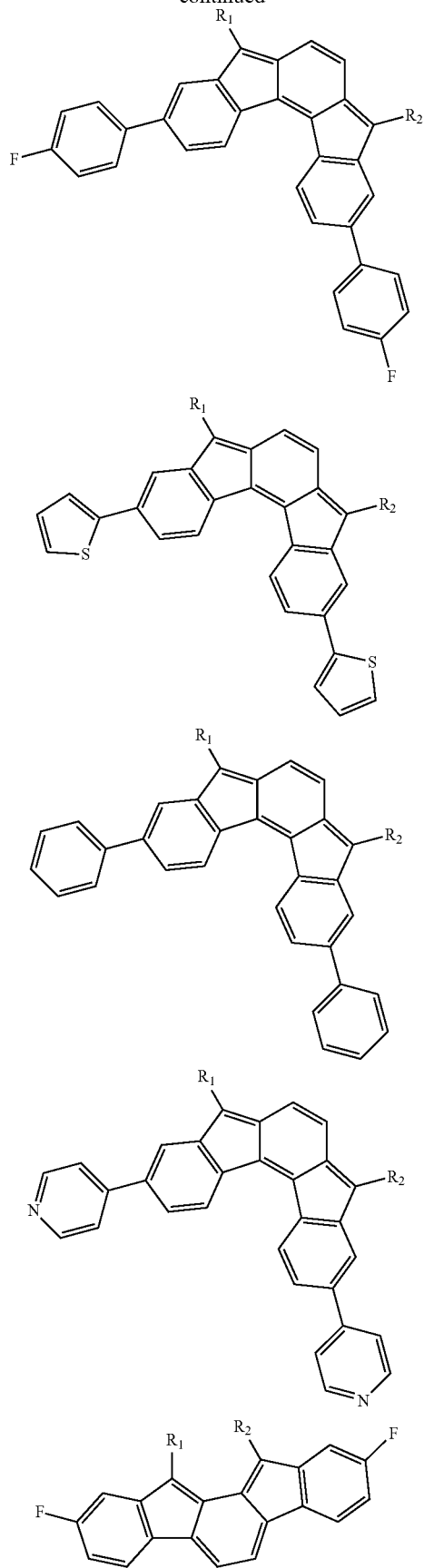
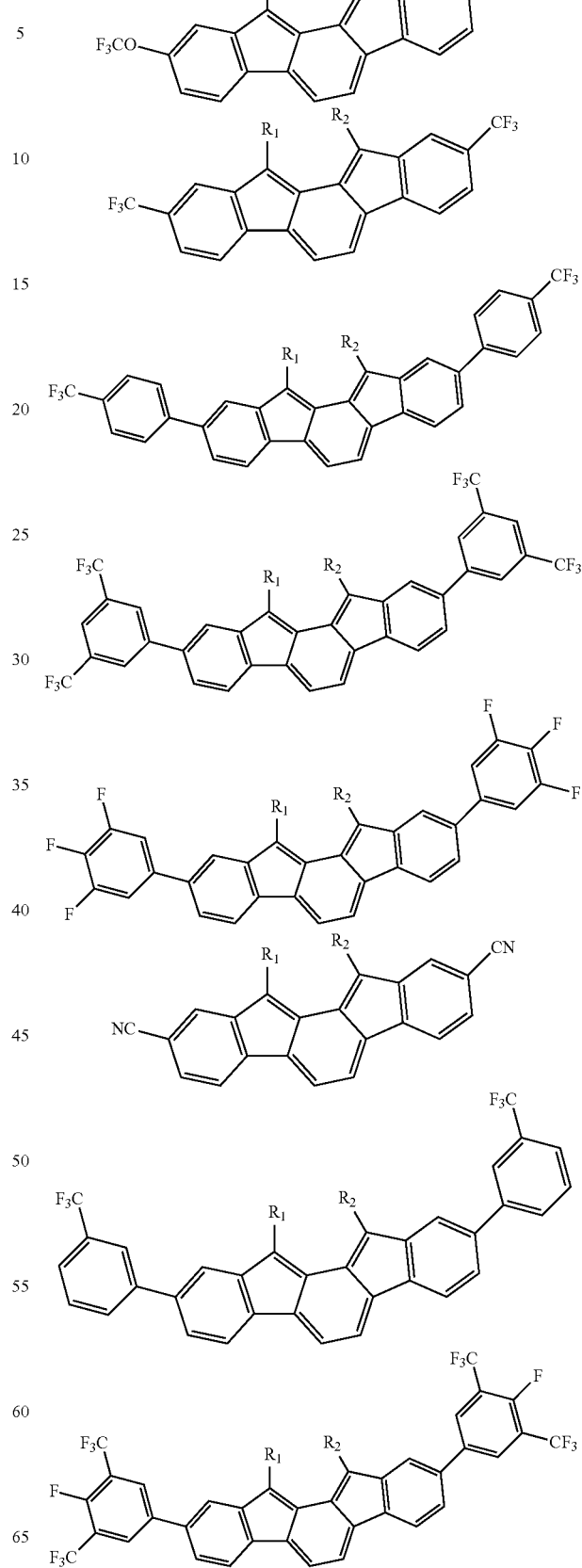

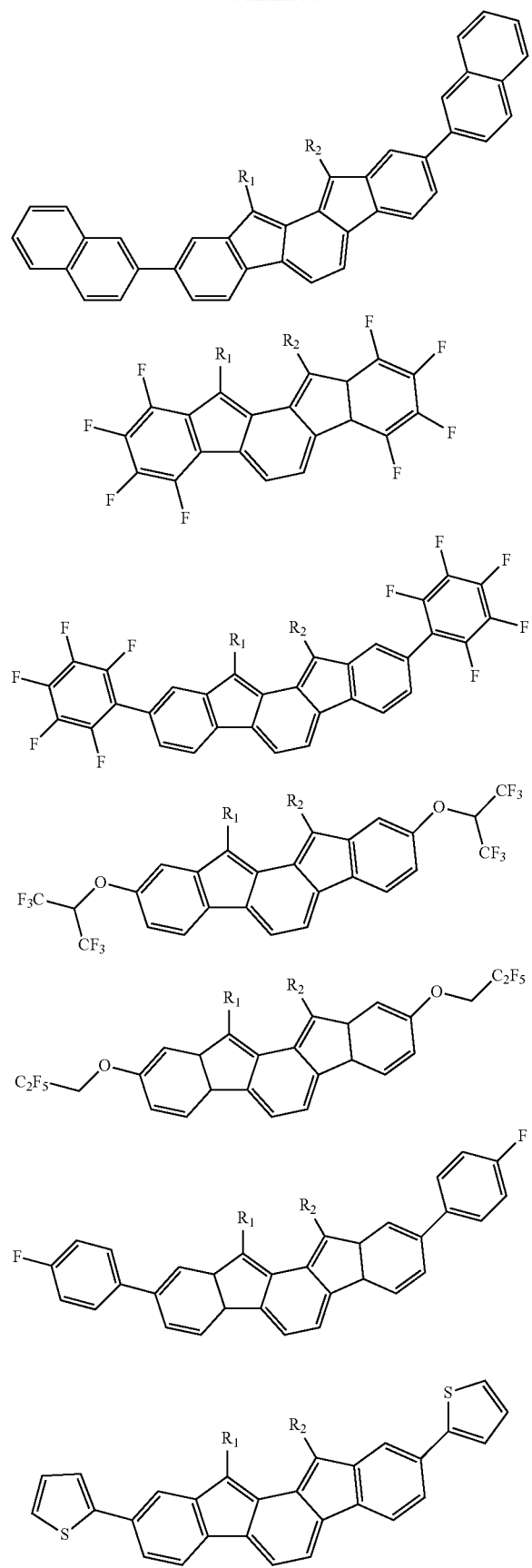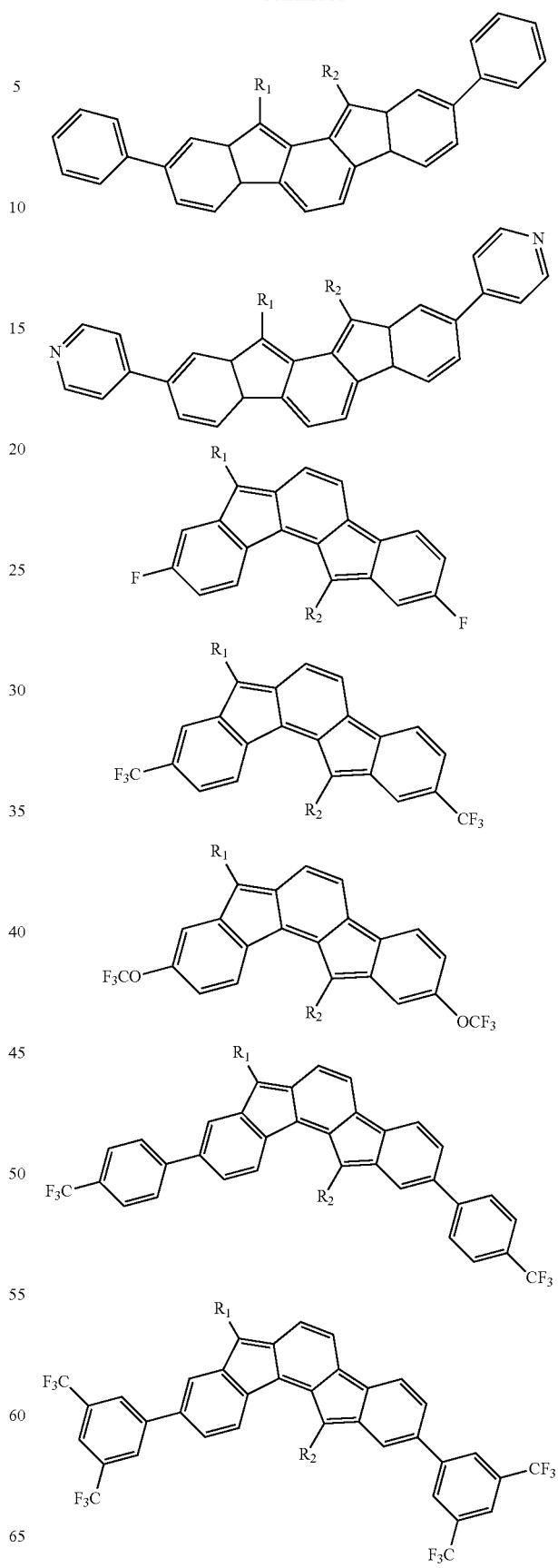

81
-continued
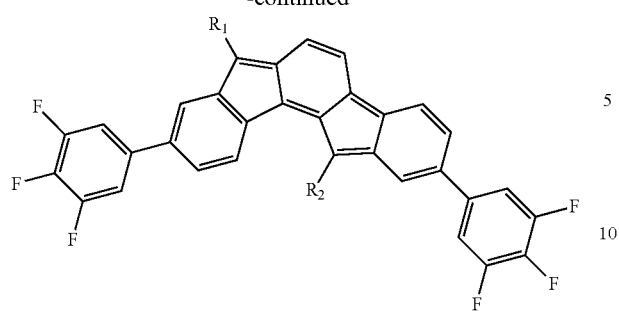
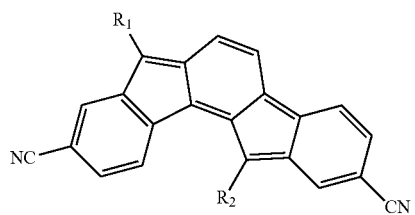
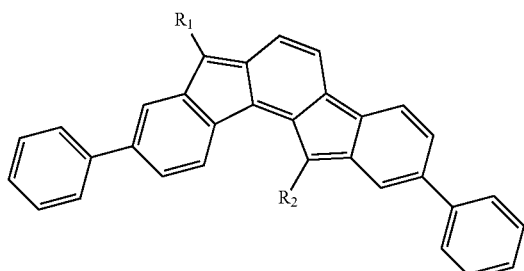
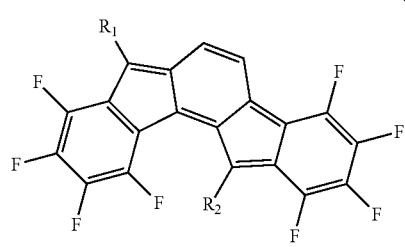
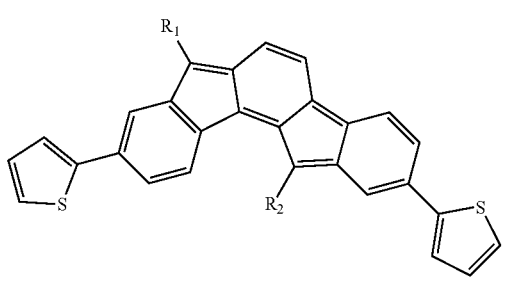
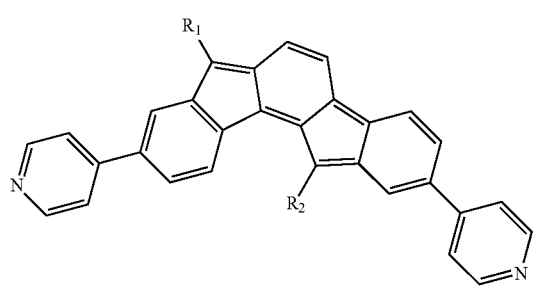
82
-continued
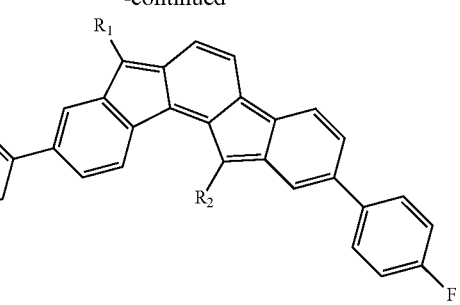
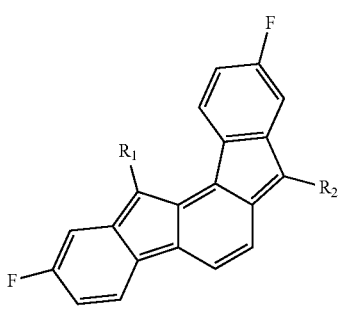
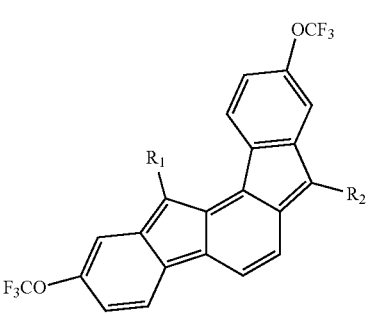
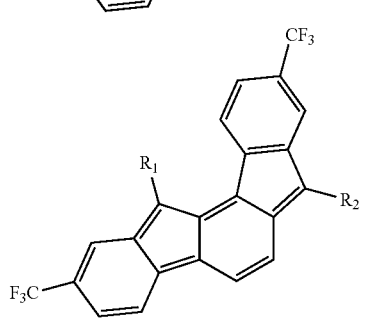
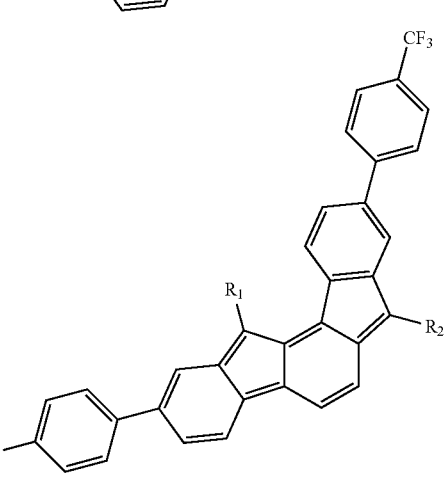

83
-continued
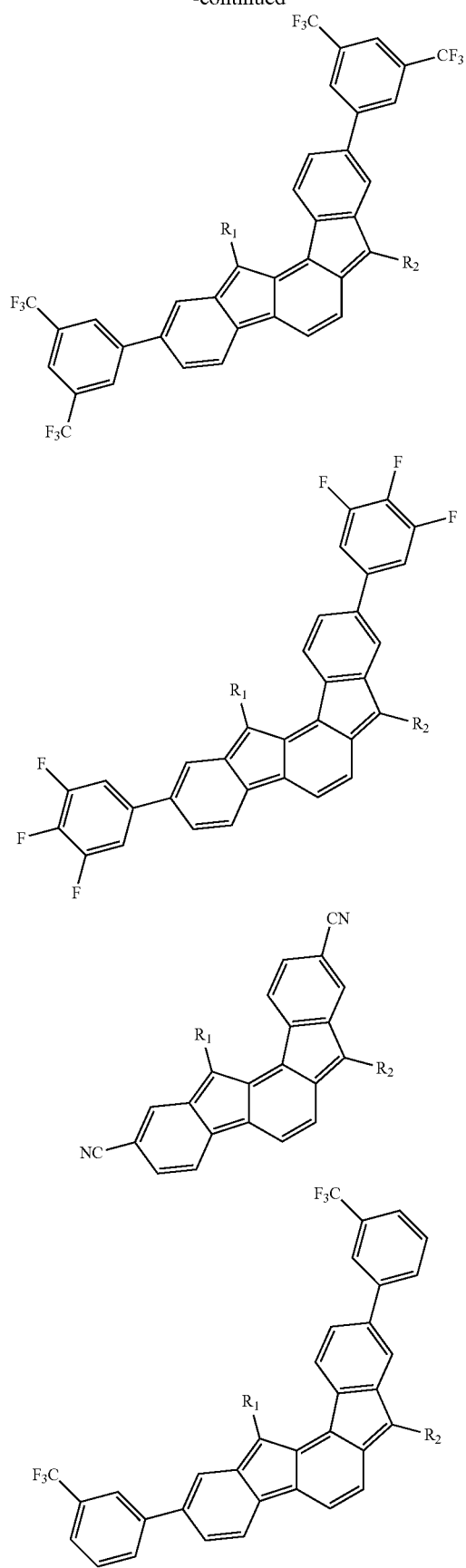
84
-continued
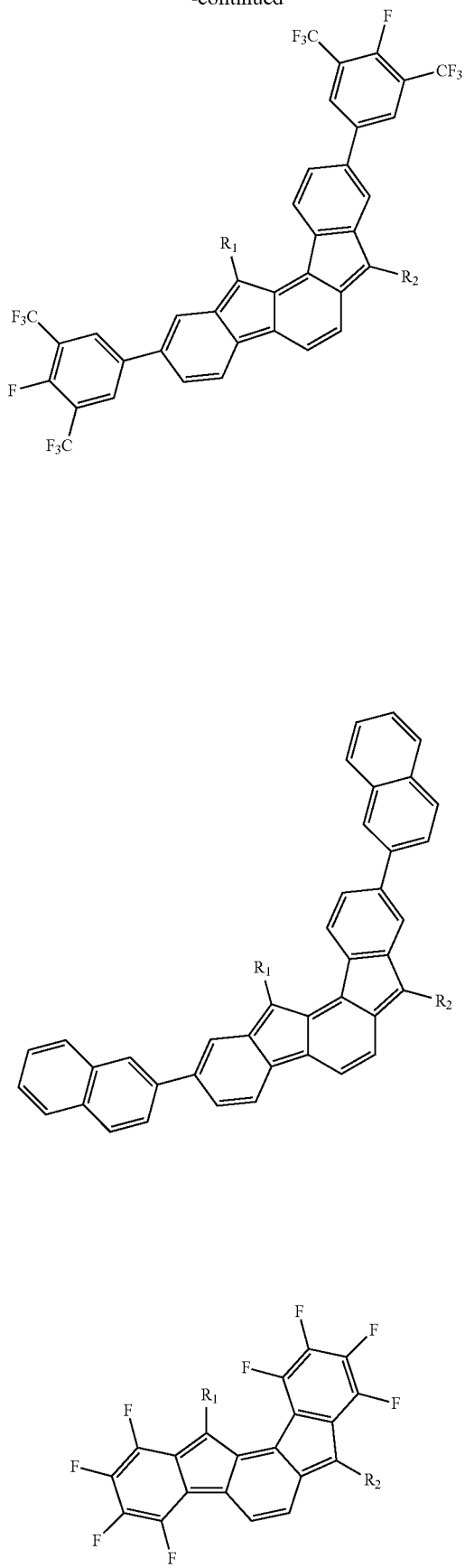

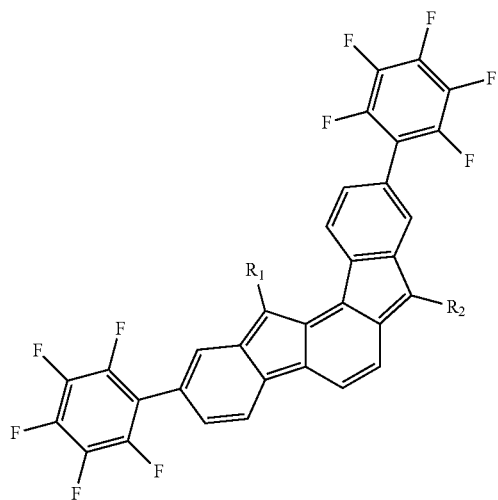

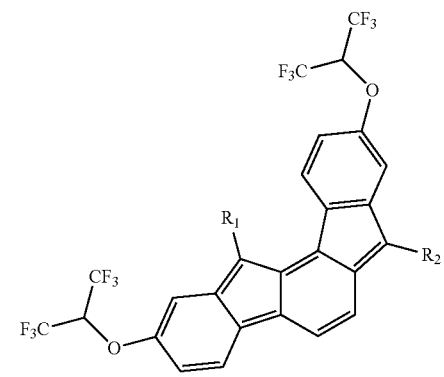

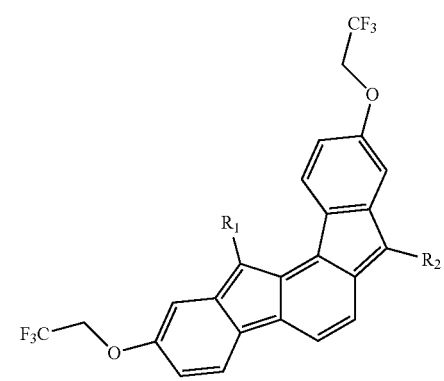

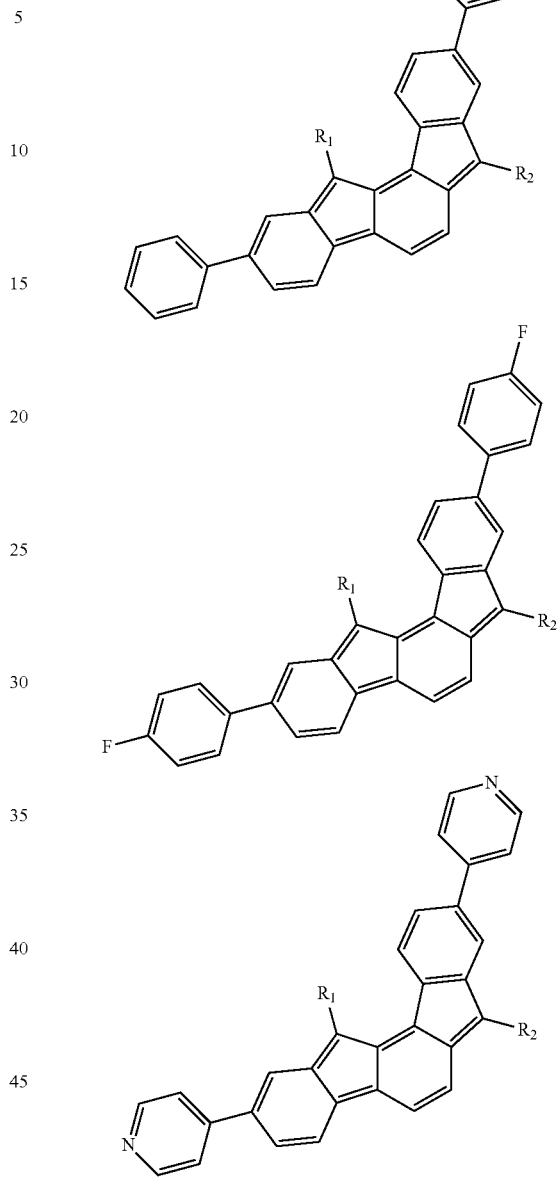

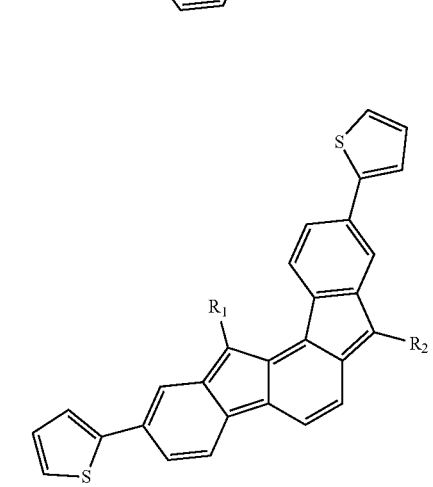

wherein, in the structural formulae, definitions of $R_1$ and $R_2$ are the same as in Chemical Formula 1.

10. The organic light emitting device of claim 1, wherein the hole injection layer, the hole buffer layer, the hole transfer layer, or the electron suppression layer is formed only with the compound.

11. The organic light emitting device of claim 1, wherein the hole injection layer, the hole buffer layer, the hole transfer layer, or the electron suppression layer comprises the compound in 0.1% by weight to 50% by weight based on a weight of each of the each layers.

12. The organic light emitting device of claim 1, wherein the organic material layer comprises two or more light emitting layers, and further comprises a charge generation layer comprising the compound provided between the two light emitting layers.

13. The organic light emitting device of claim 1, wherein the organic material layer comprises a light emitting layer, and the light emitting layer comprises a compound represented by the following Chemical Formula A-1:

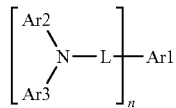

[Chemical Formula A-1]

wherein, in Chemical Formula A-1,

Ar1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group;

L is a direct bond; a substituted or unsubstituted arylene group; or a substituted or unsubstituted heteroarylene group;

Ar2 and Ar3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or bond to each other to form a substituted or unsubstituted ring;

n is an integer of 1 or greater; and when n is 2 or greater, substituents in the parentheses are the same as or different from each other.

14. The organic light emitting device of claim 13, wherein L is a direct bond, Ar1 is a substituted or unsubstituted divalent pyrene group, Ar2 and Ar3 are the same as or different from each other, and are each independently an aryl group unsubstituted or substituted with a germanium group, and n is 2.

15. The organic light emitting device of claim 1, wherein the organic material layer comprises a light emitting layer, and the light emitting layer comprises a compound represented by the following Chemical Formula A-2:

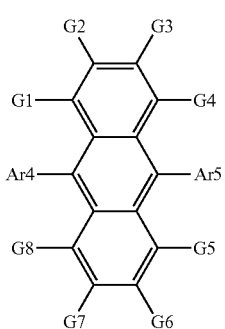

[Chemical Formula A-2]

wherein, in Chemical Formula A-2,

Ar4 and Ar5 are the same as or different from each other, and are each independently a substituted or unsubstituted monocyclic aryl group; or a substituted or unsubstituted multicyclic aryl group; and G1 to G8 are the same as or different from each other, and are each independently hydrogen; a silyl group; a halogen group; a cyano group; a substituted or unsubstituted monocyclic aryl group; a substituted or unsubstituted multicyclic aryl group; a substituted or unsubstituted alkyl group; a substituted or unsubstituted cycloalkyl group; or a substituted or unsubstituted alkoxy group.

16. The organic light emitting device of claim 15, wherein Ar4 and Ar5 are the same as or different from each other and are each independently a 2-naphthyl group, and G1 to G8 are hydrogen; or a substituted or unsubstituted alkyl group.

17. The organic light emitting device of claim 13, wherein the light emitting layer further comprises a compound represented by the following Chemical Formula A-2:

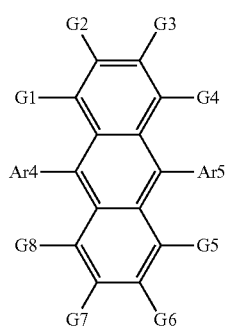

[Chemical Formula A-2]

wherein, in Chemical Formula A-2,

Ar4 and Ar5 are the same as or different from each other, and are each independently a substituted or unsubstituted monocyclic aryl group; or a substituted or unsubstituted multicyclic aryl group;

G1 to G8 are the same as or different from each other, and are each independently hydrogen; a silyl group; a halogen group; a cyano group; a substituted or unsubstituted monocyclic aryl group; a substituted or unsubstituted multicyclic aryl group; a substituted or unsubstituted alkyl group; a substituted or unsubstituted cycloalkyl group; or a substituted or unsubstituted alkoxy group.

18. The organic light emitting device of claim 1, wherein Chemical Formula 1 is represented by one of the following Chemical Formulae 3 and 5 to 7:

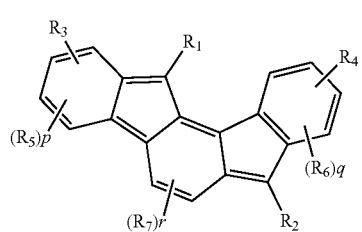

[Chemical Formula 3]

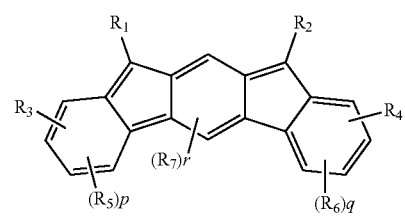

[Chemical Formula 5]

-continued
[Chemical Formula 6]
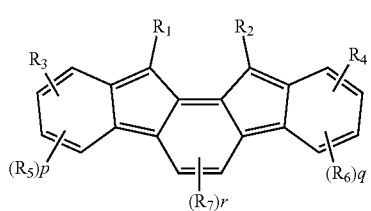
[Chemical Formula 7]
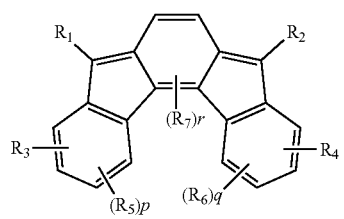
wherein, in Chemical Formulae 3 and 5 to 7, definitions of substituents are the same as in Chemical Formula 1.
* * * * *